(12) United States Patent
Boulton et al.

(10) Patent No.: US 12,162,859 B2
(45) Date of Patent: Dec. 10, 2024

(54) CRYSTALLINE AND AMORPHOUS FORMS OF A COMPOUND FOR THE TARGETED DEGRADATION OF ESTROGEN RECEPTOR

(71) Applicant: Arvinas Operations, Inc., New Haven, CT (US)

(72) Inventors: Katharine Victoria Boulton, Edinburgh (GB); Chungpin Herman Chen, Madison, CT (US); Royal J. Haskell, III, Durham, CT (US); Hayley Reece, Dalkeith (GB)

(73) Assignee: Arvinas Operations, Inc., New Haven, CT (US)

( * ) Notice: Subject to any disclaimer, the term of this patent is extended or adjusted under 35 U.S.C. 154(b) by 0 days.

(21) Appl. No.: 17/472,847

(22) Filed: Sep. 13, 2021

(65) Prior Publication Data

US 2022/0081416 A1  Mar. 17, 2022

Related U.S. Application Data

(60) Provisional application No. 63/078,225, filed on Sep. 14, 2020.

(51) Int. Cl.
*C07D 401/14* (2006.01)

(52) U.S. Cl.
CPC ........ *C07D 401/14* (2013.01); *C07B 2200/13* (2013.01)

(58) Field of Classification Search
CPC  C07D 401/14; C07B 2200/13; A61K 31/496; A61P 35/00; A61P 15/00
USPC ........................................................ 514/253
See application file for complete search history.

(56) References Cited

U.S. PATENT DOCUMENTS

| | | | |
|---|---|---|---|
| 5,492,922 A | 2/1996 | Palkowitz et al. |
| 5,681,835 A | 10/1997 | Willson |
| 5,877,219 A | 3/1999 | Willson |
| 5,916,916 A | 6/1999 | Hauser et al. |
| 6,207,716 B1 | 3/2001 | Willson |
| 6,306,663 B1 | 10/2001 | Kenten et al. |
| 6,670,348 B1 | 12/2003 | Rosen et al. |
| 7,030,141 B2 | 4/2006 | Bigge et al. |
| 7,041,298 B2 | 5/2006 | Deshaies et al. |
| 7,208,157 B2 | 4/2007 | Sakamoto et al. |
| 7,244,851 B2 | 7/2007 | Cohen et al. |
| 7,345,081 B2 | 3/2008 | Cohen et al. |
| 7,419,975 B2 | 9/2008 | Palermo et al. |
| 7,517,906 B2 | 4/2009 | Condon et al. |
| 7,915,293 B2 | 3/2011 | Ramesh et al. |
| 8,012,997 B2 | 9/2011 | Robarge et al. |
| 8,362,065 B2 | 1/2013 | Liu et al. |
| 8,481,568 B2 | 7/2013 | Muller et al. |
| 9,163,007 B2 | 10/2015 | Akritopoulou-Zanze et al. |
| 9,500,653 B2 | 11/2016 | Crews et al. |
| 9,632,089 B2 | 4/2017 | Crews et al. |
| 9,796,698 B2 | 10/2017 | Muller et al. |
| 9,801,868 B2 | 10/2017 | Muller et al. |
| 10,047,151 B2 | 8/2018 | Lopez-Girona et al. |
| 10,647,698 B2 | 5/2020 | Crew et al. |
| 10,899,742 B1 | 1/2021 | Crew et al. |
| 11,104,666 B2 | 8/2021 | Crew et al. |
| 11,261,178 B2 | 3/2022 | Fan et al. |
| 2006/0128632 A1 | 6/2006 | Sharma et al. |
| 2007/0218138 A1 | 9/2007 | Bittorf et al. |
| 2008/0051432 A1 | 2/2008 | Zhang |
| 2008/0214501 A1 | 9/2008 | Pan et al. |
| 2008/0269140 A1 | 10/2008 | Wang et al. |
| 2010/0203012 A1 | 8/2010 | Laurent et al. |
| 2011/0195043 A1 | 8/2011 | Sun et al. |
| 2011/0230457 A1 | 9/2011 | Berghausen et al. |
| 2012/0270800 A1 | 10/2012 | Verdine et al. |
| 2013/0029993 A1 | 1/2013 | Stadtmueller |
| 2014/0235629 A1 | 8/2014 | Bartberger et al. |
| 2014/0243372 A1 | 8/2014 | Rew |

(Continued)

FOREIGN PATENT DOCUMENTS

| | | |
|---|---|---|
| CN | 1844118 A | 10/2006 |
| CN | 102477033 A | 5/2012 |

(Continued)

OTHER PUBLICATIONS

U.S. Appl. No. 16/932,072, filed Jul. 17, 2020, Crew et al.
U.S. Appl. No. 17/001,519, filed Aug. 24, 2020, Chen et al.
U.S. Appl. No. 17/359,424, filed Jun. 25, 2021, Crew et al.
U.S. Appl. No. 17/548,842, filed Dec. 13, 2021, Chen et al.
Abraham, R.T. "Phosphatidylinositol 3-kinase related kinases." Current Opinion in Immunology, 1996, 8(3), 412-418.
Ahn, D. et al. "HIF-1α peptide derivatives with modifications at the hydroxyproline residue as activators of HIF-1α." Bioorganic & Medicinal Chemistry Letters, 2009, 19(15), 4403-4405.

(Continued)

*Primary Examiner* — Jared Barsky
*Assistant Examiner* — Liyuan Mou
(74) *Attorney, Agent, or Firm* — COOLEY LLP

(57) ABSTRACT

The present disclosure relates to polymorphic forms of (S)-3-(5-(4-((1-(4-((1R,2S)-6-hydroxy-2-phenyl-1,2,3,4-tetrahydronaphthalen-1-yl)phenyl)piperidin-4-yl)methyl)piperazin-1-yl)-1- oxoisoindolin-2-yl)piperidine-2,6-dione,

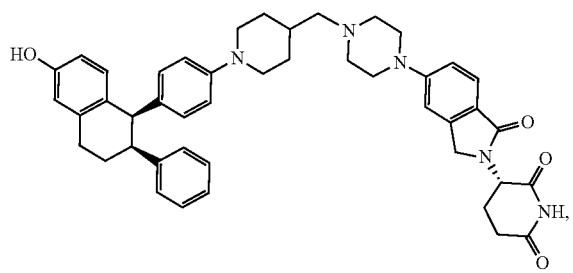

methods of making these polymorphic forms, and compositions comprising these polymorphic forms. These polymorphic forms are useful in the treatment of various diseases, including, for example, breast cancer.

6 Claims, 12 Drawing Sheets

(56) References Cited

U.S. PATENT DOCUMENTS

| | | |
|---|---|---|
| 2014/0302523 A1 | 10/2014 | Crews et al. |
| 2014/0356322 A1 | 12/2014 | Crews et al. |
| 2015/0119435 A1 | 4/2015 | Crews et al. |
| 2015/0141470 A1 | 5/2015 | Garraway et al. |
| 2015/0258080 A1 | 9/2015 | Hager et al. |
| 2015/0291562 A1 | 10/2015 | Crew et al. |
| 2015/0344473 A1 | 12/2015 | Du et al. |
| 2016/0022642 A1 | 1/2016 | Crews et al. |
| 2016/0045607 A1 | 2/2016 | Crew et al. |
| 2016/0058872 A1 | 3/2016 | Crew et al. |
| 2016/0136230 A1 | 5/2016 | Campos et al. |
| 2016/0214972 A1 | 7/2016 | Jin et al. |
| 2016/0243247 A1 | 8/2016 | Bradner et al. |
| 2016/0272639 A1 | 9/2016 | Crew et al. |
| 2016/0368911 A1 | 12/2016 | Campos et al. |
| 2017/0008904 A1 | 1/2017 | Crew et al. |
| 2017/0037004 A1 | 2/2017 | Crew et al. |
| 2017/0065719 A1 | 3/2017 | Qian et al. |
| 2017/0121321 A1 | 5/2017 | Crews et al. |
| 2017/0281784 A1 | 10/2017 | Wang et al. |
| 2017/0307614 A1 | 10/2017 | Crews et al. |
| 2017/0327469 A1 | 11/2017 | Crew et al. |
| 2017/0348298 A1* | 12/2017 | Carrancio ............ A61P 35/02 |
| 2018/0015087 A1 | 1/2018 | Liu et al. |
| 2018/0072711 A1 | 3/2018 | Crew et al. |
| 2018/0099940 A1 | 4/2018 | Crew et al. |
| 2018/0125821 A1 | 5/2018 | Crew et al. |
| 2018/0147202 A1 | 5/2018 | Crew et al. |
| 2018/0155322 A1 | 6/2018 | Crew et al. |
| 2018/0177750 A1 | 6/2018 | Crew et al. |
| 2018/0179183 A1 | 6/2018 | Crew et al. |
| 2018/0193470 A1 | 7/2018 | Crew et al. |
| 2018/0215731 A1 | 8/2018 | Crew et al. |
| 2018/0228907 A1 | 8/2018 | Crew et al. |
| 2018/0237418 A1 | 8/2018 | Crew et al. |
| 2018/0256586 A1 | 9/2018 | Crew et al. |
| 2020/0231567 A1 | 7/2020 | Man et al. |
| 2021/0060008 A1 | 3/2021 | Chen et al. |

FOREIGN PATENT DOCUMENTS

| | | | |
|---|---|---|---|
| CN | 103688176 A | 3/2014 | |
| CN | 103159736 B | 5/2015 | |
| CN | 111454248 A | 7/2020 | |
| CN | 113816927 A | 12/2021 | |
| EP | 2985285 A1 | 2/2016 | |
| EP | 3548483 A1 | 10/2019 | |
| EP | 3689868 A1 | 8/2020 | |
| JP | H10-204028 A | 8/1998 | |
| JP | 2004-525889 A | 8/2004 | |
| JP | 2010-502627 A | 1/2010 | |
| JP | 2015-508414 A | 3/2015 | |
| JP | 2020-504089 A | 2/2020 | |
| JP | 2020-100659 A | 7/2020 | |
| RU | 2008112221 A | 10/2009 | |
| RU | 2448101 C2 | 4/2012 | |
| RU | 2011121567 A | 12/2012 | |
| RU | 2487873 C2 | 7/2013 | |
| RU | 2012138709 A | 3/2014 | |
| WO | WO 1998/003502 A1 | 1/1998 | |
| WO | WO 1998/045287 A1 | 10/1998 | |
| WO | WO 1999/15521 A1 | 4/1999 | |
| WO | WO 2000/66119 A1 | 11/2000 | |
| WO | WO 2002/066512 A1 | 8/2002 | |
| WO | WO 2002/100845 A1 | 12/2002 | |
| WO | WO 2005/097791 A1 | 10/2005 | |
| WO | WO 2006/069063 A1 | 6/2006 | |
| WO | WO 2006/084015 A2 | 8/2006 | |
| WO | WO 2006/113942 A2 | 10/2006 | |
| WO | WO 2007/101347 A1 | 9/2007 | |
| WO | WO 2007/106670 A2 | 9/2007 | |
| WO | WO 2007/130626 A2 | 11/2007 | |
| WO | WO 2008/011392 A2 | 1/2008 | |
| WO | WO 2008/014236 A1 | 1/2008 | |
| WO | WO 2008/109057 A1 | 9/2008 | |
| WO | WO 2008/128121 A1 | 10/2008 | |
| WO | WO 2008/128171 A2 | 10/2008 | |
| WO | WO 2008/134679 A1 | 11/2008 | |
| WO | WO 2009/015254 A1 | 1/2009 | |
| WO | WO-2009019274 A1 * | 2/2009 | ............ C07D 401/12 |
| WO | WO 2009/060292 A2 | 5/2009 | |
| WO | WO 2010/107485 A1 | 9/2010 | |
| WO | WO 2010/141805 A1 | 12/2010 | |
| WO | WO 2011/008260 A2 | 1/2011 | |
| WO | WO-2011076786 A1 * | 6/2011 | ............ A61K 31/472 |
| WO | WO 2012/003281 A2 | 1/2012 | |
| WO | WO 2012/040527 A2 | 3/2012 | |
| WO | WO 2012/078559 A2 | 6/2012 | |
| WO | WO 2012/090104 A1 | 7/2012 | |
| WO | WO 2013/071035 A1 | 5/2013 | |
| WO | WO 2013/071039 A1 | 5/2013 | |
| WO | WO 2013/097224 A1 | 7/2013 | |
| WO | WO 2013/106643 A2 | 7/2013 | |
| WO | WO 2013/106646 A2 | 7/2013 | |
| WO | WO 2013/170147 A1 | 11/2013 | |
| WO | WO 2013/175417 A1 | 11/2013 | |
| WO | WO 2013/178570 A1 | 12/2013 | |
| WO | WO 2014/011712 A1 | 1/2014 | |
| WO | WO 2014/020502 A2 | 2/2014 | |
| WO | WO 2014/025759 A1 | 2/2014 | |
| WO | WO-2014025964 A2 * | 2/2014 | ......... A61K 31/4035 |
| WO | WO 2014/038606 A1 | 3/2014 | |
| WO | WO 2014/047024 A1 | 3/2014 | |
| WO | WO 2014/055461 A1 | 4/2014 | |
| WO | WO 2014/074658 A1 | 5/2014 | |
| WO | WO 2014/100065 A1 | 6/2014 | |
| WO | WO 2014/100071 A2 | 6/2014 | |
| WO | WO 2014/107713 A1 | 7/2014 | |
| WO | WO 2014/108452 A1 | 7/2014 | |
| WO | WO 2014/123418 A1 | 8/2014 | |
| WO | WO 2014/134201 A1 | 9/2014 | |
| WO | WO 2014/151863 A1 | 9/2014 | |
| WO | WO 2015/000867 A1 | 1/2015 | |
| WO | WO 2015/000868 A1 | 1/2015 | |
| WO | WO 2015/006524 A1 | 1/2015 | |
| WO | WO-2015092420 A1 * | 6/2015 | ............ A61K 31/437 |
| WO | WO 2015/160845 A2 | 10/2015 | |
| WO | WO 2016/097071 A1 | 6/2016 | |
| WO | WO 2016/105518 A1 | 6/2016 | |
| WO | WO 2016/118666 A1 | 7/2016 | |
| WO | WO 2016/146985 A1 | 9/2016 | |
| WO | WO 2016/149668 A1 | 9/2016 | |
| WO | WO 2016/169989 A1 | 10/2016 | |
| WO | WO 2016/172134 A2 | 10/2016 | |
| WO | WO 2016/197114 A1 | 12/2016 | |
| WO | WO 2017/011590 A1 | 1/2017 | |
| WO | WO 2017/024318 A1 | 2/2017 | |
| WO | WO 2017/024319 A1 | 2/2017 | |
| WO | WO 2017/030814 A1 | 2/2017 | |
| WO | WO 2017/046036 A1 | 3/2017 | |
| WO | WO 2017/079267 A1 | 5/2017 | |
| WO | WO 2017/160990 A1 | 9/2017 | |
| WO | WO 2017/161119 A1 | 9/2017 | |
| WO | WO 2017/185036 A1 | 10/2017 | |
| WO | WO 2017/197051 A1 | 11/2017 | |
| WO | WO 2018/098280 A1 | 5/2018 | |
| WO | WO 2018/102725 A1 | 6/2018 | |
| WO | WO-2021231174 A1 | 11/2021 | |
| WO | WO-2022056368 A1 | 3/2022 | |

OTHER PUBLICATIONS

Ali, et al. "Molecular mechanisms and mode of tamoxifen resistance in breast cancer." Bioinformation, 2016, 12(3), 135-139.

Ardecky, et al. "Design, synthesis and evaluation of inhibitor of apoptosis protein (IAP) antagonists that are highly selective for the BIR2 domain of XIAP." Bioorganic & Medicinal Chemistry Letters, 2013, 23(14), 4253-4257.

Asano, et al. "Design, stereoselective synthesis, and biological evaluation of novel tri-cyclic compounds as inhibitor of apoptosis proteins (IAP) antagonists." Bioorganic & Medicinal Chemistry, 2013, 21, 5725-5737.

(56) References Cited

OTHER PUBLICATIONS

Bargagna-Mohan, et al. "Use of PROTACS as molecular probes of angiogenesis." Bioorg Med Chem Lett., Jun. 2, 2005, 15(11), 2724-2727.
Battista, M. J. et al. "Fulvestrant for the treatment of endometrial cancer." Expert Opinion on Investigational Drugs, 2016, 25(4), 475-483.
Beaver, et al., "FDA Approval: Palbociclib for the Treatment of Postmenopausal Patients with Estrogen Receptor-Positive, HER2-Negative Metastatic Breast Cancer," Clin Cancer Res., Nov. 1, 2015, 21(21), 4760-4766.
Bondeson, et al. "Targeted Protein Degradation by Small Molecules." Annu Rev Pharmacol Toxicol., Jan. 6, 2017, 57, 107-123.
Bondeson, et al. "Catalytic in vivo protein knockdown by small-molecule PROTACS." National Chem Biol. Aug. 2015, 11(8), 611-617.
Buckley, et al. "HaloPROTACS: Use of Small Molecule PROTACS to Induce Degradation of HaloTag Fusion Proteins." ACS Chem Biol., Aug. 21, 2015, 10(8), 1831-1837.
Buckley, et al. "Small Molecule Inhibitors of the Interaction Between the E3 Ligase VHL and HIF1α." Angew Chem Int Ed Engl., Nov. 12, 2012, 51(46), 11463-11467.
Buckley, et al., "Targeting the von Hippel-Lindau E3 ubiquitin ligase using small molecules to disrupt the VHL/HIF-1α interaction", Journal of the American Chemical Society, Feb. 27, 2012, 134(10), 4465-4468.
Burke, et al. "Design, Synthesis and Biological Evaluation of Doxorubicin-Formaldehyde Conjugates Targeted to Breast Cancer Cells." J. Med. Chem., 2004, 47(5), 1193-1206.
Burslem, et al., "Small-Molecule Modulation of Protein Homeostasis." Chem Rev., Aug. 4, 2017, 117(17), 11269-11301.
Byrn, et al., "Pharmaceutical Solids: A Strategic Approach to Regulatory Considerations," Pharmaceutical Research, 1995, 12(7), 945-954.
Capitosti, et al. "Thalidomide analogues demonstrate dual inhibition of both angiogenesis and prostate cancer." Bioorganic & Medicinal Chemistry, 2004, 12, 327-336.
Carmony KC, et al. "PROTAC-Induced Proteolytic Targeting." Methods Mol. Biol., 2012, 832, 627-638.
CAS Registry No. 1004933-70-3, which entered STN on Feb. 21, 2008.
CAS Registry No. 871986-52-6 entered STN Jan. 16, 2006.
Chéne, et al. "Inhibiting the p53-MDM2 interaction: an important target for cancer therapy." Nat. Rev. Cancer, Feb. 2003, 3, 102-109.
Cheng-Gen, et al. "Progress in Antiestrogens for the Treatment of Breast Cancer." Chinese Journal of New Drugs, Dec. 31, 2006, 15(13), 1051-1057.
Cohen, et al. "Orally Bioavailable Antagonists of Inhibitor of Apoptosis Proteins Based on an Azabicyclooctane Scaffold." J. Med. Chem., 2009, 52, 1723-1730.
Cohen, et al. "Antagonists of inhibitors of apoptosis proteins based on thiazole amide isosteres." Bioorganic & Medicinal Chemistry Letters, 2010, 20, 2229-2233.
Connor, et al. "Circumventing Tamoxifen Resistance in Breast Cancers using Antiestrogens that Induce Unique Conformational Changes in the Estrogen Receptor." Cancer Res., Apr. 1, 2001, 61, 2917-2922.
Contino-Pépin, et al. "Preliminary biological evaluations of new thalidomide analogues for multiple sclerosis application," Bioorganic & Medicinal Chemistry Letter, 2009, 19, 878-881.
Corson, et al., "Design and applications of bifunctional small molecules: Why two heads are better than one," ACS Chemical Biology, Nov. 21, 2008, 3(11), 677-692.
Crews, C.M., "Targeting the Undruggable Proteome: The Small Molecules of my Dreams." Chemistry & Biology, Jun. 25, 2010, 17, 551-555.
Cromm, et al., "Targeted Protein Degradation: from Chemical Biology to Drug Discovery." Cell Chemical Biology, Sep. 21, 2017, 24(9), 1181-1190.

Cyrus, et al. "Jostling for Position: Optimizing Linker Location in the Design of Estrogen Receptor-targeting PROTACs." Chem Med Chem., Jul. 5, 2010, 5(7), 979-985.
Cyrus, K. et al, "Impact of linker length on the activity of PROTACs," Mol. Biosyst., Feb. 2011, 7(2), 359-364 (15 pages total).
Cyrus, K. et al, "Two-Headed PROTAC: An effective New Tool for Targeted Protein Degradation," Chembiochem., Jul. 26, 2010, 11(11), 1531-1534 (9 pages total).
Deroo, et al. "Estrogen receptors and human disease." The Journal of Clinical Investigation, Mar. 2006, 116(3), 561-570.
Di, et al. "Reactivation of p53 by Inhibiting Mdm2 E3 Ligase: A Novel Antitumor Approach." Current Cancer Drug Targets, 2011, 11, 987-994.
Ding, et al. "Discovery of RG7388, a Potent and Selective p53-MDM2 Inhibitor in Clinical Development." J Med Chem., Jun. 28, 2013, 56, 5979-5983.
Dixon, et al., "Identifying Druggable Disease-Modifying Gene Products." Curr Opin Chem Biol, Dec. 2009, 13(5-6), 549-555.
Fischer, et al. "Structure of the DDB1-CRBN E3 ubiquitin ligase in complex with thalidomide." Nature, 2014, 512, 49-53.
Flygare, et al. "Small-molecule pan-IAP antagonists: a patent review." Expert Opin. Ther. Pat., 2010, 20(2), 251-267.
Gadd, et al. "Structural basis of PROTAC cooperative recognition for selective protein degradation." Nat Chem Biol., May 2017, 13(5), 514-521.
Galdeano, et al. "Structure-Guided Design and Optimization of Small Molecules Targeting the Protein-Protein Interaction between the von Hippel-Lindau (VHL) E3 Ubiquitin Ligase and the Hypoxia Inducible Factor (HIF) Alpha Subunit with in Vitro Nanomolar Affinities." Journal Med Chem, Aug. 28, 2014, 57, 8657-8663.
Garner, et al. "RAD1901: a novel, orally bioavailable selective estrogen receptor degrader that demonstrates antitumor activity in breast cancer xenograft models." Anticancer Drugs, 2015, 26, 948-956.
Golub, et al. "Molecular Classification of Cancer: Class Discovery and Class Prediction by Gene Expression Monitoring." Science, Oct. 15, 1999, 286, 531-537.
Gosink, et al. "Redirecting the specificity of ubiquitination by modifying ubiquitin—conjugating enzymes." Pro. Natl. Acad Sci, Sep. 1995, 92, 9117-9121.
Hansen, et al., "Potent and selective pyrazole-based inhibitors of B-Raf kinase", Bioorganic & Medicinal Chemistry Letters, 2008, 18(16), 4692-4695.
Haupt, et al. "Mdm2 promotes the rapid degradation of p53." Nature, May 15, 1997, 387, 296-299.
Heldring, et al. "Estrogen Receptors: How Do They Signal and What are Their Targets." Physiological Reviews, 2007, 87, 905-931.
Hennessy, et al. "Discovery of aminopiperidine-based Smac mimetics as IAP antagonists." Bioorganic & Medicinal Chemistry Letters, 2012, 22, 1690-1694.
Hines, et al. "Posttranslational protein knockdown coupled to receptor tyrosine kinase activation with phosphoPROTACs." Proc Natl Acad Sci USA, May 28, 2013, 110(22), 8942-8947.
Hird, et al. "Structure-based design and synthesis of tricyclic IAP (Inhibitors of Apoptosis Proteins) inhibitors." Bioorganic Medicinal Chemistry Letters, 2014, 24, 1820-1824.
Hoffmann, et al. "Characterization of New Estrogen Receptor Destabilizing Compounds: Effects on Estrogen-Sensitive and Tamoxifen-Resistant Breast Cancer." Journal of the National Cancer Institute, Feb. 4, 2004, 96(3), 210-218.
Hon, et al. "Structural basis for the recognition of hydroxyproline in HIF-1α by pVHL." Nature, Jun. 27, 2002, 417, 975-978.
Huang, et al. "Drugging the undruggables: exploring the ubiquitin system for drug development." Cell Research, 2016, 26, 484-498.
Hughes, et al. "Molecular recognition of ternary complexes: a new dimension in the structure-guided design of chemical degraders." Essays in Biochemistry, 2017, 61, 505-516.
Ivan, et al. "HIFα Targeted for VHL-Mediated Destruction by Proline Hydroxylation: Implications for O₂ Sensing." Science, Apr. 20, 2001, 292, 464-468.
Jang, et al. "Targeted Degradation of Proteins by PROTACs." Curr. Protoc. Chem. Biol., Apr. 2010, 2, 71-87.

(56) References Cited

OTHER PUBLICATIONS

Jiang, et al. "Synthesis of 7alpha-substituted derivatives of 17beta-estradiol." Steroids, May 2006, 71(5), 334-342. (Abstract only.).
Jordan, et al. "A monohydroxylated metabolite of tamoxifen with potent antioestrogenic activity." Endocrinol, 1977, 75, 305-316.
Kim, "Discovery of tetrahydroisoquinoline-based bivalent heterodimeric IAP antagonists." Bioorganic & Medicinal Chemistry Letters, 2014, 24, 5022-5029.
Knott, Edward (1955). "Compounds containing sulphur chromophores. Part I. The action of bases on heterocyclic sulphide quarternary salts", Journal of the Chemical Society (resumed). 10.1039/jr9550000916. 949-954) (USPTO summary attached).
Kronke, et al. "Lenalidomide Causes Selective Degradation of IKZF1 and IKZF3 in Multiple Myeloma Cells." Science, Jan. 17, 2014, 343(6168), 301-305 (11 pages total).
Lai, et al. "Identification of GDC-0810 (ARN-810), an Orally Bioavailable Selective Estrogen Receptor Degrader (SERD) that Demonstrates Robust Activity in Tamoxifen-Resistant Breast Cancer Xenografts." Journal of Medicinal Chemistry, Apr. 16, 2015, 58, 4888-4904.
Lai, et al. "Modular PROTAC Design for the Degradation of Oncogenic BCR-ABL." Angew Chem Int Ed Engl., Jan. 11, 2016, 55(2), 807-810.
Lai, et al. "Induced protein degradation: an emerging drug discovery paradigm." Nat Rev Drug Discov., Feb. 2017, 16(2), 101-114.
Lala, et al. "Role of nitric oxide in tumor progression: Lessons from experimental tumors", Cancer and Metastasis Reviews, 1998, 17, 91-116.
Lebraud, et al. "Protein Degradation by In-Cell Self-Assembly of Proteolysis Targeting Chimeras." ACS Central Science, Dec. 5, 2016, 2, 927-934.
Lee, et al. "Targeted Degradation of the Aryl Hydrocarbon Receptor by the PROTAC Approach: A Useful Chemical Genetic Tool." ChemBioChem., Nov. 23, 2007, 8, 2058-2062.
Levine, et al. "Targeting the Androgen Receptor with Steroid Conjugates." Journal of Medicinal Chemistry, Jun. 17, 2014, 57, 8224-8237.
Li, et al. "Single Polymer-drug Conjugate Carrying Two Drugs for Fixed-dose Co-delivery." Medicinal Chemistry, 2014, 4(10), 676-683.
Liu, et al. "Bioactivation of the Selective Estrogen Receptor Modulator Desmethylated Arzoxifene to Quinoids: 4'-Fluoro Substitution Prevents Quinoid Formation", Chem. Res. Toxicol. 2005, 18, 162-173.
Liu, et al. "Design and biological characterization of hybrid compounds of curcumin and thalidomide for multiple myeloma." Org. Biomol. Chem., 2013, 11, 4757-4763.
Lopez-Girona, et al. "Cereblon is a direct protein target for immunomodulatory and antiproliferative activities of lenalidomide and pomalidomide," Leukemia, 2012, 26, 2326-2335.
Lu, et al. "Hijacking the E3 Ubiquitin Ligase Cereblon to Efficiently Target BRD4." Chemistry & Biology, 22, Jun. 18, 2015, 755-763.
Lu, et al. "The Myeloma Drug Lenalidomide Promotes the Cereblon-dependent destruction of Ikaros Proteins." Science, Jan. 17, 2014, 343(6168), 305-309.
Mahalingam, et al. "Targeting HSP90 for cancer therapy." British Journal of Cancer, 2009, 100, 1523-1529.
Maniaci, et al. "Homo-PROTACs: bivalent small-molecule dimerizers of the VHL E3 ubiquitin ligase to induce self-degradation." Nat Commun., 2017, 8(1), 830, 1-13.
Mannhold, et al. "IAP antagonists: promising candidates for cancer therapy." Drug Discovery Today, Mar. 2010, 15(5-6), 210-219.
Maximov, et al. "The Discovery and Development of Selective Estrogen Receptor Modulators (SERMs) for Clinical Practice." Curr Clin Pharmacol. 2013, 8(2), 135-155.
Mcguire, et al. "Taxol: A Unique Antineoplastic Agent with Significant Activity in Advanced Ovarian Epithelial Neoplasms." Ann. Intern. Med., 1989, 111, 273-279.
Medline Plus Trusted Health Information for You, <www.nlm.nih.gov/medlineplus/cancer.html>., 2007, 1-10.
Min, et al. "Structure of an HIF-1-$\alpha$-pVHL Complex: Hydroxyproline Recognition in Signaling." Science, 2002, 296, 1886-1889.
Miyazaki, et al. "Discovery of DS-5272 as a promising candidate: A potent and orally active p53-MDM2 interaction inhibitor." Bioorganic & Medicinal Chemistry, 2015, 23, 2360-2367.
Muller, et al. "Amino-Substituted Thalidomide Analogs: Potent Inhibitors of TNF-$\alpha$ Production." Bioorganic & Medicinal Chemistry Letters, 1999, 9, 1625-1630.
Ndubaku, et al. "Antagonism of c-IAP and XIAP Proteins is Required for Efficient Induction of Cell Death by Small-Molecule IAP Antagonists." ACS Chem Biol., 2009, 4(7), 557-566.
Neklesa, et al. "Chemical biology: Greasy tags for protein removal." Nature, Jul. 19, 2012, 487, 308-309.
Neklesa, "Targeted protein degradation by PROTACs." Pharmacology & Therapeutics, 2017, 174, 138-144.
Nikolovska-Coleska, et al. "Interaction of a Cyclic, Bivalent Smac Mimetic with the X-Linked Inhibitor of Apoptosis Protein." Biochemistry, Sep. 16, 2008, 47(37), 9811-9824.
Notice of Grounds of Rejection for JP Application No. 2020-033150, filing date of Oct. 11, 2017, dated Aug. 18, 2020, English Translation, 1-4.
Office Action and Prior Art Search Report for RU Application No. 2020106142, filing date of Dec. 1, 2017, dated Aug. 7, 2020, English Translation, 7 pages.
Ohoka, et al. "SNIPER(TACC3) induces cytoplasmic vacuolization and sensitizes cancer cells to Bortezomib." Cancer Science, Mar. 2017, 108(5), 1032-1041.
Ohoka, et al. "In Vivo Knockdown of Pathogenic Proteins via Specific and Nongenetic Inhibitor of Apoptosis Protein (IAP)-dependent Protein Erasers (SNIPERs)." Journal of Biological Chemistry, Mar. 17, 2017, 292(11), 4556-4570.
Oost, et al. "Discovery of Potent Antagonists of the Antiapoptotic Protein XIAP for the Treatment of Cancer." Journal of Medicinal Chemistry, 2004, 47, 4417-4426.
Ottis, et al. "Assessing Different E3 Ligases for Small Molecule Induced Protein Ubiquitination and Degradation." ACS Chem Biol, Aug. 2, 2017, 12, 2570-2578.
Ottis, et al. "Proteolysis-Targeting Chimeras: Induced Protein Degradation as a Therapeutic Strategy." ACS Chem Biol., Mar. 6, 2017, 12, 892-898.
Perez. "Discovery of Potent Heterodimeric Antagonists of Inhibitor of Apoptosis Proteins (IAPs) with Sustained Antitumor Activity." Journal of Medical Chemistry, Jan. 13, 2015, 58, 1556-1562.
Poutiainen, et al. "Design, Synthesis, and Biological Evaluation of Nonsteroidal Cycloalkane[d]isoxazole-Containing Androgen Receptor Modulators." Journal of Medicinal Chemistry, Jul. 2, 2012, 55, 6316-6327.
Puppala, et al. "Development of an Aryl Hydrocarbon Receptor Antagonist Using the Proteolysis-Targeting Chimeric Molecules Approach: A Potential Tool for Chemoprevention." Mol. Pharmacol., 2008, 73, 1064-1071.
Qin, et al. "Benzothiophene Selective Estrogen Receptor Modulators with Modulated Oxidative Activity and Receptor Affinity", J. Med Chem, 2007, 50, 2682-2692.
Raina, et al. "Targeted protein knockdown using small molecule degraders." Current Opinion in Chemical Biology, 2017, 39, 46-53.
Raina, et al. "PROTAC-induced BET protein degradation as a therapy for castration-resistant prostate cancer." Proc Natl Acad Sci USA, Jun. 28, 2016, 113(26), 7124-7129.
Remillard, et al. "Degradation of the BAF Complex Factor BRD9 by Heterobifunctional Ligands." Angew Chem Int Ed Engl., May 15, 2017, 56(21), 5738-5743.
Rew, et al. "Discovery of AM-7209, a Potent and Selective 4-Amidobenzoic Acid Inhibitor of the MDM2-p53 Interaction." Journal of Medicinal Chemistry, Nov. 10, 2014, 57, 10499-10511.
Robertson, "Fulvestrant (Faslodex®)—How to Make a Good Drug Better." Oncologist, 2007,12, 774-784.
Rodriguez-Gonzalez, et al. "Targeting steroid hormone receptors for ubiquitination and degradation in breast and prostate cancer." Oncogene., Dec. 4, 2008, 27, 7201-7211.
Rotili, et al. "Photoactivable peptides for identifying enzyme-substrate and protein-protein interactions." Chem Commun (Camb), 2011, 47, 1488-1490.

(56) References Cited

OTHER PUBLICATIONS

Ruchelman, et al. "Isosteric analogs of lenalidomide and pomalidomide: Synthesis and biological activity." Bioorganic & Medicinal Chemistry Letters, 2013, 23, 360-365.
Sakamoto, et al. "Development of Protacs to Target Cancer-promoting Proteins for Ubiquitination and Degradation." Molecular & Cellular Proteomics., 2003, 2(12), 1350-1358.
Sakamoto, et al. "Protacs: Chimeric Molecules that target proteins to the Skp1-Cullin-F box complex for ubiquitination and degradation." Proc Natl Acad Sci USA, Jul. 17, 2001, 98(15), 8554-8559.
Salami, et al. "Waste disposal—An attractive strategy for cancer therapy." Science, Mar. 17, 2017, 355, 1163-1167.
Schiedel, et al. "Chemically Induced Degradation of Sirtuin 2 (Sirt2) by a Proteolysis Targeting Chimera (PROTAC) Based on Sirtuin Rearranging Ligands (SirReals)." Journal of Medicinal Chemistry, Apr. 5, 2017, 61, 482-491.
Schneekloth, et al. "Chemical Genetic Control of Protein Levels: Selective in Vivo Targeted Degradation." J Am Chem Soc., 2004, 126(12), 3748-3754.
Schneekloth, et al. "Targeted intracellular protein degradation induced by a small molecule: En route to chemical proteomics." Bioorganic & Medicinal Chemistry Letters, 2008, 18, 5904-5908.
Scott, et al. "Tetrahydroisoquinoline Phenols: Selective Estrogen Receptor Downregulator Antagonists with Oral Bioavailability in Rat." ACS Medicinal Chemistry Letters, Dec. 19, 2015, 6, 7, 94-99.
Smith, et al. "Targeted Intracellular Protein Degradation Induced by a Small Molecule: En Route to Chemical Proteomics." Bioorg Med Chem Lett., Nov. 15, 2008, 18(22), 5904-5908.
Stewart, et al. "Efforts toward elucidating Thalidomide's molecular target: An expedient synthesis of the first Thalidomide Biotin Analogue." Organic and Biomolecular Chemistry, 2010, 8, 4059-4062.
STN transcript excerpt "Compounds containing sulfur Chromophores v. Complex cyanines." Nov. 24, 2017, 1 page.
Stoppler, Melissa Conrad., Endometriosis [online], "Endometriosis Definition and Facts" URL http://www.medicinenet.com/endometriosis/article.htm, retrieved on Apr. 5, 2017, 1-7.
Stoppler, Melissa Conrad., Endometriosis [online], "What about surgery for Endometriosis?" URL http://www.medicinenet.com/endometriosis/article.htm, retrieved on Apr. 5, 2017, 1-7.
Suh, N. et al. "Arzoxifene, a New Selective Estrogen Receptor Modulator for Chemoprevention of Experimental Breast Cancer." Cancer Res., Dec. 1, 2001, 61, 8412-8415.
Sun, et al. "Discovery of AMG 232, a Potent, Selective, and Orally Bioavailable MDM2-p53 Inhibitor in Clinical Development", Journal of Medicinal Chemistry, Jan. 23, 2014, Epub Feb. 5, 2014, 57, 1454-1472.
Sun, et al. "Potent bivalent Smac Mimetics: Effect of the Linker on Binding to Inhibitor of Apoptosis Proteins (IAPs) and Anticancer Activity", J. Med. Chem., Apr. 4, 2011, 54, 3306-3318.
Toure, et al. "Small-Molecule PROTACS: New Approaches to Protein Degradation." Angew Chem Int Ed Engl., 2016, 55, 1966-1973.
Trewartha, et al. "Advances in prostate cancer treatment." Nat Rev Drug Discovery., Nov. 2013, 12, 823-824.
Turk, "Binding of thalidomide to $\alpha_1$-acid glycoprotein may be involved in its inhibition of tumor necrosis factor a production." Proc. Natl. Acad. Sci. USA, Jul. 1996, 93, 7552-7556.
Vamos, et al. "Expedient Synthesis of Highly Potent Antagonists of Inhibitor of Apoptosis Proteins (IAPs) with Unique Selectivity for ML-IAP." ACS Chem. Biol., Apr. 19, 2013, 8(4), 725-732.
Van Molle, et al. "Dissecting Fragment-Based Lead Discovery at the von Hippel-Lindau Protein: Hypoxia Inducible Factor 1α Protein-Protein Interface." Chemistry & Biology, Oct. 26, 2012, 19, 1300-1312.
Vassilev, et al. "In Vivo Activation of the p53 Pathway by Small-Molecule Antagonists of MDM2." Science, Feb. 6, 2004, 303, 844-848.
Vazquez, et al. "The genetics of the p53 pathway, apoptosis and cancer therapy." Nature Reviews Drug Discovery, Dec. 2008, 7, 979-982.
Vu, et al. "Discovery of RG7112: A Small-Molecule MDM2 Inhibitor in Clinical Development." ACS Medicinal Chemistry Letters, 2013, 4, 466-469.
Wang, et al. "Discovery of Novel Second Mitochondrial-Derived Activator of Caspase Mimetics as Selective Inhibitor or Apoptosis Protein Inhibitors." J. Pharmacol. Exp. Ther., May 2014, 349, 319-329.
Wang, et al. "Estrogen Induces c-myc Gene Expression via an Upstream Enhancer Activated by the Estrogen Receptor and the AP-1 Transcription Factor." Mol. Endocrinol., Sep. 2011, 25(9), 1527-1538.
Wang, et al. "Small-Molecule Inhibitors of the MDM2-p53 Protein-Protein Interaction (MDM2 inhibitors) in Clinical Trials for Cancer Treatment." Journal of Medical Chemistry, Nov. 14, 2014, 58, 1038-1052.
Wang, et al. "Temporal activation of p53 by a specific MDM2 inhibitor is selectively toxic to tumors and leads to complete tumor growth inhabitation", PNAS USA, Mar. 11, 2008, 105(10), 3933-3938.
Weir, et al. "AZD9496: An Oral Estrogen Receptor Inhibitor that Blocks the Growth of ER-Positive and ESR1-Mutant Breast Tumors in Preclinical Models." Cancer Res., 2016, 76, 3307-3318.
Wijayaratne, et al. "The Human Estrogen Receptor-α is a Ubiquitinated Protein Whose Stability is Affected Differentially by Agonists, Antagonists, and Selective Estrogen Receptor Modulators." The Journal of Biological Chemistry, Sep. 21, 2001, 276(38), 35684-35692.
Willson, et al. "3-[4-(1,2—Diphenylbut-1-enyl)phenyl]acrylic Acid: A Non-Steroidal Estrogen with Functional Selectivity for Bone over Uterus in Rats." Journal of Medicinal Chemistry, 1994, 37, 1550-1552.
Winter, et al. "Phthalimide Conjugation as a strategy for in vivo target protein degradation." Science, Jun. 19, 2015, 348(6241), 1376-1381.
Yu, et al., "The mechanism of tamoxifen in breast cancer prevention." Breast Cancer Research, 2001, 3(1), A74, 2001, 1-22.
Zengerle, et al. "Selective Small Molecule Induced Degradation of the BET Bromodomain Protein BRD4." ACS Chemical Biology, Jun. 2, 2015, 10, 1770-1777.
Zhang, et al. "Small-molecule MDM2-p53 inhibitors: recent advances." Future Medicinal Chemistry, 2015, 7(5), 631-645.
Zhang, et al. "Targeted Degradation of Proteins by Small Molecules: A Novel Tool for Functional Proteomics." Combinational Chemistry & High Throughput Screening, 2004, 7(7), 689-697.
Zhong, et al. "Modulation of Hypoxia-inducible Factor 1α Expression by the Epidermal Growth Factor/Phosphatidylinositol 3-Kinase/PTEN/AKT/FRAP Pathway in Human Prostate Cancer Cells: Implications for Tumor Angiogenesis and Therapeutics." Cancer Res, Mar. 15, 2000, 60(6), 1541-1545.
Zhou, et al. "Discovery of a Small-Molecule Degrader of Bromodomain and Extra-Terminal (BET) Proteins with Picomolar Cellular Potencies and Capable of Achieving Tumor Regression." Journal of Medicinal Chemistry, 2018, 61(2), 462-481.
Garrido, J., "Influencia de los agentes exteriores sobre la forma de los cristales", Forma y estructura de los cristales, Exedra (1973); Chapter V: 204-225; 34 pages with English Translation.
Giron, D., "Thermal analysis and calorimetric methods in the characterisation of polymorphs and solvates", Thermochimica Acta (1995); 248: 1-59.
Guranda, D. T., et al., "Preparation of Drug Polymorphs (A Review)", Khim. Farm. Zhurnal (2010); 44(5): 22-28; 7 pages with English Abstract.
Lien, E. J., "Atomic and Molecular Structure and the States of Matter", Remington's Pharmaceutical Sciences, 16th Edition (1980); pp. 160-181.
Nies, A. S., et al., "Principles of Therapeutics", Goodman & Gilman's the Pharmacological Basis of Therapeutics (copyright 1996); 9th Edition, Chapter 3; pp. 43-62.

(56) References Cited

OTHER PUBLICATIONS

Flanagan, J., et al., "ARV-471, an oral estrogen receptor PROTAC™ protein degrader for breast cancer", Arvinas meeting poster, San Antonio Breast Cancer Symposium (Dec. 4-8, 2018); 1 page.

Flanagan, J., et al., "Identification of Oral Estrogen Receptor PROTAC Degraders for Breast Cancer", Arvinas meeting poster, San Antonio Breast Cancer Symposium (Dec. 5-9, 2017); 1 page.

Snyder, L. B., "The Discovery of ARV-471, an Orally Bioavailable Estrogen Receptor Degrading PROTAC® for the Treatment of Patients with Breast Cancer", AACR Annual Meeting 2021 (Apr. 10-15, 2021 and May 17-21, 2021) [online] https://ir.arvinas.com/static-files/7a4db470-3d7f-4d4b-98a4-481b8c573169; 16 pages.

\* cited by examiner

CRYSTALLINE AND AMORPHOUS FORMS OF A COMPOUND FOR THE TARGETED DEGRADATION OF ESTROGEN RECEPTOR

CROSS-REFERENCE TO RELATED APPLICATIONS

This application claims priority to, and benefit of, U.S. Provisional Application No. 63/078,225, filed Sep. 14, 2020, the contents of which is incorporated by reference in its entirety.

BACKGROUND

Most small molecule drugs bind to enzymes or receptors in tight and well-defined pockets. In contrast, protein-protein interactions are notoriously difficult to target using small molecules due to their large contact surfaces and the shallow grooves or flat interfaces typically involved. E3 ubiquitin ligases confer substrate specificity for ubiquitination, and therefore are attractive therapeutic targets due to their specificity for certain protein substrates. The development of ligands of E3 ligases has proven challenging, in part because they must disrupt protein-protein interactions. However, recent developments have provided specific ligands which bind to these ligases. For example, since the discovery of nutlins, the first small molecule E3 ligase inhibitors, additional compounds have been reported that target E3 ligases.

One E3 ligase with particular therapeutic potential is cereblon, a protein that in humans is encoded by the CRBN gene. CRBN orthologs are highly conserved from plants to humans, indicating its physiological importance. Cereblon forms an E3 ubiquitin ligase complex with damaged DNA binding protein 1 (DDB1), Cullin-4A (CUL4A), and regulator of cullins 1 (ROC1). This complex ubiquitinates several other proteins. Through a mechanism not yet completely elucidated, cereblon ubiquitination of target proteins results in increased levels of fibroblast growth factor 8 (FGF8) and fibroblast growth factor 10 (FGF10). FGF8, in turn, regulates several developmental processes, such as limb and auditory vesicle formation. The net result is that this ubiquitin ligase complex is important for limb outgrowth in embryos. In the absence of cereblon, DDB1 forms a complex with DDB2, which functions as a DNA damage-binding protein.

Thalidomide, which has been approved for the treatment of a number of immunological indications, has also been approved for the treatment of certain neoplastic diseases, including multiple myeloma. In addition, thalidomide and several of its analogs are currently under investigation for use in treating a variety of other types of cancer. While the precise mechanism of thalidomide's anti-tumor activity is still emerging, it is known to inhibit angiogenesis. Recent literature discussing the biology of the imides includes Lu et al. Science 343, 305 (2014) and Kroenke et al. Science 343, 301 (2014).

Significantly, thalidomide and its analogs, e.g. pomalidomide and lenalidomide, are known to bind cereblon, and to alter the specificity of the complex to induce the ubiquitination and degradation of Ikaros (IKZF1) and Aiolos (IKZF3), which are transcription factors essential for multiple myeloma growth. Indeed, higher expression of cereblon has been linked to an increase in efficacy of imide drugs in the treatment of multiple myeloma.

The estrogen receptor (ER) is a member of the nuclear hormone receptor family and functions as a ligand-activated transcription factor involved with the up and down regulation of gene expression. The natural hormone for the ER is 17-beta-estradiol (E2) and closely related metabolites. Binding of estradiol to the ER causes a dimerization of the receptor and the dimer in turn binds to estrogen response elements (EREs) on DNA. The ER-DNA complex recruits other transcription factors responsible for the transcription of DNA downstream from the ERE into mRNA, which is eventually translated into protein. Alternatively, the interaction of ER with DNA may be indirect through the intermediacy of other transcription factors, most notably fos and jun. Since the expression of a large number of genes is regulated by the ER and since the ER is expressed in many cell types, modulation of the ER through binding of either natural hormones or synthetic ER ligands can have profound effects on the physiology and pathophysiology of the organism.

A variety of diseases have their etiology and/or pathology mediated by the ER. Collectively these diseases are called estrogen-dependent diseases. Estrogens are critical for sexual development in females. In addition, estrogens play an important role in maintaining bone density, regulation of blood lipid levels, and appear to have neuroprotective effects. Consequently, decreased estrogen production in post-menopausal women is associated with a number of diseases such as osteoporosis, atherosclerosis, depression and cognitive disorders. Conversely, certain types of proliferative diseases such as breast and uterine cancer and endometriosis are stimulated by estrogens and therefore anti-estrogens (i.e. estrogen antagonists) may have utility in the prevention and treatment of these types of disorders.

There are two different forms of the ER, usually referred to as $\alpha$ and $\beta$, each encoded by a separate gene (ESR1 and ESR2, respectively). Both ERs are widely expressed in different tissue types, but there are some notable differences in their expression patterns. The ER$\alpha$ is found in endometrium, breast cancer cells, ovarian stroma cells, and the hypothalamus. In males, ER$\alpha$ protein is found in the epithelium of the efferent ducts. The expression of the ER$\beta$ protein has been documented in kidney, brain, bone, heart, lungs, intestinal mucosa, prostate, and endothelial cells. Development of selective ligands for one form or the other may therefore preserve the beneficial aspects of estrogen.

Breast cancer is the most common malignancy to affect women, and the incidence of the disease is increasing worldwide. Estrogens, in particular, act as endocrine growth factors for at least one-third of breast cancers, and depriving the tumor of this stimulus is a recognized therapy for advanced disease in premenopausal women. This is achieved by the ablation of ovarian function through surgical, radiotherapeutic, or medical means and, in postmenopausal women, by the use of aromatase inhibitors.

An alternative approach to estrogen withdrawal is to antagonize estrogen with anti-estrogens. These are drugs that bind to and compete for ER present in estrogen-responsive tissues. Conventional non-steroidal anti-estrogens, such as tamoxifen, compete efficiently for ER binding, but their effectiveness is often limited by the partial agonism they display, which results in an incomplete blockade of estrogen-mediated activity. A specific or "pure" anti-estrogen with high affinity for ER and without any agonist effect may have advantages over conventional non-steroidal anti-estrogens in the treatment of estrogen-dependent disease. Fulvestrant is the first of a new class of potent pure anti-estrogens and is completely free of the partial agonist, estrogen-like activity, associated with currently available anti-estrogens like tamoxifen.

As such, there is a need for other approaches to antagonize the ER. One approach would be to develop selective ER down regulators or degraders that reduce ER expression at either the transcript or protein level.

SUMMARY

The compound made and used according to the present invention is (S)-3-(5-(4-((1-(4-(((1R,2S)-6-hydroxy-2-phenyl-1,2,3,4-tetrahydronaphthalen-1-yl)phenyl)piperidin-4-yl)methyl)piperazin-1-yl)-1-oxoisoindolin-2-yl)piperidine-2,6-dione (Compound A), having the molecular formula of $C_{45}H_{49}N_5O_4$ and with the following structural formula:

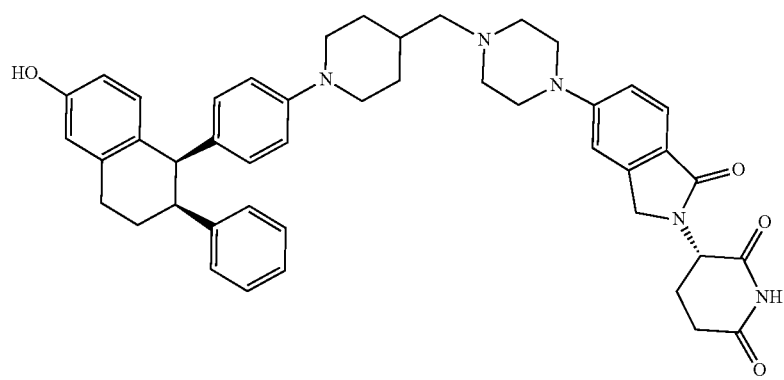 [SMILES: O=C1CC[C@H](N2Cc3cc(N4CCN(CC5CCN(c6ccc([C@@H]7c8ccc(O)cc8CC[C@@H]7c7ccccc7)cc6)CC5)CC4)ccc3C2=O)C(=O)N1]

Compound A is under development as a PROTAC® protein degrader that targets estrogen receptor (ER) for the potential treatment of breast cancer. Compound A has been shown to be a useful modulator of targeted protein ubiquitination and degradation via the ubiquitin-proteasome pathway.

The present disclosure provides several crystalline forms (polymorphs) and an amorphous form of Compound A.

In one aspect, the present disclosure provides a polymorph ("Form I") of Compound A characterized by an X-ray powder diffraction pattern including peaks at about 13.9°2θ, about 16.4°2θ, and about 17.9°2θ using Cu Kα radiation at an x-ray wavelength of 1.5406 Å.

In one aspect, the present disclosure provides a polymorph ("Form II") of Compound A characterized by an X-ray powder diffraction pattern including a peak at about 10.0°2θ, about 16.3°2θ and about 17.5°2θ using Cu Kα radiation at an x-ray wavelength of 1.5406 Å.

In one aspect, the present disclosure provides a polymorph ("Form III") of Compound A characterized by an X-ray powder diffraction pattern including a peak at about 8.8°2θ, about 10.7°2θ and 18.2°2θ using Cu Kα radiation at an x-ray wavelength of 1.5406 Å.

In one aspect, the present disclosure provides a polymorph ("Form IV") of Compound A characterized by an X-ray powder diffraction pattern including peaks at about 10.5°2θ, about 14.5°2θ, and about 16.9°2θ at an x-ray wavelength of 1.5406 Å.

In another aspect, the present disclosure provides a method of treating a disease or disorder in a subject in need thereof, comprising administering to the subject a therapeutically effective amount of a polymorph and/or amorphous form of Compound A. In some embodiments, the disease or disorder is associated with ER activity, overactivity, constitutive activity, expression, overexpression, or accumulation and aggregation. In some embodiments, the disease or disorder is associated with ER activity. In some embodiments, the disease or disorder is associated with ER overactivity. In some embodiments, the disease or disorder is associated with ER constitutive activity. In some embodiments, the disease or disorder is associated with ER expression. In some embodiments, the disease or disorder is associated with ER overexpression. In some embodiments, the disease or disorder is associated with ER accumulation and aggregation.

In some embodiments, the disease or disorder is cancer or a neoplasia associated with ER activity, overactivity, constitutive activity, expression, overexpression, or accumulation and aggregation. In some embodiments, the disease or disorder is breast cancer, ovarian cancer, endometrial cancer or uterine cancer. In some embodiments, the disease or disorder is endometriosis.

In another aspect, the present disclosure provides a pharmaceutical composition comprising a therapeutically effective amount of a polymorph and/or amorphous form of Compound A wherein the composition is effective in treating or ameliorating at least one symptom of the disease or disorder. In some embodiments, the disease or disorder is causally associated with ER activity, overactivity, constitutive activity, expression, overexpression, or accumulation and aggregation. In some embodiments, the disease or disorder is cancer or a neoplasia causally associated with ER activity, overactivity, constitutive activity, expression, overexpression, or accumulation and aggregation. In some embodiments, the disease or disorder is breast cancer, ovarian cancer, endometrial cancer or uterine cancer. In some embodiments, the disease or disorder is endometriosis.

In another aspect, the present disclosure provides a pharmaceutical composition comprising a therapeutically effective amount of an amorphous form of Compound A and a pharmaceutically acceptable dispersing agent. In some embodiments, the pharmaceutically acceptable dispersing agent further comprises a pharmaceutically acceptable additive. In some embodiments, the pharmaceutically acceptable dispersing agent is hydroxypropyl methylcellulose (HPMC). In some embodiments, the pharmaceutically acceptable additive is D-α-tocopheryl polyethylene glycol succinate (Vitamin E TPGS or TPGS).

In some embodiments, a polymorph of the invention is the preferred form for the storing of Compound A in bulk prior to converting to amorphous Compound A. In some embodiments, the polymorph of Compound A is Form I. In some embodiments, the polymorph of Compound A is Form II. In some embodiments, the polymorph of Compound A is Form III. In some embodiments, the polymorph of Compound A is Form IV. In some embodiments, the form for storing of Compound A in bulk is a mixture of one or more solid forms (e.g. polymorphs or amorphous form) of Compound A disclosed herein. In some embodiments, the form for storing of Compound A in bulk is a mixture of Form I and the amorphous form. In some embodiments, the form for storing of Compound A in bulk is a mixture of Form I and Form II. In some embodiments, the form for storing of Compound A in bulk is a mixture of Form I and Form III. In some embodiments, the preferred form for storing of Compound A in bulk is a mixture of Form I and Form IV.

In another aspect, the present disclosure provides the use of a polymorph and/or amorphous form of Compound A in the manufacture of a medicament for the treatment of a disease or disorder. In some embodiments, the disease or disorder is associated with ER activity, overactivity, constitutive activity, expression, overexpression, or accumulation and aggregation. In some embodiments, the disease or disorder is cancer or a neoplasia associated with ER activity, overactivity, constitutive activity, expression, overexpression, or accumulation and aggregation. In some embodiments, the disease or disorder is breast cancer, ovarian cancer, endometrial cancer or uterine cancer. In some embodiments, the disease or disorder is endometriosis.

In another aspect, the present disclosure provides a polymorph and/or amorphous form of Compound A for use in medicine.

In another aspect, the present disclosure provides a polymorph and/or amorphous form of Compound A for use in the treatment of a disease or disorder. In some embodiments, the disease or disorder is associated with ER activity, overactivity, constitutive activity, expression, overexpression, or accumulation and aggregation. In some embodiments, the disease or disorder is cancer or a neoplasia associated with ER activity, overactivity, constitutive activity, expression, overexpression, or accumulation and aggregation. In some embodiments, the disease or disorder is breast cancer, ovarian cancer, endometrial cancer or uterine cancer. In some embodiments, the disease or disorder is endometriosis.

In another aspect, the present disclosure provides a method of making the Form I polymorph of Compound A, comprising recrystallizing Compound A from a solvent. In some embodiments, the solvent is acetone, 1-butanol, 2-ethoxyethanol, ethanol, ethyl acetate, isopropyl acetate, methanol, methyl ethyl ketone, 1-propanol, 2-propanol, or a mixture of ethanol and water.

In another aspect, the present disclosure provides a method of making the Form II polymorph of Compound A, comprising recrystallizing Compound A from a solvent. In some embodiments, the solvent is dichloromethane or a mixture of acetone and water.

In another aspect, the present disclosure provides a method of making the Form III polymorph of Compound A, comprising recrystallizing Compound A from a solvent. In some embodiments, the solvent is acetonitrile.

In another aspect, the present disclosure provides a method of making the Form IV polymorph of Compound A, comprising crash-cooling Compound A from a solvent. In some embodiments, the solvent is a mixture of dichloromethane and methanol.

In another aspect, the present disclosure provides a method of making the Form IV polymorph of Compound A, comprising addition of an anti-solvent to a solution of Compound A from a solvent. In some embodiments, the solvent comprises a mixture of dichloromethane and methanol. In some embodiments, the anti-solvent is tert-butyl methyl ether.

DETAILED DESCRIPTION

Figure 1A:
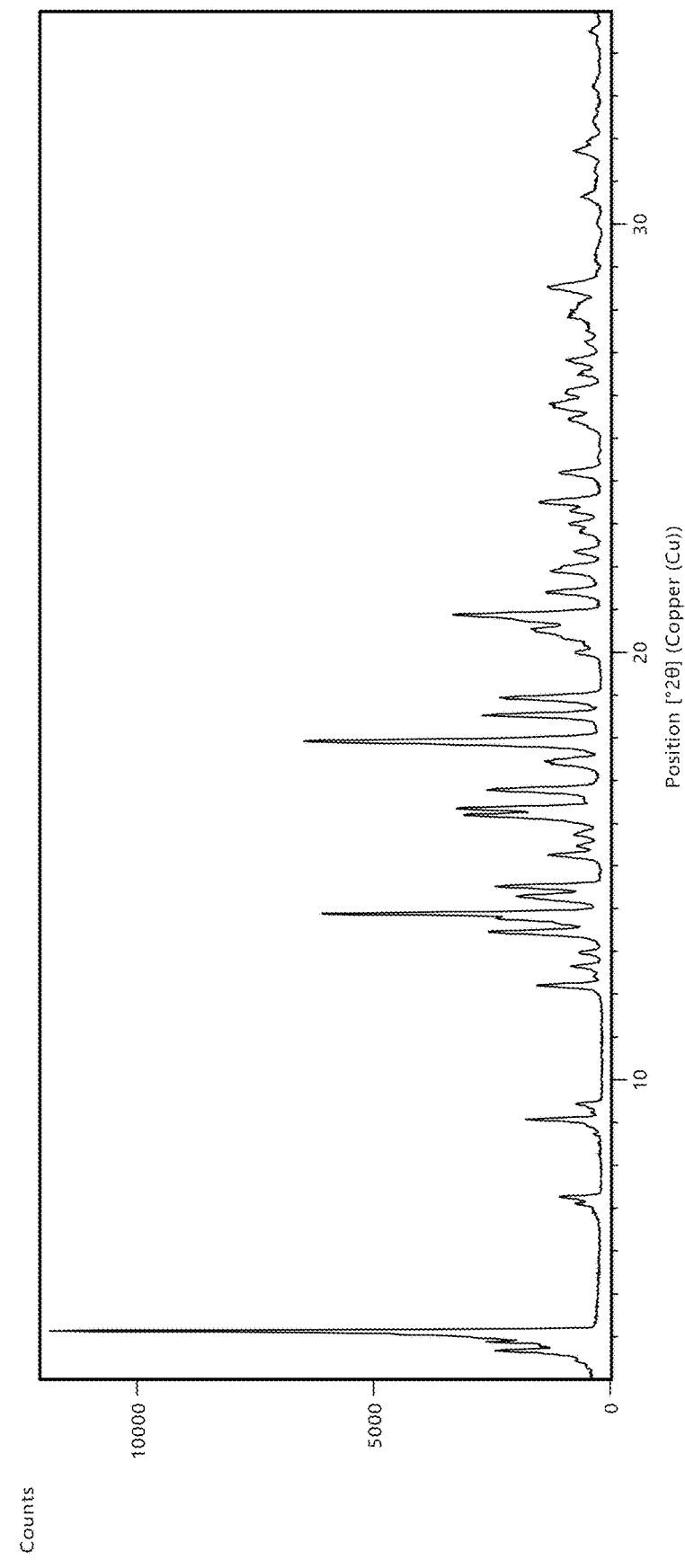
FIG. 1A shows the XRPD spectrum of a sample of the Form I polymorph of Compound A. The diffractogram is from material recovered from methyl ethyl ketone.

The present application is related to U.S. patent application Ser. No. 15/829,541, issued as U.S. Pat. No. 10,647,698; U.S. patent application Ser. No. 16/744,414, issued as U.S. Pat. No. 10,899,742, and U.S. patent application Ser. No. 17/001,519. Each of these is incorporated herein by reference in its entirety for all purposes.

The following is a detailed description provided to aid those skilled in the art in practicing the present disclosure. Those of ordinary skill in the art may make modifications and variations in the embodiments described herein without departing from the spirit or scope of the present disclosure. All publications, patent applications, patents, figures and other references mentioned herein are expressly incorporated by reference in their entirety for all purposes.

Unless otherwise defined, all technical and scientific terms used herein have the same meaning as commonly understood by one of ordinary skill in the art to which this disclosure belongs. The terminology used in the description is for describing particular embodiments only and is not intended to be limiting of the disclosure.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the present disclosure. The upper and lower limits of these smaller ranges may independently be included in the smaller ranges subject to any specifically excluded limit in the stated range. Where the stated range includes one or both of the limits, ranges excluding either or both of those included limits are also included in the disclosure.

Definitions

The following terms are used to describe the present disclosure. In instances where a term is not specifically defined herein, that term is given an art-recognized meaning by those of ordinary skill applying that term in context to its use in describing the present disclosure.

As defined herein, "XRPD" or "XPD" is understood to mean X-ray powder diffraction. Unless otherwise specified, all XRPD peaks and patterns are given in °2θ using Cu Kα1 radiation at a wavelength of 1.5406 Å.

The abbreviations "TG" and "TGA" are understood to mean thermogravimetry or thermogravimetric analysis. The abbreviation "DT" or "DTA" are understood to mean differential thermal analysis. The abbreviations "TG/DT" and "TG/DTA" are understood to mean thermogravimetry/differential thermal analysis.

The term "PLM" is understood to mean polarized light microscopy.

The term "about" is used herein to mean approximately, in the region of, roughly or around. When the term "about" is used in conjunction with a numerical range, it modifies that range by extending the boundaries above and below the numerical values set forth. In general, the term "about" is used herein to modify a numerical value above and below the stated value by a variance of 20%. When used in the context of XRPD peak values (i.e. the positions of an XRPD peak along the x axis of the diffractogram), the term "about" can indicate a peak value±0.20; ±0.15; ±0.10; ±0.05; or ±0.01°2θ. In some embodiments, when used in the context of XRPD peak values "about" can indicate a peak value at exactly the disclosed peak value.

As used herein, the term "substantially" means greater than 85% (i.e., greater than 85, 86, 87, 88, 89, 90, 91, 92, 93, 94, 95, 96, 97, 98, 99, or 100%).

The term "substantially similar" as used herein with regards to an analytical spectrum, such as an XRPD pattern, means that a spectrum resembles the reference spectrum to a great degree in both the peak locations and their relative intensities. For example, two spectra may be regarded as "substantially similar" when the two spectra share defining characteristics sufficient to differentiate them from a spectrum obtained for a different solid form. In certain embodiments, spectra or characterization data that are substantially similar to those of a reference crystalline form, amorphous form, or mixture thereof, are understood by those of ordinary skill in the art to correspond to the same crystalline form, amorphous form, or mixture thereof as the particular reference. In analyzing whether spectra or characterization data are substantially similar, a person of ordinary skill in the art understands that particular characterization data points may vary to a reasonable extent while still describing a given solid form, due to, for example, experimental error and routine sample-to-sample analysis.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of" "only one of," or "exactly one of."

In the claims, as well as in the specification, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The terms "crystalline form," "morphic form," and "polymorph" are each understood to mean any solid that has a short or long range order of the molecules, atoms or ions in a fixed lattice arrangement. Crystals of the present invention may be in a single crystal form. Therefore, the crystals of the present invention may be in e.g., a triclinic, monoclinic, orthorhombic, tetragonal, rhombohedral, hexagonal or cubic crystal form or mixtures thereof. In another particular embodiment, the crystals of the present invention are substantially free of other forms, e.g., free of amorphous or other crystal forms.

The term "amorphous" form refers to solids of disordered arrangements of molecules and do not possess a distinguishable crystal lattice.

The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects, one or more of the present compounds described herein are co-administered in combination with at least one additional bioactive agent, especially including an anticancer agent. In particularly preferred aspects, the co-administration of compounds results in improved activity or synergistic activity and/or therapy, including anticancer activity.

The term "compound", as used herein, unless otherwise indicated, refers to any specific chemical compound disclosed herein, including deuterated forms thereof where applicable, in context. Deuterated small molecules contemplated are those in which one or more of the hydrogen atoms contained in the drug molecule have been replaced by deuterium. Unless the context indicates otherwise, the term compound refers to Compound A.

The term "ubiquitin ligase" refers to a family of proteins that facilitate the transfer of ubiquitin to a specific substrate protein, targeting the substrate protein for degradation. For example, cereblon is an E3 ubiquitin ligase protein that alone or in combination with an E2 ubiquitin-conjugating enzyme causes the attachment of ubiquitin to a lysine on a target protein. Thus, E3 ubiquitin ligase alone or in complex with an E2 ubiquitin conjugating enzyme is responsible for the transfer of ubiquitin to targeted proteins. In general, the ubiquitin ligase is involved in polyubiquitination such that a second ubiquitin is attached to the first; a third is attached to the second, and so forth. Such polyubiquitination marks the target proteins for degradation by the proteasome.

The term "patient" or "subject" is used throughout the specification to describe an animal, preferably a human or a domesticated animal, to whom treatment, including prophylactic treatment, with the compositions according to the present disclosure is provided. For treatment of those infections, conditions or disease states which are specific for a specific animal such as a human patient, the term "patient" refers to that specific animal, including a domesticated animal such as a dog or cat or a farm animal such as a horse, cow, sheep, etc. In general, in the present disclosure, the term "patient" refers to a human patient unless otherwise stated or implied from the context of the use of the term.

The term "effective" is used to describe an amount of a compound, composition or component which, when used within the context of its intended use, effects an intended result. The term "effective" subsumes all other effective amounts or effective concentration terms, which are otherwise described or used in the present application.

The phrase "therapeutically effective amount" and the like, as used herein, indicate an amount necessary to administer to a patient, or to a cell, tissue, or organ of a patient, to achieve a therapeutic effect, such as an ameliorating or alternatively a curative effect. The therapeutically effective amount is sufficient to elicit the biological or medical response of a cell, tissue, system, animal, or human that is being sought by a researcher, veterinarian, medical doctor, or clinician. Determination of the appropriate therapeutically effective amount is within the routine level of skill in the art.

Polymorphs

Compound A can be prepared according to the methods disclosed in U.S. Pat. No. 10,647,698, which is incorporated herein for all purposes. The Form I polymorph of Compound A can be prepared by crystallization from a number of solvents. For instance, Form I was recovered from each of the following solvents by temperature cycling between ambient temperature (about 22° C.) and 40° C. in 4 hour cycles for 72 hours: acetone, 1-butanol, 2-ethoxyethanol, ethanol, ethyl acetate, isopropyl acetate, methanol, methyl ethyl ketone, 1-propanol, 2-propanol, and ethanol:water (90:10 v/v). An XRPD spectrum of Form I, recovered from methyl ethyl ketone is shown in FIG. 1A, obtained using Cu Kα radiation.

In some embodiments, this application provides a method of making Form I of the polymorph as disclosed herein, comprising recrystallizing Compound A from a solvent. In some embodiments, the solvent is acetone, 1-butanol, 2-ethoxyethanol, ethanol, ethyl acetate, isopropyl acetate, methanol, methyl ethyl ketone, 1-propanol, 2-propanol, or a mixture of ethanol and water. In some embodiments, the solvent is acetone. In some embodiments, the solvent is 1-butanol. In some embodiments, the solvent is 2-ethoxyethanol. In some embodiments, the solvent is ethanol. In some embodiments, the solvent is ethyl acetate. In some embodiments, the solvent is isopropyl acetate. In some embodiments, the solvent is methanol. In some embodiments, the solvent is methyl ethyl ketone. In some embodiments, the solvent is 1-propanol. In some embodiments, the solvent is 2-propanol. In some embodiments, the solvent is a mixture of ethanol/water. In some embodiments, the ratio of ethanol to water is between about 85:15 (v/v) and about 95:5 (v/v). In some embodiments, the ratio of ethanol to water is between 85:15 (v/v) and 95:5 (v/v). In some embodiments, the ratio of ethanol to water is about 90:10 (v/v). In some embodiments, the water is deionized water.

In some embodiments, Form I can be characterized by the XRPD peaks shown in FIG. 1A. For example, in some embodiments, Form I can be characterized by an XRPD peak at about 17.9°2θ (e.g. 17.9±0.2°2θ, 17.9±0.1°2θ, or 17.9±0.0°2θ; Cu Kα radiation). In some embodiments, Form I can be further characterized by XRPD peaks at about 13.9°2θ and/or about 16.4°2θ (e.g., ±0.2°2θ, ±0.1°2θ, or ±0.0°2θ; Cu Kα radiation). In some embodiments, Form I can be further characterized by XRPD peaks at about 16.2°2θ, about 18.5°2θ, about 16.8°2θ, about 14.5°2θ, and/or about 13.5°2θ (e.g., ±0.2°2θ, ±0.1°2θ, or ±0.0°2θ; Cu Kα radiation).

In some embodiments, Form I can be characterized by an XRPD peak at about 17.9°2θ (e.g., ±0.2°2θ, ±0.1°2θ or ±0.0°2θ; Cu Kα radiation). In some embodiments, Form I can be characterized by an XRPD peak at about 13.9°2θ (e.g., ±0.2°2θ, ±0.1°2θ, or ±0.0°2θ; Cu Kα radiation). In some embodiments, Form I can be characterized by XRPD peaks at about 17.9°2θ and about 13.9°2θ (e.g., ±0.2°2θ, ±0.1°2θ, or ±0.0°2θ; Cu Kα radiation).

In some embodiments, Form I can be characterized by XRPD peaks at about 13.5°2θ, about 17.9°2θ and about 13.9°2θ (e.g., ±0.2°2θ, ±0.1°2θ, or ±0.0°2θ; Cu Kα radiation). In some embodiments, Form I can be characterized by XRPD peaks at about 14.3°2θ, about 17.9°2θ and about 13.9°2θ (e.g., ±0.2°2θ, ±0.1°2θ, or ±0.0°2θ; Cu Kα radiation). In some embodiments, Form I can be characterized by XRPD peaks at about 14.5°2θ, about 17.9°2θ and about 13.9°2θ (e.g., ±0.2°2θ, ±0.1°2θ, or ±0.0°2θ; Cu Kα radiation). In some embodiments, Form I can be characterized by XRPD peaks at about 16.2°2θ, about 17.9°2θ and about 13.9°2θ (e.g., ±0.2°2θ, ±0.1°2θ, or ±0.0°2θ; Cu Kα radiation). In some embodiments, Form I can be characterized by XRPD peaks at about 16.4°2θ, about 17.9°2θ and about 13.9°2θ (e.g., ±0.2°2θ, ±0.1°2θ, or ±0.0°2θ; Cu Kα radiation). In some embodiments, Form I can be characterized by XRPD peaks at about 16.8°2θ, about 17.9°2θ and about 13.9°2θ (e.g., ±0.2°2θ, ±0.1°2θ, or ±0.0°2θ; Cu Kα radiation). In some embodiments, Form I can be characterized by XRPD peaks at about 18.5°2θ, about 17.9°2θ and about 13.9°2θ (e.g., ±0.2°2θ, ±0.1°2θ, or ±0.0°2θ; Cu Kα radiation). In some embodiments, Form I can be characterized by XRPD peaks at about 18.9°2θ, about 17.9°2θ and about 13.9°2θ (e.g., ±0.2°2θ, ±0.1°2θ, or ±0.0°2θ; Cu Kα radiation).

In some embodiments, Form I can be characterized by XRPD peaks at about 16.4°2θ, about 16.8°2θ, about 18.5°2θ, and about 20.9°2θ (e.g., ±0.2°2θ, ±0.1°2θ, or ±0.0°2θ; Cu Kα radiation). In some embodiments, Form I can be characterized by XRPD peaks at about 16.4°2θ, about 16.8°2θ, about 17.9°2θ, and about 20.9°2θ (e.g., ±0.2°2θ, ±0.1°2θ, or ±0.0°2θ; Cu Kα radiation). In some embodiments, Form I can be characterized by XRPD peaks at about 16.4°2θ, about 16.8°2θ, about 17.9°2θ, and about 18.5°2θ (e.g., ±0.2°2θ, ±0.1°2θ, or ±0.0°2θ; Cu Kα radiation). In some embodiments, Form I can be characterized by XRPD peaks at about 16.2°2θ, about 17.9°2θ, about 18.5°2θ, and about 20.9°2θ (e.g., ±0.2°2θ, ±0.1°2θ, or ±0.0°2θ; Cu Kα radiation). In some embodiments, Form I can be characterized by XRPD peaks at about 16.2°2θ, about 16.8°2θ, about 18.5°2θ, and about 20.9°2θ (e.g., ±0.2°2θ, ±0.1°2θ, or ±0.0°2θ; Cu Kα radiation). In some embodiments, Form I can be characterized by XRPD peaks at about 16.2°2θ, about 16.8°2θ, about 17.9°2θ, and about 20.9°2θ (e.g., ±0.2°2θ, ±0.1°2θ, or ±0.0°2θ; Cu Kα radiation). In some embodiments, Form I can be characterized by XRPD peaks at about 16.2°2θ, about 16.8°2θ, about 17.9°2θ, and about 18.5°2θ (e.g., ±0.2°2θ, ±0.1°2θ, or ±0.0°2θ; Cu Kα radiation). In some embodiments, Form I can be characterized by XRPD peaks at about 16.2°2θ, about 16.4°2θ, about 18.5°2θ, and about 20.9°2θ (e.g., ±0.2°2θ, ±0.1°2θ, or ±0.0°2θ; Cu Kα radiation). In some embodiments, Form I can be characterized by XRPD peaks at about 16.2°2θ, about 16.4°2θ, about 17.9°2θ, and about 20.9°2θ (e.g., ±0.2°2θ, ±0.1°2θ, or ±0.0°2θ; Cu Kα radiation). In some embodiments, Form I can be characterized by XRPD peaks at about 16.2°2θ, about 16.4°2θ, about 17.9°2θ, and about 18.5°2θ (e.g., ±0.2°2θ, ±0.1°2θ, or ±0.0°2θ; Cu Kα radiation). In some embodiments, Form I can be characterized by XRPD peaks at about 16.2°2θ, about 16.4°2θ, about 16.8°2θ, and about 20.9°2θ (e.g., ±0.2°2θ, ±0.1°2θ, or ±0.0°2θ; Cu Kα radiation). In some embodiments, Form I can be characterized by XRPD peaks at about 16.2°2θ, about 16.4°2θ, about 16.8°2θ, and about 18.5°2θ (e.g., ±0.2°2θ, ±0.1°2θ, or ±0.0°2θ; Cu Kα radiation). In some embodiments, Form I can be characterized by XRPD peaks at about 16.2°2θ, about 16.4°2θ, about 16.8°2θ, and about 17.9°2θ (e.g., ±0.2°2θ, ±0.1°2θ, or ±0.0°2θ; Cu Kα radiation). In some embodiments, Form I can be characterized by XRPD peaks at about 13.9°2θ, about 18.5°2θ, and about 20.9°2θ (e.g., ±0.2°2θ, ±0.1°2θ, or ±0.0°2θ; Cu Kα radiation). In some embodiments, Form I can be characterized by XRPD peaks at about 13.9°2θ, about 16.8°2θ, about 18.5°2θ, and about 20.9°2θ (e.g., ±0.2°2θ, ±0.1°2θ, or ±0.0°2θ; Cu Kα radiation). In some embodiments, Form I can be characterized by XRPD peaks at about 13.9°2θ, about 16.8°2θ, about 17.9°2θ, and about 20.9°2θ (e.g., ±0.2°2θ, ±0.1°2θ, or ±0.0°2θ; Cu Kα radiation). In some embodiments, Form I can be characterized by XRPD peaks at about 13.9°2θ, about 16.8°2θ, about 17.9°2θ, and about 18.5°2θ (e.g., ±0.2°2θ, ±0.1°2θ, or ±0.0°2θ; Cu Kα radiation). In some embodiments, Form I can be characterized by XRPD peaks at about 13.9°2θ, about 16.4°2θ, about 18.5°2θ, and about 20.9°2θ (e.g., ±0.2°2θ, ±0.1°2θ, or ±0.0°2θ; Cu Kα radiation). In some embodiments, Form I can be characterized by XRPD peaks at about 13.9°2θ, about 16.4°2θ, about 17.9°2θ, and about 20.9°2θ (e.g., ±0.2°2θ, ±0.1°2θ, or ±0.0°2θ; Cu Kα radiation). In some embodiments, Form I can be characterized by XRPD peaks at about 13.9°2θ, about 16.4°2θ, about 17.9°2θ, and about 18.5°2θ (e.g., ±0.2°2θ, ±0.1°2θ, or ±0.0°2θ; Cu Kα radiation). In some embodiments, Form I can be characterized by XRPD peaks at about 13.9°2θ, about 16.4°2θ, about 16.8°2θ, and about 20.9°2θ (e.g., ±0.2°2θ, ±0.1°2θ, or ±0.0°2θ; Cu Kα radiation). In some embodiments, Form I can be characterized by XRPD peaks at about 13.9°2θ, about 16.4°2θ, about 16.8°2θ, and about 18.5°2θ (e.g., ±0.2°2θ, ±0.1°2θ, or ±0.0°2θ; Cu Kα radiation). In some embodiments, Form I can be characterized by XRPD peaks at about 13.9°2θ, about 16.4°2θ, about 16.8°2θ, and about 17.9°2θ (e.g., ±0.2°2θ, ±0.1°2θ, or ±0.0°2θ; Cu Kα radiation). In some embodiments, Form I can be characterized by XRPD peaks at about 13.9°2θ, about 16.2°2θ, about 18.5°2θ, and about 20.9°2θ (e.g., ±0.2°2θ, ±0.1°2θ, or ±0.0°2θ; Cu Kα radiation). In some embodiments, Form I can be characterized by XRPD peaks at about 13.9°2θ, about 16.2°2θ, about 17.9°2θ, and about 20.9°2θ (e.g., ±0.2°2θ, ±0.1°2θ, or ±0.0°2θ; Cu Kα radiation). In some embodiments, Form I can be characterized by XRPD peaks at about 13.9°2θ, about 16.2°2θ, about 17.9°2θ, and about 18.5°2θ (e.g., ±0.2°2θ, ±0.1°2θ, or ±0.0°2θ; Cu Kα radiation). In some embodiments, Form I can be characterized by XRPD peaks at about 13.9°2θ, about 16.2°2θ, about 16.8°2θ, and about 20.9°2θ (e.g., ±0.2°2θ, ±0.1°2θ, or ±0.0°2θ; Cu Kα radiation). In some embodiments, Form I can be characterized by XRPD peaks at about 13.9°2θ, about 16.2°2θ, about 16.8°2θ, and about 18.5°2θ (e.g., ±0.2°2θ, ±0.1°2θ, or ±0.0°2θ; Cu Kα radiation). In some embodiments, Form I can be characterized by XRPD peaks at about 13.9°2θ, about 16.2°2θ, about 16.8°2θ, and about 17.9°2θ (e.g., ±0.2°2θ, ±0.1°2θ, or ±0.0°2θ; Cu Kα radiation). In some embodiments, Form I can be characterized by XRPD peaks at about 13.9°2θ, about 16.2°2θ, about 16.4°2θ, and about 20.9°2θ (e.g., ±0.2°2θ, ±0.1°2θ, or ±0.0°2θ; Cu Kα radiation). In some embodiments, Form I can be characterized by XRPD peaks at about 13.9°2θ, about 16.2°2θ, about 16.4°2θ, and about 18.5°2θ (e.g., ±0.2°2θ, ±0.1°2θ, or ±0.0°2θ; Cu Kα radiation). In some embodiments, Form I can be characterized by XRPD peaks at about 13.9°2θ, about 16.2°2θ, about 16.4°2θ, and about 17.9°2θ (e.g., ±0.2°2θ, ±0.1°2θ, or ±0.0°2θ; Cu Kα radiation). In some embodiments, Form I can be characterized by XRPD peaks at about 13.9°2θ, about 16.2°2θ, about 16.4°2θ, and about 16.8°2θ (e.g., ±0.2°2θ, ±0.1°2θ, or ±0.0°2θ; Cu Kα radiation).

In some embodiments, Form I can be characterized by one or more XRPD peaks selected from about 17.9°2θ, about 13.9°2θ, about 13.5°2θ, about 14.3°2θ, about 14.5°2θ, about 16.2°2θ, about 16.4°2θ, about 16.8°2θ, about 18.5°2θ, about 18.9°2θ, and about 20.9°2θ (e.g., ±0.2°2θ, ±0.1°2θ, or ±0.0°2θ; Cu Kα radiation). In some embodiments, Form I can be characterized by one XRPD peak selected from about 17.9°2θ, about 13.9°2θ, about 13.5°2θ, about 14.3°2θ, about 14.5°2θ, about 16.2°2θ, about 16.4°2θ, about 16.8°2θ, about 18.5°2θ, about 18.9°2θ, and about 20.9°2θ (e.g., ±0.2°2θ, ±0.1°2θ, or ±0.0°2θ; Cu Kα radiation). In some embodiments, Form I can be characterized by two XRPD peaks selected from about 17.9°2θ, about 13.9°2θ, about 13.5°2θ, about 14.3°2θ, about 14.5°2θ, about 16.2°2θ, about 16.4°2θ, about 16.8°2θ, about 18.5°2θ, about 18.9°2θ, and about 20.9°2θ (e.g., ±0.2°2θ, ±0.1°2θ, or ±0.0°2θ; Cu Kα radiation). In some embodiments, Form I can be characterized by three XRPD peaks selected from about 17.9°2θ, about 13.9°2θ, about 13.5°2θ, about 14.3°2θ, about 14.5°2θ, about 16.2°2θ, about 16.4°2θ, about 16.8°2θ, about 18.5°2θ, about 18.9°2θ, and about 20.9°2θ (e.g., ±0.2°2θ, ±0.1°2θ, or ±0.0°2θ; Cu Kα radiation). In some embodiments, Form I can be characterized by four XRPD peaks selected from about 17.9°2θ, about 13.9°2θ, about 13.5°2θ, about 14.3°2θ, about 14.5°2θ, about 16.2°2θ, about 16.4°2θ, about 16.8°2θ, about 18.5°2θ, about 18.9°2θ, and about 20.9°2θ (e.g., ±0.2°2θ, ±0.1°2θ, or ±0.0°2θ; Cu Kα radiation). In some embodiments, Form I can be characterized by five XRPD peaks selected from about 17.9°2θ, about 13.9°2θ, about 13.5°2θ, about 14.3°2θ, about 14.5°2θ, about 16.2°2θ, about 16.4°2θ, about 16.8°2θ, about 18.5°2θ, about 18.9°2θ, and about 20.9°2θ (e.g., ±0.2°2θ, ±0.1°2θ, or ±0.0°2θ; Cu Kα radiation). In some embodiments, Form I can be characterized by six XRPD peaks selected from about 17.9°2θ, about 13.9°2θ, about 13.5°2θ, about 14.3°2θ, about 14.5°2θ, about 16.2°2θ, about 16.4°2θ, about 16.8°2θ, about 18.5°2θ, about 18.9°2θ, and about 20.9°2θ (e.g., ±0.2°2θ, ±0.1°2θ, or ±0.0°2θ; Cu Kα radiation). In some embodiments, Form I can be characterized by seven XRPD peaks selected from about 17.9°2θ, about 13.9°2θ, about 13.5°2θ, about 14.3°2θ, about 14.5°2θ, about 16.2°2θ, about 16.4°2θ, about 16.8°2θ, about 18.5°2θ, about 18.9°2θ, and about 20.9°2θ (e.g., ±0.2°2θ, ±0.1°2θ, or ±0.0°2θ; Cu Kα radiation). In some embodiments, Form I can be characterized by eight XRPD peaks selected from about 17.9°2θ, about 13.9°2θ, about 13.5°2θ, about 14.3°2θ, about 14.5°2θ, about 16.2°2θ, about 16.4°2θ, about 16.8°2θ, about 18.5°2θ, about 18.9°2θ, and about 20.9°2θ (e.g., ±0.2°2θ, ±0.1°2θ, or ±0.0°2θ; Cu Kα radiation). In some embodiments, Form I can be characterized by nine XRPD peaks selected from about 17.9°2θ, about 13.9°2θ, about 13.5°2θ, about 14.3°2θ, about 14.5°2θ, about 16.2°2θ, about 16.4°2θ, about 16.8°2θ, about 18.5°2θ, about 18.9°2θ, and about 20.9°2θ (e.g., ±0.2°2θ, ±0.1°2θ, or ±0.0°2θ; Cu Kα radiation). In some embodiments, Form I can be characterized by ten XRPD peaks selected from about 17.9°2θ, about 13.9°2θ, about 13.5°2θ, about 14.3°2θ, about 14.5°2θ, about 16.2°2θ, about 16.4°2θ, about 16.8°2θ, about 18.5°2θ, about 18.9°2θ, and about 20.9°2θ (e.g., ±0.2°2θ, ±0.1°2θ, or ±0.0°2θ; Cu Kα radiation). In some embodiments, Form I can be characterized by eleven XRPD peaks selected from about 17.9°2θ, about 13.9°2θ, about 13.5°2θ, about 14.3°2θ, about 14.5°2θ, about 16.2°2θ, about 16.8°2θ, about 18.5°2θ, about 18.9°2θ, and about 20.9°2θ (e.g., ±0.2°2θ, ±0.1°2θ, or ±0.0°2θ; Cu Kα radiation).

In some embodiments, Form I can have one, two, three, four, five, six, seven, eight, nine, ten, eleven, or more, peaks as those listed in Table 1.

TABLE 1

Representative XRPD Peaks for Form I

| Pos. [°2θ] | d-spacing [Å] | Height [cts] | Rel. Int. [%] |
|---|---|---|---|
| 3.6794 | 24.01398 | 2313.02 | 19.81 |
| 3.8756 | 22.79899 | 2478.34 | 21.23 |
| 4.1441 | 21.32234 | 11675.34 | 100 |
| 6.9208 | 12.76202 | 132.3 | 1.13 |
| 7.1024 | 12.44643 | 576.9 | 4.94 |
| 7.2611 | 12.17467 | 923.83 | 7.91 |
| 8.7237 | 10.13655 | 178.93 | 1.53 |
| 9.0851 | 9.73407 | 1617.57 | 13.85 |
| 9.2349 | 9.56862 | 157.09 | 1.35 |
| 9.4458 | 9.36321 | 566.07 | 4.85 |
| 12.1977 | 7.2503 | 1027.94 | 8.8 |
| 12.6561 | 6.99444 | 671.67 | 5.75 |
| 12.9576 | 6.82674 | 353.44 | 3.03 |
| 13.4528 | 6.57655 | 1815.26 | 15.55 |
| 13.6342 | 6.48945 | 722.45 | 6.19 |
| 13.7568 | 6.43721 | 2223.6 | 19.05 |
| 13.8802 | 6.38026 | 6147.97 | 52.66 |
| 14.3023 | 6.19289 | 1836.86 | 15.73 |
| 14.5387 | 6.09272 | 2235.72 | 19.15 |
| 15.2684 | 5.80316 | 1167.67 | 10 |
| 15.4717 | 5.72735 | 547.17 | 4.69 |
| 15.7262 | 5.63523 | 618.11 | 5.29 |
| 16.1936 | 5.47362 | 3003.02 | 25.72 |
| 16.3556 | 5.41977 | 3153.49 | 27.01 |
| 16.7866 | 5.28158 | 2483.19 | 21.27 |
| 17.4196 | 5.08684 | 945.87 | 8.1 |
| 17.9153 | 4.95128 | 6449.03 | 55.24 |
| 18.5062 | 4.7945 | 2524 | 21.62 |
| 18.923 | 4.68984 | 2126 | 18.21 |
| 19.9726 | 4.44568 | 562.89 | 4.82 |
| 20.3127 | 4.372 | 825.38 | 7.07 |
| 20.5514 | 4.32176 | 1507.03 | 12.91 |
| 20.7239 | 4.28618 | 1678.74 | 14.38 |
| 20.8823 | 4.25401 | 3220.85 | 27.59 |
| 21.403 | 4.15169 | 1197.46 | 10.26 |
| 21.8812 | 4.06203 | 1048.27 | 8.98 |
| 22.0112 | 4.03833 | 830.47 | 7.11 |
| 22.3767 | 3.97318 | 544.34 | 4.66 |
| 22.7898 | 3.90209 | 435.98 | 3.73 |
| 22.9759 | 3.8709 | 696.63 | 5.97 |
| 23.288 | 3.81974 | 668.72 | 5.73 |
| 23.4782 | 3.78922 | 1326.86 | 11.36 |
| 24.1801 | 3.68079 | 928.13 | 7.95 |
| 25.4447 | 3.50065 | 701.74 | 6.01 |
| 25.8107 | 3.45184 | 1131.81 | 9.69 |
| 26.1499 | 3.40783 | 707.92 | 6.06 |
| 26.4817 | 3.36588 | 519.68 | 4.45 |
| 26.8378 | 3.32202 | 766.43 | 6.56 |
| 27.2451 | 3.27328 | 342.62 | 2.93 |
| 27.5046 | 3.24298 | 319.63 | 2.74 |
| 27.8727 | 3.19833 | 617.83 | 5.29 |
| 28.0884 | 3.17426 | 471.97 | 4.04 |
| 28.5462 | 3.12697 | 1167.74 | 10 |
| 29.1681 | 3.0617 | 138.79 | 1.19 |
| 30.0513 | 2.9737 | 106.33 | 0.91 |
| 30.6346 | 2.9184 | 448.45 | 3.84 |
| 31.2775 | 2.85986 | 144.05 | 1.23 |
| 31.7342 | 2.81974 | 563.93 | 4.83 |
| 31.9455 | 2.80157 | 312.33 | 2.68 |
| 32.4191 | 2.76171 | 208.46 | 1.79 |
| 33.2109 | 2.69766 | 178.84 | 1.53 |
| 34.5042 | 2.59945 | 264.9 | 2.27 |

Figure 1B:
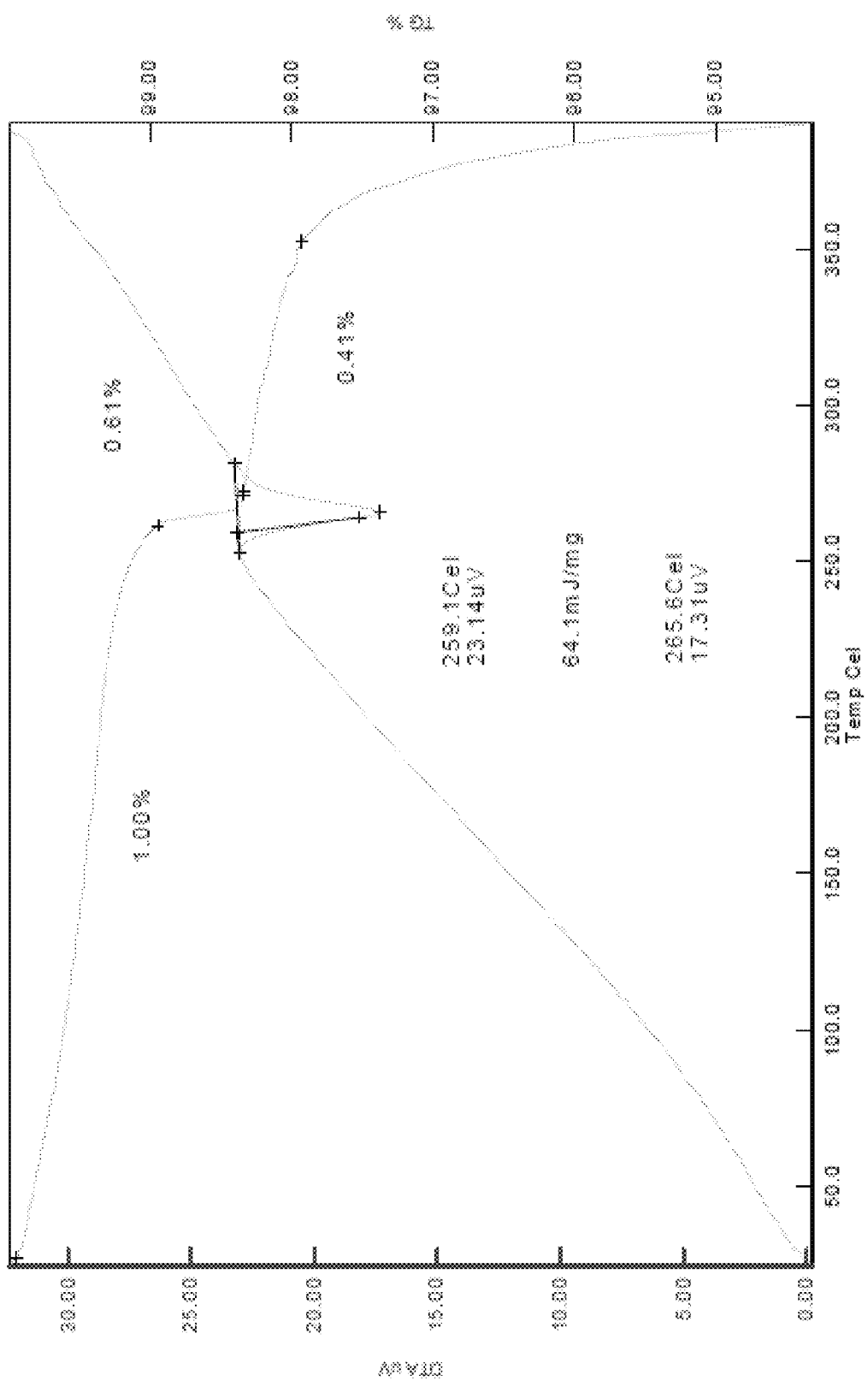
FIG. 1B shows a TG/DT plot of a sample of the Form I polymorph of Compound A. The TG plot begins at the top left, and the DT plot begins at the bottom left.

FIG. 1B is a TG/DT plot of a sample of Form I. TG showed a weight loss of about 1% up to the melt at about 250° C. This was followed by 0.6% weight loss during the melt, and a final weight loss of 0.4% can be seen up to about 350° C. An endothermic event was noted in the DT trace with an onset of about 259° C., with a peak at about 266° C. In some embodiments, Form I is characterized by a weight loss of about 1% between about 25° C. and about 250° C. In some embodiments, Form I is characterized by an endothermic event, as measured by DT, with an onset of about 259° C. In some embodiments, Form I is characterized by an endothermic event, as measured by DT, with a peak at about 166° C. In some embodiments, Form I is characterized by an endothermic event, as measured by DT, with an onset of about 259° C. and a peak at about 266° C. In some embodiments, weight loss is determined by thermogravimetric analysis. In some embodiments, thermogravimetric analysis is conducted substantially as shown in Example 1. In some embodiments, endothermic events are calculated by differential thermal analysis. In some embodiments, differential thermal analysis is conducted substantially as shown in Example 1. In some embodiments, thermogravimetric analysis and differential thermal analysis are conducted simultaneously.

Figure 1C:
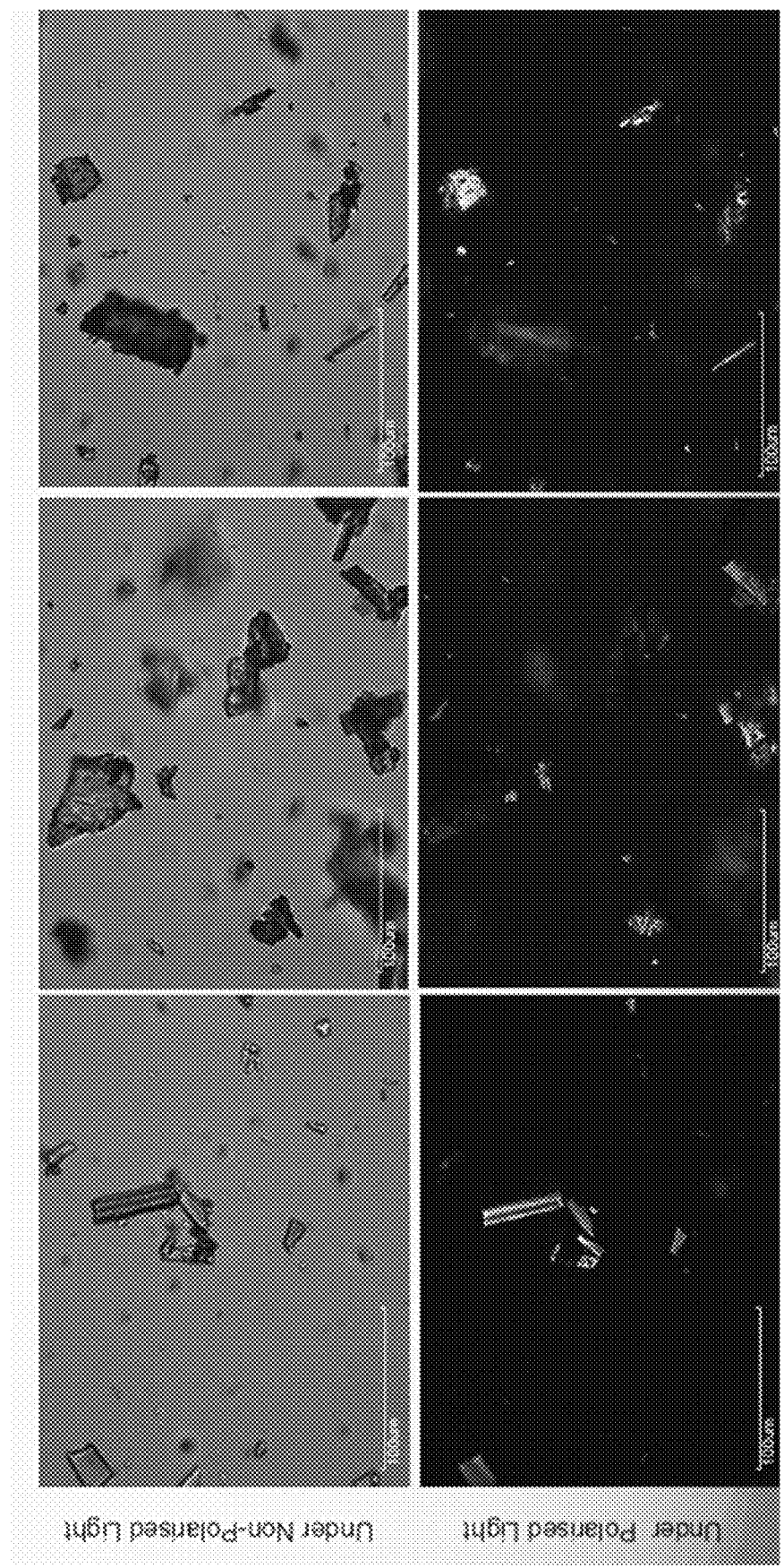
FIG. 1C shows PLM images of the Form I polymorph of Compound A. Samples in this figure were recovered from methanol.

FIG. 1C shows PLM images of Form I recovered from methanol. PLM indicated the material to be birefringent with irregular, lath-like morphology. In some embodiments, Form I is characterized by birefringent material with irregular, lath-like morphology.

Form II of Compound A can be prepared by crystallization from a number of solvents. For instance, Form II was recovered by temperature cycling between ambient (about 22° C.) and 40° C. in 4 hour cycles for 72 hours from dichloromethane and also from acetone:water (90:10 v/v). An XRPD spectrum of Form II, recovered from dichloromethane is shown in FIG. 2A, obtained using Cu Kα radiation.

In some embodiments, this application provides a method of making Form II of Compound A as disclosed herein, comprising recrystallizing Compound A from a solvent. In some embodiments, the solvent is selected from dichloromethane and a mixture of acetone and water. In some embodiments, the solvent is dichloromethane. In some embodiments, the solvent is a mixture of acetone and water. In some embodiments, the ratio of acetone to water is between about 85:15 (v/v) and about 95:5 (v/v). In some embodiments, the ratio of acetone to water is between 85:15 (v/v) and 95:5 (v/v). In some embodiments, the ratio of acetone to water is about 90:10 (v/v). In some embodiments, the water is deionized water.

Figure 2A:
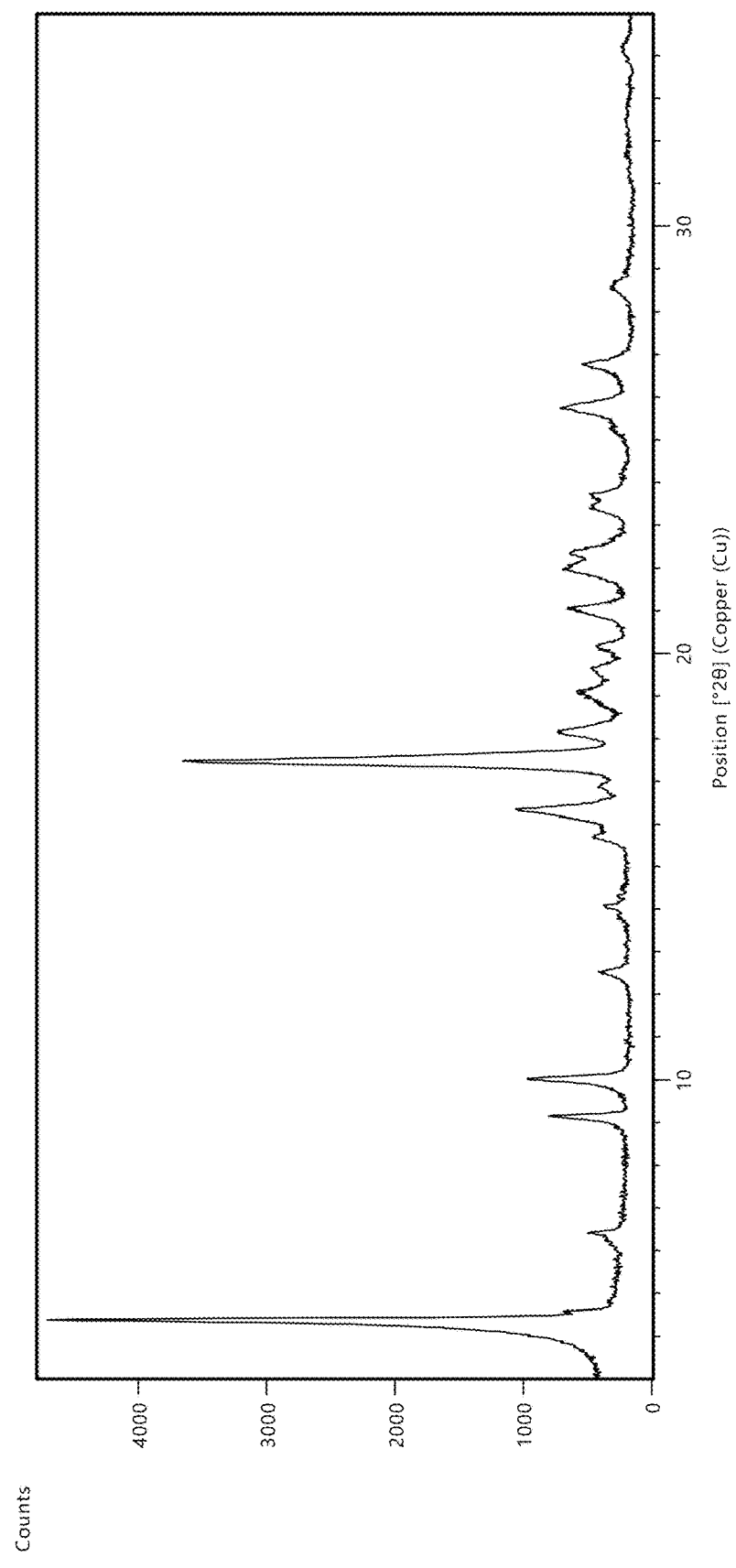
FIG. 2A shows the XRPD spectrum of a sample of Form II of Compound A. The diffractogram is from material recovered from dichloromethane.

In some embodiments, Form II can be characterized by the XRPD peaks shown in FIG. 2A. For example, Form II can be characterized by an XRPD peak at about 17.5°2θ (e.g. 17.5±0.2°2θ, 17.5±0.1°2θ, or 17.5±0.0°2θ). In some embodiments, Form II can be further characterized by XRPD peaks at about 9.2°2θ, about 10.0°2θ, about 16.3°2θ, and/or about 18.1°2θ (e.g., ±0.2°2θ, ±0.1°2θ, or ±0.0°2θ; Cu Kα radiation). In some embodiments, Form II can be further characterized by XRPD peaks at about 12.5°2θ, about 14.1°2θ, about 15.7°2θ, about 16.9°2θ, about 19.1°2θ, and/or about 19.6°2θ (e.g., ±0.2°2θ, ±0.1°2θ, or ±0.0°2θ; Cu Kα radiation).

In some embodiments, Form II can be characterized by XRPD peaks at about 9.2°2θ and about 17.5°2θ (e.g., ±0.2°2θ, ±0.1°2θ, or ±0.0°2θ; Cu Kα radiation). In some embodiments, Form II can be characterized by XRPD peaks at about 10.0°2θ and about 17.5°2θ (e.g., ±0.2°2θ, ±0.1°2θ, or ±0.0°2θ; Cu Kα radiation). In some embodiments, Form II can be characterized by XRPD peaks at about 16.3°2θ and about 17.5°2θ (e.g., ±0.2°2θ, ±0.1°2θ, or ±0.0°2θ; Cu Kα radiation). In some embodiments, Form II can be characterized by XRPD peaks at about 18.1°2θ and about 17.5°2θ (e.g., ±0.2°2θ, ±0.1°2θ, or ±0.0°2θ; Cu Kα radiation). In some embodiments, Form II can be characterized by XRPD peaks at about 12.5°2θ and about 17.5°2θ (e.g., ±0.2°2θ, ±0.1°2θ, or ±0.0°2θ; Cu Kα radiation). In some embodiments, Form II can be characterized by XRPD peaks at about 14.1°2θ and about 17.5°2θ (e.g., ±0.2°2θ, ±0.1°2θ, or ±0.0°2θ; Cu Kα radiation). In some embodiments, Form II can be characterized by XRPD peaks at about 15.7°2θ and about 17.5°2θ (e.g., ±0.2°2θ, ±0.1°2θ, or ±0.0°2θ; Cu Kα radiation). In some embodiments, Form II can be characterized by XRPD peaks at about 16.9°2θ and about 17.5°2θ (e.g., ±0.2°2θ, ±0.1°2θ, or ±0.0°2θ; Cu Kα radiation). In some embodiments, Form II can be characterized by XRPD peaks at about 19.1°2θ and about 17.5°2θ (e.g., ±0.2°2θ, ±0.1°2θ, or ±0.0°2θ; Cu Kα radiation). In some embodiments, Form II can be characterized by XRPD peaks at about 19.6°2θ and about 17.5°2θ (e.g., ±0.2°2θ, ±0.1°2θ, or ±0.0°2θ; Cu Kα radiation). In some embodiments, Form II can be characterized by XRPD peaks at about 18.1°2θ and about 17.5°2θ (e.g., ±0.2°2θ, ±0.1°2θ, or ±0.0°2θ; Cu Kα radiation).

In some embodiments, Form II can be characterized by XRPD peaks at about 16.3°2θ, about 17.5°2θ, and about 18.1°2θ (e.g., ±0.2°2θ, ±0.1°2θ, or ±0.0°2θ; Cu Kα radiation). In some embodiments, Form II can be characterized by XRPD peaks at about 10.0°2θ, about 17.5°2θ, and about 18.1°2θ (e.g., ±0.2°2θ, ±0.1°2θ, or ±0.0°2θ; Cu Kα radiation). In some embodiments, Form II can be characterized by XRPD peaks at about 10.0°2θ, about 16.3°2θ, and about 18.1°2θ (e.g., ±0.2°2θ, ±0.1°2θ, or ±0.0°2θ; Cu Kα radiation). In some embodiments, Form II can be characterized by XRPD peaks at about 10.0°2θ, about 16.3°2θ, and about 17.5°2θ (e.g., ±0.2°2θ, ±0.1°2θ, or ±0.0°2θ; Cu Kα radiation). In some embodiments, Form II can be characterized by XRPD peaks at about 9.2°2θ, about 17.5°2θ, and about 18.1°2θ (e.g., ±0.2°2θ, ±0.1°2θ, or ±0.0°2θ; Cu Kα radiation). In some embodiments, Form II can be characterized by XRPD peaks at about 9.2°2θ, about 16.3°2θ, and about 18.1°2θ (e.g., ±0.2°2θ, ±0.1°2θ, or ±0.0°2θ; Cu Kα radiation). In some embodiments, Form II can be characterized by XRPD peaks at about 9.2°2θ, about 16.3°2θ, and about 17.5°2θ (e.g., ±0.2°2θ, ±0.1°2θ, or ±0.0°2θ; Cu Kα radiation). In some embodiments, Form II can be characterized by XRPD peaks at about 9.2°2θ, about 10.0°2θ, and about 18.1°2θ (e.g., ±0.2°2θ, ±0.1°2θ, or ±0.0°2θ; Cu Kα radiation). In some embodiments, Form II can be characterized by XRPD peaks at about 9.2°2θ, about 10.0°2θ, and about 17.5°2θ (e.g., ±0.2°2θ, ±0.1°2θ, or ±0.0°2θ; Cu Kα radiation). In some embodiments, Form II can be characterized by XRPD peaks at about 9.2°2θ, about 10.0°2θ, about 16.3°2θ (e.g., ±0.2°2θ, ±0.1°2θ, or ±0.0°2θ; Cu Kα radiation).

In some embodiments, Form II can be characterized by XRPD peaks at about 10.0°2θ, about 16.3°2θ, about 17.5°2θ, and about 18.1°2θ (e.g., ±0.2°2θ, ±0.1°2θ, or ±0.0°2θ; Cu Kα radiation). In some embodiments, Form II can be characterized by XRPD peaks at about 9.2°2θ, about 16.3°2θ, about 17.5°2θ, and about 18.1°2θ (e.g., ±0.2°2θ, ±0.1°2θ, or ±0.0°2θ; Cu Kα radiation). In some embodiments, Form II can be characterized by XRPD peaks at about 9.2°2θ, about 10.0°2θ, about 17.5°2θ, and about 18.1°2θ (e.g., ±0.2°2θ, ±0.1°2θ, or ±0.0°2θ; Cu Kα radiation). In some embodiments, Form II can be characterized by XRPD peaks at about 9.2°2θ, about 10.0°2θ, about 16.3°2θ, and about 18.1°2θ (e.g., ±0.2°2θ, ±0.1°2θ, or ±0.0°2θ; Cu Kα radiation). In some embodiments, Form II can be characterized by XRPD peaks at about 9.2°2θ, about 10.0°2θ, about 16.3°2θ, and about 17.5°2θ (e.g., ±0.2°2θ, ±0.1°2θ, or ±0.0°2θ; Cu Kα radiation).

In some embodiments, Form II can be characterized by one or more XRPD peaks selected from about 17.5°2θ, about 9.2°2θ, about 10.0°2θ, about 16.3°2θ, about 18.1°2θ, about 12.5°2θ, about 14.1°2θ, about 15.7°2θ, about 16.9°2θ, about 19.1°2θ, about 19.6°2θ, about 21.1°2θ, about 21.9°2θ, about 22.4°2θ, and about 25.8°2θ (e.g., ±0.2°2θ, ±0.1°2θ, or ±0.0°2θ; Cu Kα radiation). In some embodiments, Form II can be characterized by one XRPD peak selected from about 17.5°2θ, about 9.2°2θ, about 10.0°2θ, about 16.3°2θ, about 18.1°2θ, about 12.5°2θ, about 14.1°2θ, about 15.7°2θ, about 16.9°2θ, about 19.1°2θ, about 19.6°2θ, about 21.1°2θ, about 21.9°2θ, about 22.4°2θ, and about 25.8°2θ (e.g., ±0.2°2θ, ±0.1°2θ, or ±0.0°2θ; Cu Kα radiation). In some embodiments, Form II can be characterized by two XRPD peaks selected from about 17.5°2θ, about 9.2°2θ, about 10.0°2θ, about 16.3°2θ, about 18.1°2θ, about 12.5°2θ, about 14.1°2θ, about 15.7°2θ, about 16.9°2θ, about 19.1°2θ, about 19.6°2θ, about 21.1°2θ, about 21.9°2θ, about 22.4°2θ, and about 25.8°2θ (e.g., ±0.2°2θ, ±0.1°2θ, or ±0.0°2θ; Cu Kα radiation). In some embodiments, Form II can be characterized by three XRPD peaks selected from about 17.5°2θ, about 9.2°2θ, about 10.0°2θ, about 16.3°2θ, about 18.1°2θ, about 12.5°2θ, about 14.1°2θ, about 15.7°2θ, about 16.9°2θ, about 19.1°2θ, about 19.6°2θ, about 21.1°2θ, about 21.9°2θ, about 22.4°2θ, and about 25.8°2θ (e.g., ±0.2°2θ, ±0.1°2θ, or ±0.0°2θ; Cu Kα radiation). In some embodiments, Form II can be characterized by four XRPD peaks selected from about 17.5°2θ, about 9.2°2θ, about 10.0°2θ, about 16.3°2θ, about 18.1°2θ, about 12.5°2θ, about 14.1°2θ, about 15.7°2θ, about 16.9°2θ, about 19.1°2θ, about 19.6°2θ, about 21.1°2θ, about 21.9°2θ, about 22.4°2θ, and about 25.8°2θ (e.g., ±0.2°2θ, ±0.1°2θ, or ±0.0°2θ; Cu Kα radiation). In some embodiments, Form II can be characterized by five XRPD peaks selected from about 17.5°2θ, about 9.2°2θ, about 10.0°2θ, about 16.3°2θ, about 18.1°2θ, about 12.5°2θ, about 14.1°2θ, about 15.7°2θ, about 16.9°2θ, about 19.1°2θ, about 19.6°2θ, about 21.1°2θ, about 21.9°2θ, about 22.4°2θ, and about 25.8°2θ (e.g., ±0.2°2θ, ±0.1°2θ, or ±0.0°2θ; Cu Kα radiation). In some embodiments, Form II can be characterized by six XRPD peaks selected from about 17.5°2θ, about 9.2°2θ, about 10.0°2θ, about 16.3°2θ, about 18.1°2θ, about 12.5°2θ, about 14.1°2θ, about 15.7°2θ, about 16.9°2θ, about 19.1°2θ, about 19.6°2θ, about 21.1°2θ, about 21.9°2θ, about 22.4°2θ, and about 25.8°2θ (e.g., ±0.2°2θ, ±0.1°2θ, or ±0.0°2θ; Cu Kα radiation). In some embodiments, Form II can be characterized by seven XRPD peaks selected from about 17.5°2θ, about 9.2°2θ, about 10.0°2θ, about 16.3°2θ, about 18.1°2θ, about 12.5°2θ, about 14.1°2θ, about 15.7°2θ, about 16.9°2θ, about 19.1°2θ, about 19.6°2θ, about 21.1°2θ, about 21.9°2θ, about 22.4°2θ, and about 25.8°2θ (e.g., ±0.2°2θ, ±0.1°2θ, or ±0.0°2θ; Cu Kα radiation). In some embodiments, Form II can be characterized by eight XRPD peaks selected from about 17.5°2θ, about 9.2°2θ, about 10.0°2θ, about 16.3°2θ, about 18.1°2θ, about 12.5°2θ, about 14.1°2θ, about 15.7°2θ, about 16.9°2θ, about 19.1°2θ, about 19.6°2θ, about 21.1°2θ, about 21.9°2θ, about 22.4°2θ, and about 25.8°2θ (e.g., ±0.2°2θ, ±0.1°2θ, or ±0.0°2θ; Cu Kα radiation). In some embodiments, Form II can be characterized by nine XRPD peaks selected from about 17.5°2θ, about 9.2°2θ, about 10.0°2θ, about 16.3°2θ, about 18.1°2θ, about 12.5°2θ, about 14.1°2θ, about 15.7°2θ, about 16.9°2θ, about 19.1°2θ, about 19.6°2θ, about 21.1°2θ, about 21.9°2θ, about 22.4°2θ, and about 25.8°2θ (e.g., ±0.2°2θ, ±0.1°2θ, or ±0.0°2θ; Cu Kα radiation). In some embodiments, Form II can be characterized by ten XRPD peaks selected from about 17.5°2θ, about 9.2°2θ, about 10.0°2θ, about 16.3°2θ, about 18.1°2θ, about 12.5°2θ, about 14.1°2θ, about 15.7°2θ, about 16.9°2θ, about 19.1°2θ, about 19.6°2θ, about 21.1°2θ, about 21.9°2θ, about 22.4°2θ, and about 25.8°2θ (e.g., ±0.2°2θ, ±0.1°2θ, or ±0.0°2θ; Cu Kα radiation). In some embodiments, Form II can be characterized by eleven XRPD peaks selected from about 17.5°2θ, about 9.2°2θ, about 10.0°2θ, about 16.3°2θ, about 18.1°2θ, about 12.5°2θ, about 14.1°2θ, about 15.7°2θ, about 16.9°2θ, about 19.1°2θ, about 19.6°2θ, about 21.1°2θ, about 21.9°2θ, about 22.4°2θ, and about 25.8°2θ (e.g., ±0.2°2θ, ±0.1°2θ, or ±0.0°2θ; Cu Kα radiation). In some embodiments, Form II can be characterized by twelve XRPD peaks selected from about 17.5°2θ, about 9.2°2θ, about 10.0°2θ, about 16.3°2θ, about 18.1°2θ, about 12.5°2θ, about 14.1°2θ, about 15.7°2θ, about 16.9°2θ, about 19.1°2θ about 19.6°2θ, about 21.1°2θ, about 21.9°2θ, about 22.4°2θ, and about 25.8°2θ (e.g., ±0.2°2θ, ±0.1°2θ, or ±0.0°2θ; Cu Kα radiation). In some embodiments, Form II can be characterized by thirteen XRPD peaks selected from about 17.5°2θ, about 9.2°2θ, about 10.0°2θ, about 16.3°2θ, about 18.1°2θ, about 12.5°2θ, about 14.1°2θ, about 15.7°2θ, about 16.9°2θ, about 19.1°2θ, about 19.6°2θ, about 21.1°2θ, about 21.9°2θ, about 22.4°2θ, and about 25.8°2θ (e.g., ±0.2°2θ, ±0.1°2θ, or ±0.0°2θ; Cu Kα radiation). In some embodiments, Form II can be characterized by fourteen XRPD peaks selected from about 17.5°2θ, about 9.2°2θ, about 10.0°2θ, about 16.3°2θ, about 18.1°2θ, about 12.5°2θ, about 14.1°2θ, about 15.7°2θ, about 16.9°2θ, about 19.1°2θ, about 19.6°2θ, about 21.1°2θ, about 21.9°2θ, about 22.4°2θ, and about 25.8°2θ (e.g., ±0.2°2θ, ±0.1°2θ, or ±0.0°2θ; Cu Kα radiation). In some embodiments, Form II can be characterized by fifteen XRPD peaks selected from about 17.5°2θ, about 9.2°2θ, about 10.0°2θ, about 16.3°2θ, about 18.1°2θ, about 12.5°2θ, about 14.1°2θ, about 15.7°2θ, about 16.9°2θ, about 19.1°2θ, about 19.6°2θ, about 21.1°2θ, about 21.9°2θ, about 22.4°2θ, and about 25.8°2θ (e.g., ±0.2°2θ, ±0.1°2θ, or ±0.0°2θ; Cu Kα radiation).

In some embodiments, Form II can have one, two, three, four, five, six, seven, eight, nine, ten, eleven, twelve, thirteen, fourteen, fifteen, or more, peaks as those listed in Table 2.

TABLE 2

Representative XRPD Peaks for Form II

| Pos. [°2θ] | d-spacing [Å] | Height [cts] | Rel. Int. [%] |
| --- | --- | --- | --- |
| 4.3993 | 20.08591 | 4192.73 | 100 |
| 4.5887 | 19.25723 | 372.57 | 8.89 |
| 6.4181 | 13.77184 | 272.04 | 6.49 |
| 9.1631 | 9.65145 | 604.73 | 14.42 |
| 10.0415 | 8.80905 | 797.62 | 19.02 |
| 12.535 | 7.06175 | 219.78 | 5.24 |
| 14.0927 | 6.28453 | 207.37 | 4.95 |
| 15.696 | 5.64599 | 291.4 | 6.95 |
| 16.3475 | 5.42242 | 894.42 | 21.33 |
| 16.8563 | 5.25988 | 238.29 | 5.68 |
| 17.4614 | 5.07896 | 3465.15 | 82.65 |
| 18.1462 | 4.88879 | 566.6 | 13.51 |
| 19.0801 | 4.65157 | 382.68 | 9.13 |
| 19.6354 | 4.52126 | 297.66 | 7.1 |
| 20.1753 | 4.40146 | 257.13 | 6.13 |
| 21.0851 | 4.21355 | 452.44 | 10.79 |
| 21.9432 | 4.05069 | 498.72 | 11.89 |
| 22.364 | 3.97541 | 478.11 | 11.4 |
| 23.3958 | 3.80237 | 311.59 | 7.43 |
| 23.7066 | 3.75322 | 314.56 | 7.5 |

TABLE 2-continued

Representative XRPD Peaks for Form II

| Pos. [°2θ] | d-spacing [Å] | Height [cts] | Rel. Int. [%] |
|---|---|---|---|
| 25.7619 | 3.45826 | 551.73 | 13.16 |
| 26.7945 | 3.32729 | 370.75 | 8.84 |
| 28.6273 | 3.1183 | 153.79 | 3.67 |
| 32.5932 | 2.74737 | 41.39 | 0.99 |
| 34.1544 | 2.62527 | 68.76 | 1.64 |

Figure 2B:
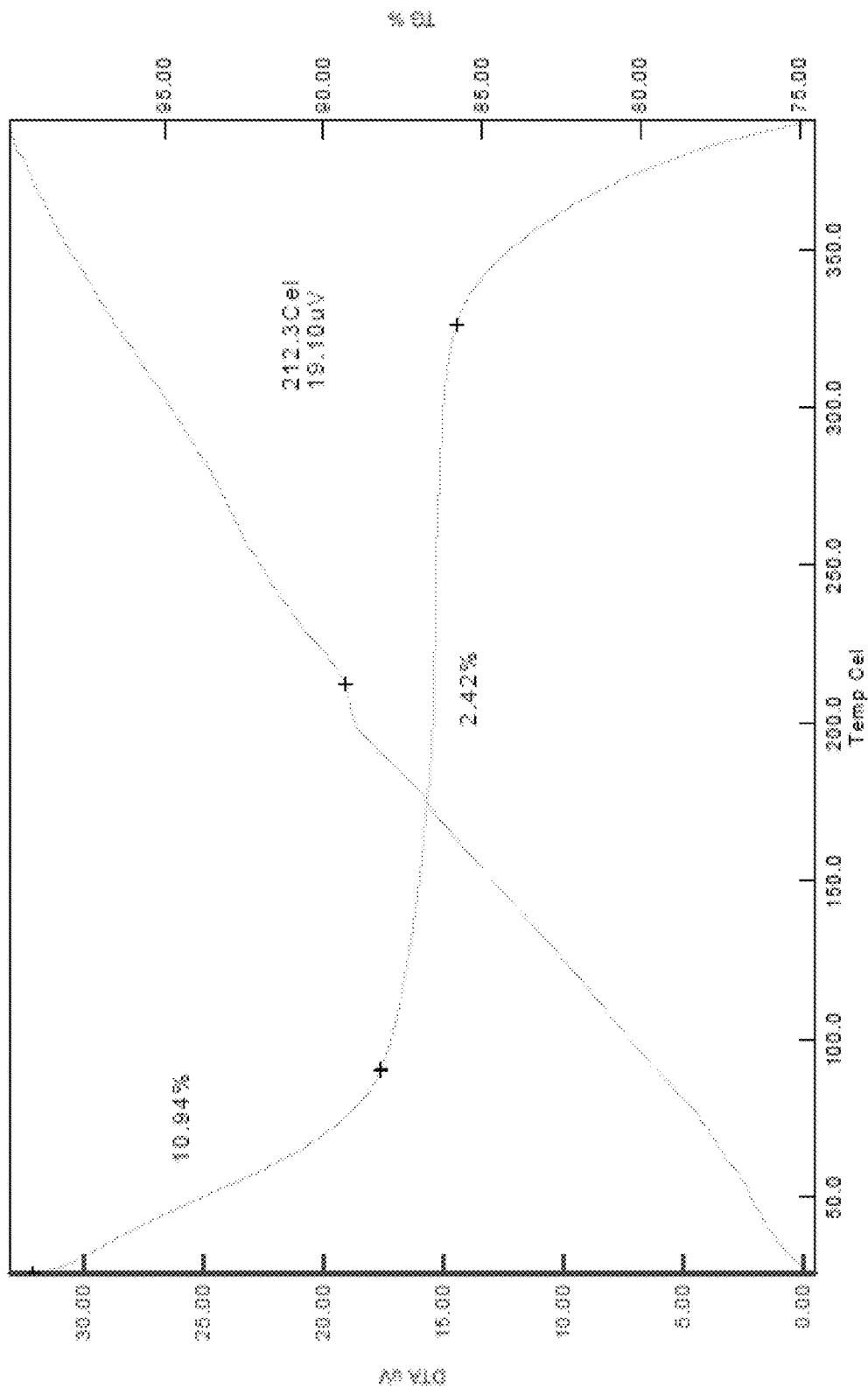
FIG. 2B shows a TG/DT plot of a sample of the Form II polymorph of Compound A. The TG plot begins at the top left, and the DT plot begins at the bottom left.

FIG. 2B is a TG/DT plot of a sample of Form II. TG showed a weight loss of about 11% up to about 85° C., and a further weight loss of 2.4% up to about 325° C. A potential endothermic event can be seen in the DT trace with a peak at about 212° C. In some embodiments, Form II is characterized by a weight loss of about 11% between about 25° C. and about 85° C. In some embodiments, Form II is characterized by an endothermic event, as measured by DT, with a peak at about 212° C. In some embodiments, weight loss is determined by thermogravimetric analysis. In some embodiments, thermogravimetric analysis is conducted substantially as shown in Example 1. In some embodiments, endothermic events are calculated by differential thermal analysis. In some embodiments, differential thermal analysis is conducted substantially as shown in Example 1. In some embodiments, thermogravimetric analysis and differential thermal analysis are conducted simultaneously.

Figure 2C:
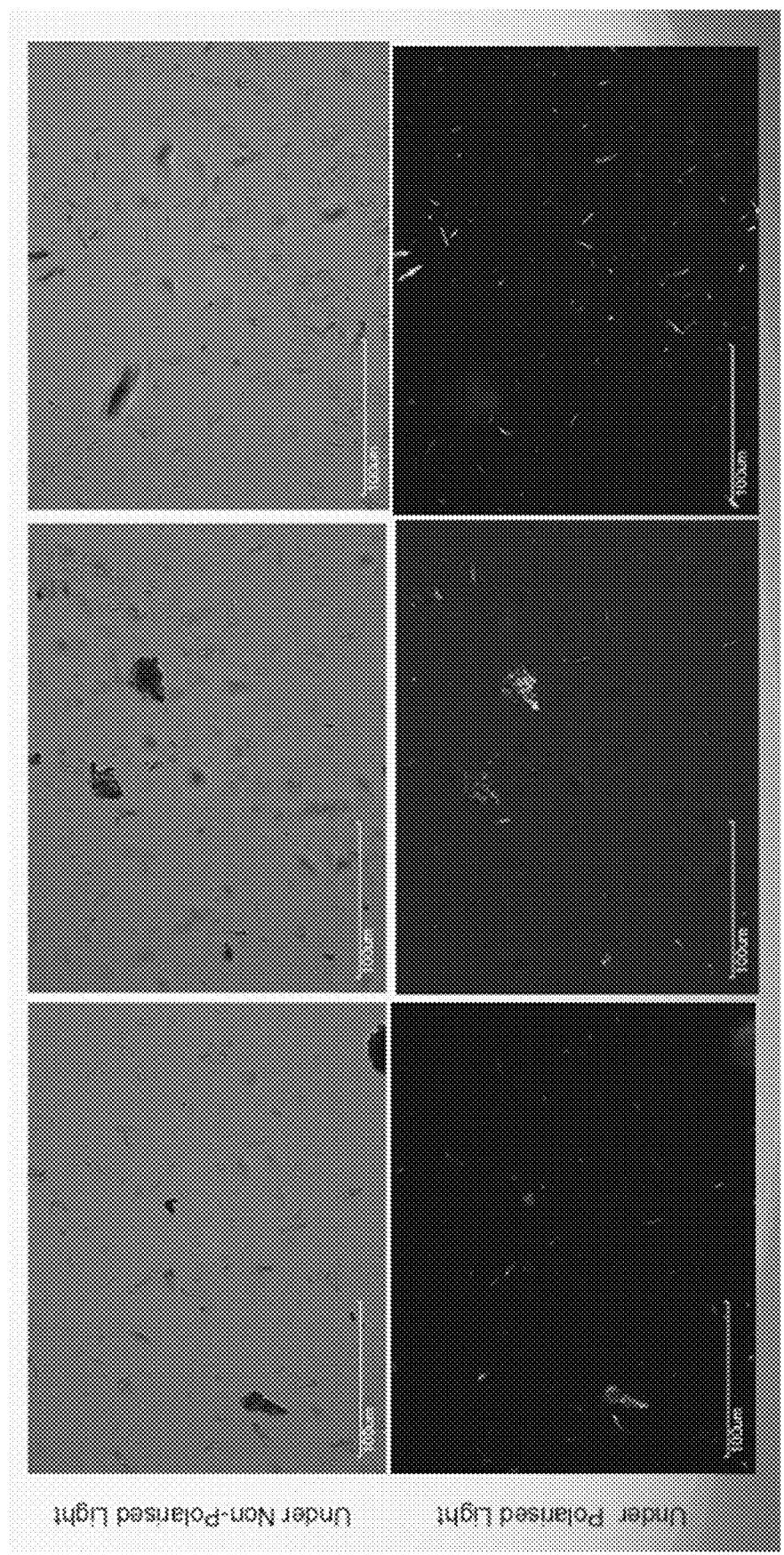
FIG. 2C shows PLM images of the Form II polymorph of Compound A. Samples in this figure were recovered from dichloromethane.

FIG. 2C shows PLM images of Form II, recovered from dichloromethane. PLM indicated the material to be birefringent with irregular, needle-like morphology. In some embodiments, Form II is characterized by birefringent material with irregular, needle-like morphology.

Form III of Compound A can be prepared by crystallization from a number of solvents. For instance, Form III was recovered from acetonitrile by temperature cycling between ambient (about 22° C.) and 40° C. in 4 hour cycles for 72 hours. An XRPD spectrum of Form III, recovered from acetonitrile is shown in FIG. 3A, obtained using Cu Kα radiation.

In some embodiments, this application provides a method of making Form III of Compound A as disclosed herein, comprising recrystallizing Compound A from a solvent. In some embodiments, the solvent is acetonitrile.

Figure 3A:
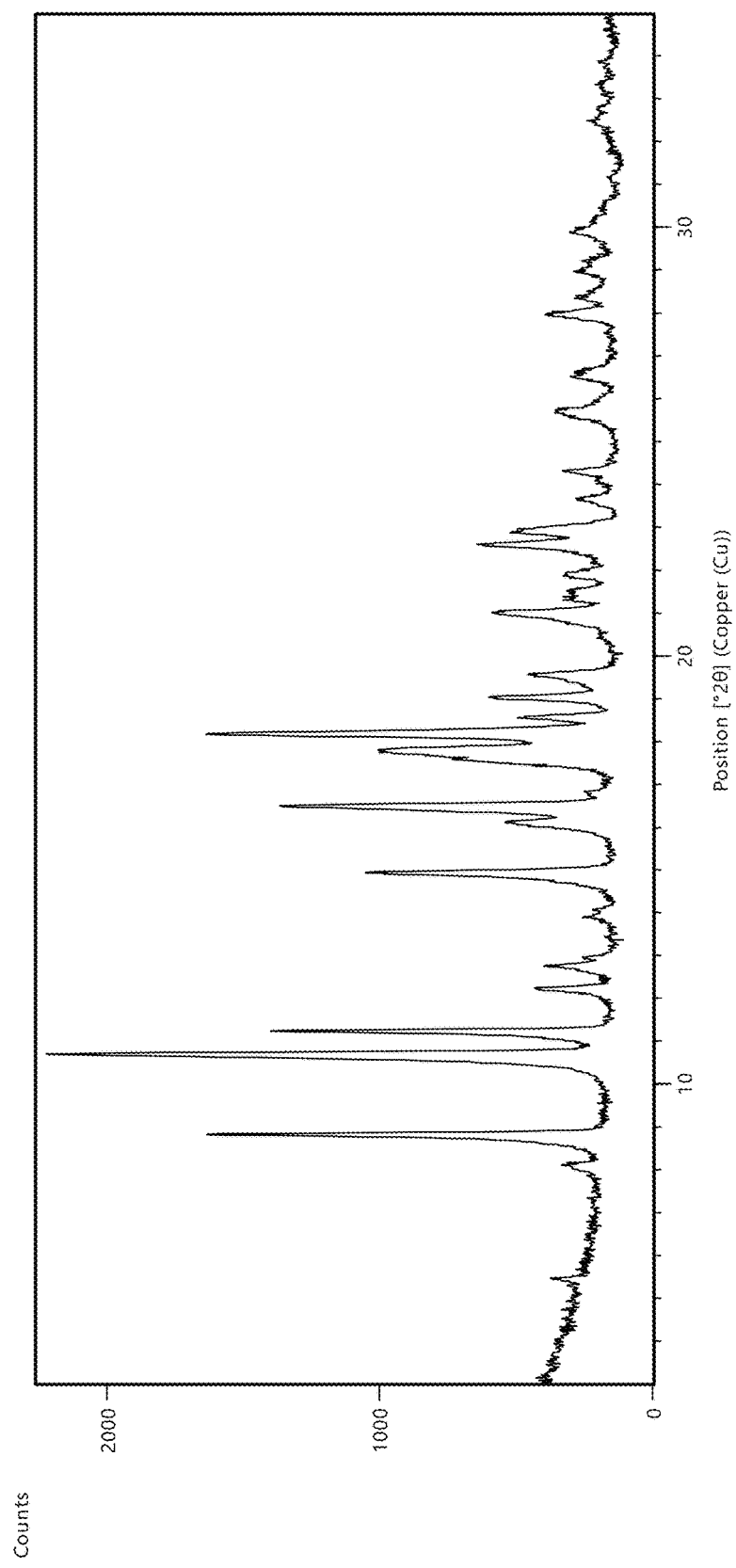
FIG. 3A shows the XRPD spectrum of a sample of the Form III polymorph of Compound A. The diffractogram is from material recovered from acetonitrile.

In some embodiments, Form III can be characterized by the XRPD peaks shown in FIG. 3A. For example, in some embodiments, Form III can be characterized by an XRPD peak at about 10.7°2θ (e.g. 10.7±0.2°2θ, 10.7±0.1°2θ, 10.7±0.0°2θ). In some embodiments, Form III can be further characterized by XRPD peaks at about 8.8°2θ, about 11.2°2θ, about 16.5°2θ, and/or about 18.2°2θ (e.g., ±0.2°2θ, ±0.1°2θ, or ±0.0°2θ; Cu Kα radiation). In some embodiments, Form III can be further characterized by XRPD peaks at about 15.0°2θ, and/or about 17.8°2θ (e.g., ±0.2°2θ, ±0.1°2θ, or ±0.0°2θ; Cu Kα radiation). In some embodiments, Form III can be further characterized by XRPD peaks at about 12.2°2θ, about 12.8°2θ, about 16.1°2θ, about 18.6°2θ, about 19.0°2θ, and/or about 19.6°2θ (e.g., ±0.2°2θ, ±0.1°2θ, or ±0.0°2θ; Cu Kα radiation).

In some embodiments, Form III can be characterized by XRPD peaks at about 8.8°2θ and about 10.7°2θ (e.g., ±0.2°2θ, ±0.1°2θ, or ±0.0°2θ; Cu Kα radiation). In some embodiments, Form III can be characterized by XRPD peaks at about 11.2°2θ and about 10.7°2θ (e.g., ±0.2°2θ, ±0.1°2θ, or ±0.0°2θ; Cu Kα radiation). In some embodiments, Form III can be characterized by XRPD peaks at about 16.5°2θ and about 10.7°2θ (e.g., ±0.2°2θ, ±0.1°2θ, or ±0.0°2θ; Cu Kα radiation). In some embodiments, Form III can be characterized by XRPD peaks at about 18.2°2θ and about 10.7°2θ (e.g., ±0.2°2θ, ±0.1°2θ, or ±0.0°2θ; Cu Kα radiation). In some embodiments, Form III can be characterized by XRPD peaks at about 8.8°2θ, about 11.2°2θ, about 16.5°2θ, about 18.2°2θ, and about 10.7°2θ (e.g., ±0.2°2θ, ±0.1°2θ, or ±0.0°2θ; Cu Kα radiation).

In some embodiments, Form III can be characterized by XRPD peaks at about 8.8°2θ, about 16.5°2θ, and about 11.2°2θ (e.g., ±0.2°2θ, ±0.1°2θ, or ±0.0°2θ; Cu Kα radiation). In some embodiments, Form III can be characterized by XRPD peaks at about 18.2°2θ, about 16.5°2θ, and about 11.2°2θ (e.g., ±0.2°2θ, ±0.1°2θ, or ±0.0°2θ; Cu Kα radiation). In some embodiments, Form III can be characterized by XRPD peaks at about 18.2°2θ, about 8.8°2θ, and about 11.2°2θ (e.g., ±0.2°2θ, ±0.1°2θ, or ±0.0°2θ; Cu Kα radiation). In some embodiments, Form III can be characterized by XRPD peaks at about 18.2°2θ, about 8.8°2θ, and about 16.5°2θ (e.g., ±0.2°2θ, ±0.1°2θ, or ±0.0°2θ; Cu Kα radiation). In some embodiments, Form III can be characterized by XRPD peaks at about 10.7°2θ, about 16.5°2θ, and about 11.2°2θ (e.g., ±0.2°2θ, ±0.1°2θ, or ±0.0°2θ; Cu Kα radiation). In some embodiments, Form III can be characterized by XRPD peaks at about 10.7°2θ, about 8.8°2θ, and about 11.2°2θ (e.g., ±0.2°2θ, ±0.1°2θ, or ±0.0°2θ; Cu Kα radiation). In some embodiments, Form III can be characterized by XRPD peaks at about 10.7°2θ, about 8.8°2θ, and about 16.5°2θ (e.g., ±0.2°2θ, ±0.1°2θ, or ±0.0°2θ; Cu Kα radiation). In some embodiments, Form III can be characterized by XRPD peaks at about 10.7°2θ, about 18.2°2θ, and about 11.2°2θ (e.g., ±0.2°2θ, ±0.1°2θ, or ±0.0°2θ; Cu Kα radiation). In some embodiments, Form III can be characterized by XRPD peaks at about 10.7°2θ, about 18.2°2θ, and about 16.5°2θ (e.g., ±0.2°2θ, ±0.1°2θ, or ±0.0°2θ; Cu Kα radiation). In some embodiments, Form III can be characterized by XRPD peaks at about 10.7°2θ, about 18.2°2θ, and about 8.8°2θ (e.g., ±0.2°2θ, ±0.1°2θ, or ±0.0°2θ; Cu Kα radiation).

In some embodiments, Form III can be characterized by XRPD peaks at about 18.2°2θ, about 8.8°2θ, about 16.5°2θ, and about 11.2°2θ (e.g., ±0.2°2θ, ±0.1°2θ, or ±0.0°2θ; Cu Kα radiation). In some embodiments, Form III can be characterized by XRPD peaks at about 10.7°2θ, about 8.8°2θ, about 16.5°2θ, and about 11.2°2θ (e.g., ±0.2°2θ, ±0.1°2θ, or ±0.0°2θ; Cu Kα radiation). In some embodiments, Form III can be characterized by XRPD peaks at about 10.7°2θ, about 18.2°2θ, about 16.5°2θ, and about 11.2°2θ (e.g., ±0.2°2θ, ±0.1°2θ, or ±0.0°2θ; Cu Kα radiation). In some embodiments, Form III can be characterized by XRPD peaks at about 10.7°2θ, about 18.2°2θ, about 8.8°2θ, and about 11.2°2θ (e.g., ±0.2°2θ, ±0.1°2θ, or ±0.0°2θ; Cu Kα radiation). In some embodiments, Form III can be characterized by XRPD peaks at about 10.7°2θ, about 18.2°2θ, about 8.8°2θ, and about 16.5°2θ (e.g., ±0.2°2θ, ±0.1°2θ, or ±0.0°2θ; Cu Kα radiation).

In some embodiments, Form III can be characterized by XRPD peaks at about 8.8°2θ, about 11.2°2θ, about 16.5°2θ, about 18.2°2θ, about 10.7°2θ, and about 15.0°2θ (e.g., ±0.2°2θ, ±0.1°2θ, or ±0.0°2θ; Cu Kα radiation). In some embodiments, Form III can be characterized by XRPD peaks at about 8.8°2θ, about 11.2°2θ, about 16.5°2θ, about 18.2°2θ, about 10.7°2θ, and about 17.8°2θ (e.g., ±0.2°2θ, ±0.1°2θ, or ±0.0°2θ; Cu Kα radiation). In some embodiments, Form III can be characterized by XRPD peaks at about 8.8°2θ, about 11.2°2θ, about 16.5°2θ, about 18.2°2θ, about 10.7°2θ, about 17.8°2θ, and about 15.0°2θ (e.g., ±0.2°2θ, ±0.1°2θ, or ±0.0°2θ; Cu Kα radiation).

In some embodiments, Form III can be characterized by XRPD peaks at about 8.8°2θ, about 11.2°2θ, about 16.5°2θ, about 18.2°2θ, about 10.7°2θ, about 17.8°2θ, about 15.0°2θ, and about 12.2°2θ (e.g., ±0.2°2θ, ±0.1°2θ, or ±0.0°2θ; Cu Kα radiation). In some embodiments, Form III can be characterized by XRPD peaks at about 8.8°2θ, about 11.2°2θ, about 16.5°2θ, about 18.2°2θ, about 10.7°2θ, about 17.8°2θ, about 15.0°2θ, and about 12.8°2θ (e.g., ±0.2°2θ, ±0.1°2θ, or ±0.0°2θ; Cu Kα radiation). In some embodiments, Form III can be characterized by XRPD peaks at about 8.8°2θ, about 11.2°2θ, about 16.5°2θ, about 18.2°2θ, about 10.7°2θ, about 17.8°2θ, about 15.0°2θ, and about 16.1°2θ (e.g., ±0.2°2θ, ±0.1°2θ, or ±0.0°2θ; Cu Kα radiation). In some embodiments, Form III can be characterized by XRPD peaks at about 8.8°2θ, about 11.2°2θ, about 16.5°2θ, about 18.2°2θ, about 10.7°2θ, about 17.8°2θ, about 15.0°2θ, and about 18.6°2θ (e.g., ±0.2°2θ, ±0.1°2θ, or ±0.0°2θ; Cu Kα radiation). In some embodiments, Form III can be characterized by XRPD peaks at about 8.8°2θ, about 11.2°2θ, about 16.5°2θ, about 18.2°2θ, about 10.7°2θ, about 17.8°2θ, about 15.0°2θ, and about 19.0°2θ (e.g., ±0.2°2θ, ±0.1°2θ, or ±0.0°2θ; Cu Kα radiation). In some embodiments, Form III can be characterized by XRPD peaks at about 8.8°2θ, about 11.2°2θ, about 16.5°2θ, about 18.2°2θ, about 10.7°2θ, about 17.8°2θ, about 15.0°2θ, and about 19.6°2θ (e.g., ±0.2°2θ, ±0.1°2θ, or ±0.0°2θ; Cu Kα radiation). In some embodiments, Form III can be characterized by XRPD peaks at about 8.8°2θ, about 11.2°2θ, about 16.5°2θ, about 18.2°2θ, about 10.7°2θ, about 17.8°2θ, about 15.0°2θ, about 12.2°2θ, about 12.8°2θ, about 16.1°2θ, about 18.6°2θ, about 19.0°2θ, and about 19.6°20 (e.g., ±0.2°2θ, ±0.1°2θ, or ±0.0°2θ; Cu Kα radiation).

In some embodiments, Form III can be characterized by one or more XRPD peaks selected from about 8.8°2θ, about 11.2°2θ, about 16.5°2θ, about 18.2°2θ, about 10.7°2θ, about 17.8°2θ, about 15.0°2θ, about 12.2°2θ, about 12.8°2θ, about 16.1°2θ, about 18.6°2θ, about 19.0°2θ, and about 19.6°2θ (e.g., ±0.2°2θ, ±0.1°2θ, or ±0.0°2θ; Cu Kα radiation). In some embodiments, Form III can be characterized by one XRPD peaks selected from about 8.8°2θ, about 11.2°2θ, about 16.5°2θ, about 18.2°2θ, about 10.7°2θ, about 17.8°2θ, about 15.0°2θ, about 12.2°2θ, about 12.8°2θ, about 16.1°2θ, about 18.6°2θ, about 19.0°2θ, and about 19.6°2θ (e.g., ±0.2°2θ, ±0.1°2θ, or ±0.0°2θ; Cu Kα radiation). In some embodiments, Form III can be characterized by two XRPD peaks selected from about 8.8°2θ, about 11.2°2θ, about 16.5°2θ, about 18.2°2θ, about 10.7°2θ, about 17.8°2θ, about 15.0°2θ, about 12.2°2θ, about 12.8°2θ, about 16.1°2θ, about 18.6°2θ, about 19.0°2θ, and about 19.6°2θ (e.g., ±0.2°2θ, ±0.1°2θ, or ±0.0°2θ; Cu Kα radiation). In some embodiments, Form III can be characterized by three XRPD peaks selected from about 8.8°2θ, about 11.2°2θ, about 16.5°2θ, about 18.2°2θ, about 10.7°2θ, about 17.8°2θ, about 15.0°2θ, about 12.2°2θ, about 12.8°2θ, about 16.1°2θ, about 18.6°2θ, about 19.0°2θ, and about 19.6°2θ (e.g., ±0.2°2θ, ±0.1°2θ, or ±0.0°2θ; Cu Kα radiation). In some embodiments, Form III can be characterized by four XRPD peaks selected from about 8.8°2θ, about 11.2°2θ, about 16.5°2θ, about 18.2°2θ, about 10.7°2θ, about 17.8°2θ, about 15.0°2θ, about 12.2°2θ, about 12.8°2θ, about 16.1°2θ, about 18.6°2θ, about 19.0°2θ, and about 19.6°2θ (e.g., ±0.2°2θ, ±0.1°2θ, or ±0.0°2θ; Cu Kα radiation). In some embodiments, Form III can be characterized by five XRPD peaks selected from about 8.8°2θ, about 11.2°2θ, about 16.5°2θ, about 18.2°2θ, about 10.7°2θ, about 17.8°2θ, about 15.0°2θ, about 12.2°2θ, about 12.8°2θ, about 16.1°2θ, about 18.6°2θ, about 19.0°2θ, and about 19.6°2θ (e.g., ±0.2°2θ, ±0.1°2θ, or ±0.0°2θ; Cu Kα radiation). In some embodiments, Form III can be characterized by six XRPD peaks selected from about 8.8°2θ, about 11.2°2θ, about 16.5°2θ, about 18.2°2θ, about 10.7°2θ, about 17.8°2θ, about 15.0°2θ, about 12.2°2θ, about 12.8°2θ, about 16.1°2θ, about 18.6°2θ, about 19.0°2θ, and about 19.6°20 (e.g., ±0.2°2θ, ±0.1°2θ, or ±0.0°2θ; Cu Kα radiation). In some embodiments, Form III can be characterized by seven XRPD peaks selected from about 8.8°2θ, about 11.2°2θ, about 16.5°2θ, about 18.2°2θ, about 10.7°2θ, about 17.8°2θ, about 15.0°2θ, about 12.2°2θ, about 12.8°2θ, about 16.1°2θ, about 18.6°2θ, about 19.0°2θ, and about 19.6°2θ (e.g., ±0.2°2θ, ±0.1°2θ, or ±0.0°2θ; Cu Kα radiation). In some embodiments, Form III can be characterized by eight XRPD peaks selected from about 8.8°2θ, about 11.2°2θ, about 16.5°2θ, about 18.2°2θ, about 10.7°2θ, about 17.8°2θ, about 15.0°2θ, about 12.2°2θ, about 12.8°2θ, about 16.1°2θ, about 18.6°2θ, about 19.0°2θ, and about 19.6°2θ (e.g., ±0.2°2θ, ±0.1°2θ, or ±0.0°2θ; Cu Kα radiation). In some embodiments, Form III can be characterized by nine XRPD peaks selected from about 8.8°2θ, about 11.2°2θ, about 16.5°2θ, about 18.2°2θ, about 10.7°2θ, about 17.8°2θ, about 15.0°2θ, about 12.2°2θ, about 12.8°2θ, about 16.1°2θ, about 18.6°2θ, about 19.0°2θ, and about 19.6°2θ (e.g., ±0.2°2θ, ±0.1°2θ, or ±0.0°2θ; Cu Kα radiation). In some embodiments, Form III can be characterized by ten XRPD peaks selected from about 8.8°2θ, about 11.2°2θ, about 16.5°2θ, about 18.2°2θ, about 10.7°2θ, about 17.8°2θ, about 15.0°2θ, about 12.2°2θ, about 12.8°2θ, about 16.1°2θ, about 18.6°2θ, about 19.0°2θ, and about 19.6°2θ (e.g., ±0.2°2θ, ±0.1°2θ, or ±0.0°2θ; Cu Kα radiation). In some embodiments, Form III can be characterized by eleven XRPD peaks selected from about 8.8°2θ, about 11.2°2θ, about 16.5°2θ, about 18.2°2θ, about 10.7°2θ, about 17.8°2θ, about 15.0°2θ, about 12.2°2θ, about 12.8°2θ, about 16.1°2θ, about 18.6°2θ, about 19.0°2θ, and about 19.6°2θ (e.g., ±0.2°2θ, ±0.1°2θ, or ±0.0°2θ; Cu Kα radiation). In some embodiments, Form III can be characterized by twelve XRPD peaks selected from about 8.8°2θ, about 11.2°2θ, about 16.5°2θ, about 18.2°2θ, about 10.7°2θ, about 17.8°2θ, about 15.0°2θ, about 12.2°2θ, about 12.8°2θ, about 16.1°2θ, about 18.6°2θ, about 19.0°2θ, and about 19.6°2θ (e.g., ±0.2°2θ, ±0.1°2θ, or ±0.0°2θ; Cu Kα radiation). In some embodiments, Form III can be characterized by thirteen XRPD peaks selected from about 8.8°2θ, about 11.2°2θ, about 16.5°2θ, about 18.2°2θ, about 10.7°2θ, about 17.8°2θ, about 15.0°2θ, about 12.2°2θ, about 12.8°2θ, about 16.1°2θ, about 18.6°2θ, about 19.0°2θ, and about 19.6°2θ (e.g., ±0.2°2θ, ±0.1°2θ, or ±0.0°2θ; Cu Kα radiation).

In some embodiments, Form III can have one, two, three, four, five, six, seven, eight, nine, ten, eleven, twelve, thirteen, or more, peaks as those listed in Table 3.

TABLE 3

Representative XRPD Peaks for Form III

| Pos. [°2θ] | d-spacing [Å] | Height [cts] | Rel. Int. [%] |
|---|---|---|---|
| 5.4531 | 16.20675 | 101.07 | 5.09 |
| 8.1336 | 10.87066 | 104.5 | 5.26 |
| 8.8352 | 10.00885 | 1474.81 | 74.3 |
| 10.7102 | 8.2605 | 1984.99 | 100 |
| 11.2451 | 7.86873 | 1213.42 | 61.13 |
| 12.2482 | 7.2265 | 272.28 | 13.72 |
| 12.7621 | 6.93663 | 233.09 | 11.74 |

TABLE 3-continued

Representative XRPD Peaks for Form III

| Pos. [°2θ] | d-spacing [Å] | Height [cts] | Rel. Int. [%] |
|---|---|---|---|
| 13.9002 | 6.37112 | 70.06 | 3.53 |
| 14.9619 | 5.92133 | 870.45 | 43.85 |
| 16.107 | 5.50285 | 382.6 | 19.27 |
| 16.4976 | 5.37343 | 1251.27 | 63.04 |
| 17.5241 | 5.06091 | 475.29 | 23.94 |
| 17.8427 | 4.97127 | 777.87 | 39.19 |
| 18.1792 | 4.88001 | 1488.7 | 75 |
| 18.5927 | 4.7724 | 282.06 | 14.21 |
| 19.046 | 4.65982 | 453.18 | 22.83 |
| 19.5738 | 4.53535 | 307.85 | 15.51 |
| 20.9935 | 4.23174 | 436.51 | 21.99 |
| 21.5081 | 4.13164 | 161.13 | 8.12 |
| 21.8598 | 4.06596 | 171.47 | 8.64 |
| 22.5492 | 3.94318 | 483.91 | 24.38 |
| 22.8843 | 3.88619 | 370.11 | 18.65 |
| 23.6552 | 3.76127 | 129.27 | 6.51 |
| 24.3132 | 3.66094 | 181.79 | 9.16 |
| 25.7288 | 3.46264 | 205.87 | 10.37 |
| 26.5503 | 3.35734 | 139.43 | 7.02 |
| 27.972 | 3.18984 | 249.58 | 12.57 |
| 28.3766 | 3.14528 | 133.45 | 6.72 |
| 28.9584 | 3.08339 | 140.89 | 7.1 |
| 29.8684 | 2.99149 | 167.81 | 8.45 |
| 32.4751 | 2.75709 | 74.69 | 3.76 |

Figure 3B:
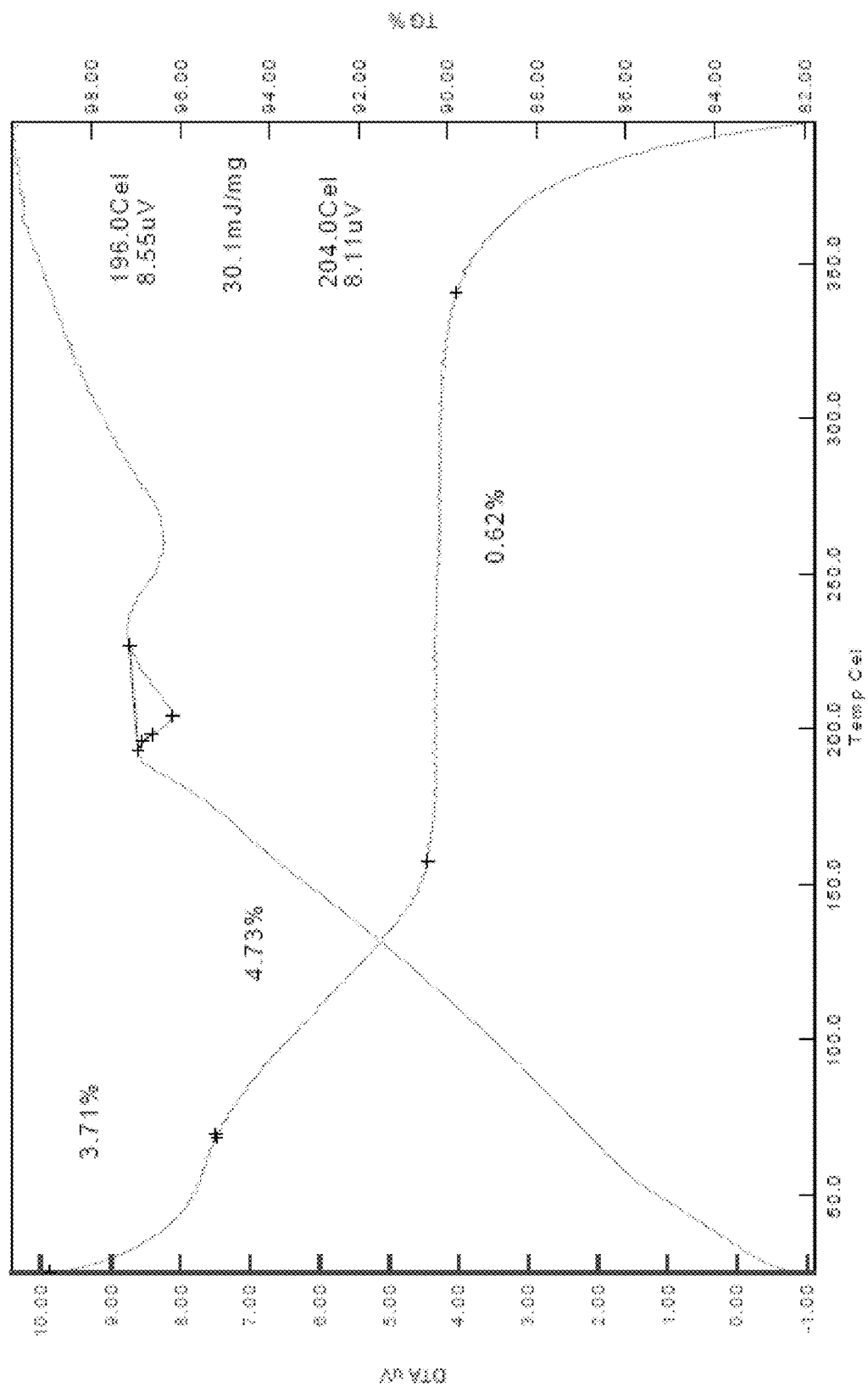
FIG. 3B shows a TG/DT plot of a sample of the Form III polymorph of Compound A. The TG plot begins at the top left, and the DT plot begins at the bottom left.

FIG. 3B is a TG/DT plot of a sample of Form III. TG showed a weight loss of about 3.7% up to about 75° C., a further weight loss of 4.7% up to about 160° C. and a final weight loss of 0.6% up to 350° C. A small, broad endothermic event was noted in the DT with an onset of about 196° C. with a peak at about 204° C. In some embodiments, Form III is characterized by a weight loss of about 3.7% between about 25° C. and about 75° C. In some embodiments, Form III is further characterized by a weight loss of about 4.7% between about 75° C. and about 160° C. In some embodiments, Form III is further characterized by a weight loss of about 0.6% between about 160° C. and about 350° C. In some embodiments, Form III is characterized by an endothermic event, as measured by DT, with an onset of about 196° C. In some embodiments, Form III is characterized by an endothermic event, as measured by DT, with a peak at about 204° C. In some embodiments, Form III is characterized by an endothermic event, as measured by DT, with an onset of about 196° C. and a peak at about 204° C. In some embodiments, weight loss is determined by thermogravimetric analysis. In some embodiments, thermogravimetric analysis is conducted substantially as shown in Example 1. In some embodiments, endothermic events are calculated by differential thermal analysis. In some embodiments, differential thermal analysis is conducted substantially as shown in Example 1. In some embodiments, thermogravimetric analysis and differential thermal analysis are conducted simultaneously.

Figure 3C:
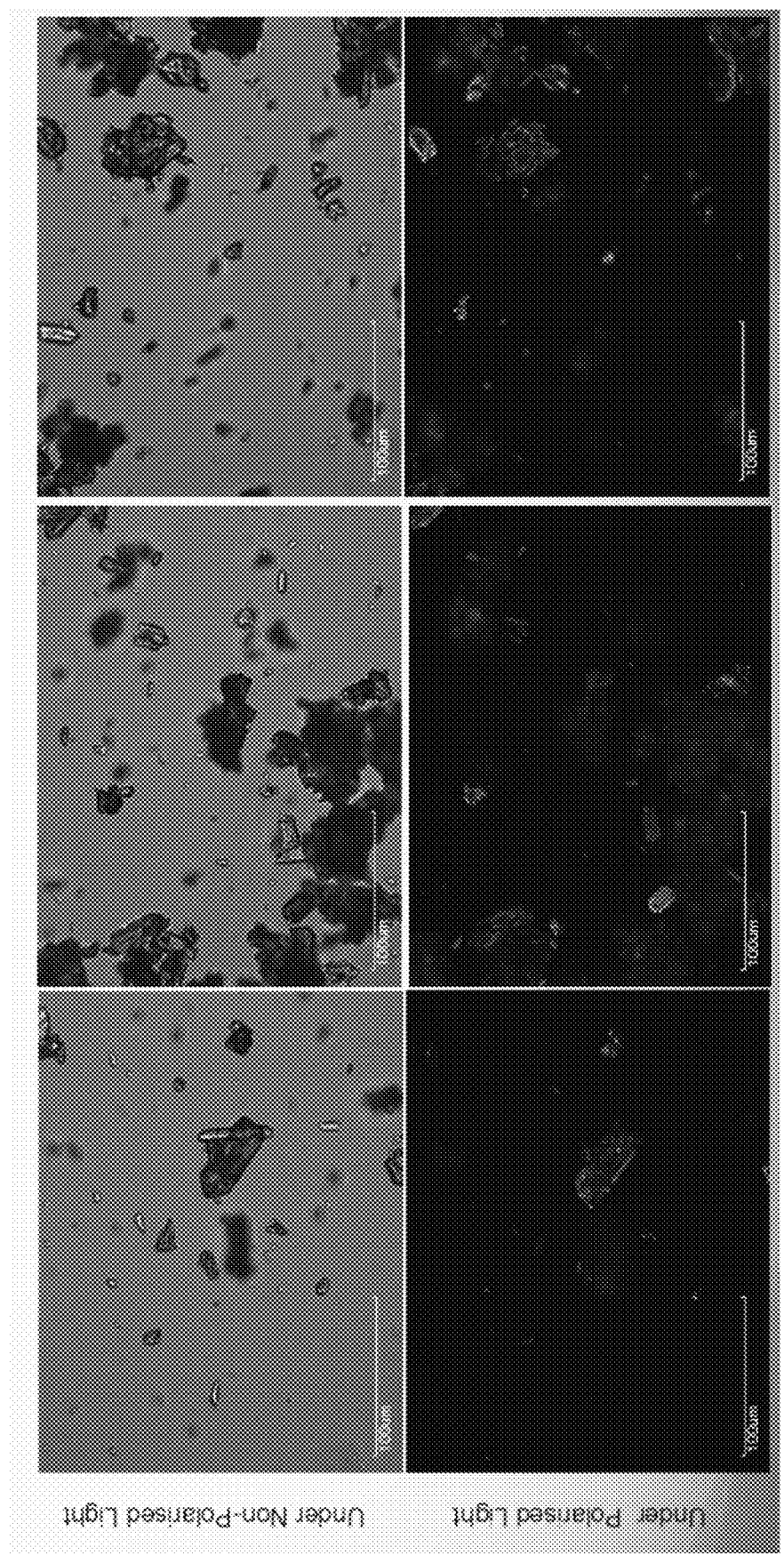
FIG. 3C shows PLM images of the Form III polymorph of Compound A. Samples in this figure were recovered from acetonitrile.

FIG. 3C shows PLM images of Form III, recovered from acetonitrile. PLM indicated the material to be birefringent with irregular, lath-like morphology. In some embodiments, Form III is characterized by birefringent material with irregular, lath-like morphology.

Form IV of Compound A can be prepared by crystallization from a number of conditions. For instance, Form IV was recovered from dichloromethane/methanol (25:75 v/v) upon anti-solvent addition of tert-butyl methyl ether, and from dichloromethane/methanol (25:75 v/v) upon crash-cooling at 2-8° C. An XRPD spectrum of Form IV, recovered from dichloromethane/methanol (25:75) after crash cooling is shown in FIG. 4A, obtained using Cu Kα radiation.

In some embodiments, this application provides a method of making Form IV of Compound A as disclosed herein, comprising crash-cooling Compound A from a solvent. In some embodiments, the solvent is a mixture of dichloromethane and methanol. In some embodiments, the present disclosure provides a method of making the Form IV polymorph of Compound A, comprising addition of an anti-solvent to a solution of Compound A from a solvent. In some embodiments, the solvent comprises a mixture of dichloromethane and methanol. In some embodiments, the anti-solvent is tert-butyl methyl ether.

Figure 4A:
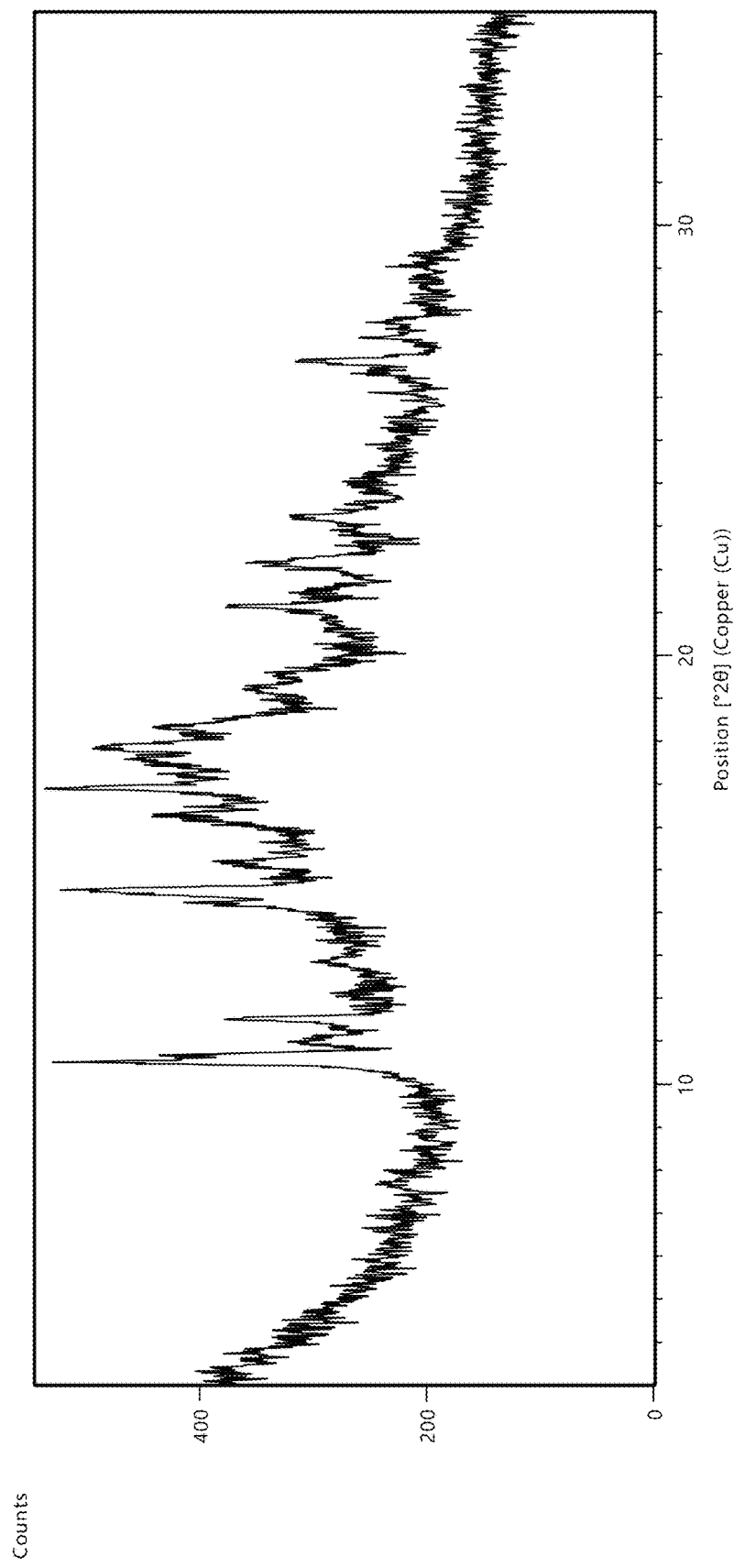
FIG. 4A shows the XRPD spectrum of a sample of the Form IV polymorph of Compound A. The diffractogram is from material recovered from dichloromethane:methanol (25:75 v/v) after crash cooling.

In some embodiments, Form IV can be characterized by the XRPD peaks shown in FIG. 4A. For example, in some embodiments, Form IV can be characterized by an XRPD peak at about 10.5°2θ (e.g. 10.5±0.2°2θ, 10.5±0.1°2θ, 10.5±0.0°2θ). In some embodiments, Form IV can be further characterized by XRPD peaks at about 14.5°2θ, and/or about 16.9°2θ (e.g., ±0.2°2θ, ±0.1°2θ, or ±0.0°2θ; Cu Kα radiation). In some embodiments, Form IV can be further characterized by XRPD peaks at about 11.5°2θ, about 14.2°2θ, and/or about 16.3°2θ (e.g., ±0.2°2θ, ±0.1°2θ, or ±0.0°2θ; Cu Kα radiation).

In some embodiments, Form IV can be characterized by XRPD peaks at about 14.5°2θ and about 10.5°2θ (e.g., ±0.2°2θ, ±0.1°2θ, or ±0.0°2θ; Cu Kα radiation). In some embodiments, Form IV can be characterized by XRPD peaks at about 16.9°2θ and about 10.5°2θ (e.g., ±0.2°2θ, ±0.1°2θ, or ±0.0°2θ; Cu Kα radiation). In some embodiments, Form IV can be characterized by XRPD peaks at about 14.5°2θ, about 16.9°2θ, and about 10.5°2θ (e.g., ±0.2°2θ, ±0.1°2θ, or ±0.0°2θ; Cu Kα radiation).

In some embodiments, Form IV can be characterized by XRPD peaks at about 14.5°2θ, about 16.9°2θ, about 10.5°2θ, and about 11.5°2θ (e.g., ±0.2°2θ, ±0.1°2θ, or ±0.0°2θ; Cu Kα radiation). In some embodiments, Form IV can be characterized by XRPD peaks at about 14.5°2θ, about 16.9°2θ, about 10.5°2θ, and about 14.2°2θ (e.g., ±0.2°2θ, ±0.1°2θ, or ±0.0°2θ; Cu Kα radiation). In some embodiments, Form IV can be characterized by XRPD peaks at about 14.5°2θ, about 16.9°2θ, about 10.5°2θ, and about 16.3°2θ (e.g., ±0.2°2θ, ±0.1°2θ, or ±0.0°2θ; Cu Kα radiation). In some embodiments, Form IV can be characterized by XRPD peaks at about 14.5°2θ, about 16.9°2θ, about 10.5°2θ, about 11.5°2θ, about 14.2°2θ, and about 16.3°2θ (e.g., ±0.2°2θ, ±0.1°2θ, or ±0.0°2θ; Cu Kα radiation).

In some embodiments, Form IV can be characterized by one or more XRPD peaks selected from at about 14.5°2θ, about 16.9°2θ, about 10.5°2θ, about 11.5°2θ, about 14.2°2θ, about 16.3°2θ, and about 17.8°2θ (e.g., ±0.2°2θ, ±0.1°2θ, or ±0.0°2θ; Cu Kα radiation). In some embodiments, Form IV can be characterized by one XRPD peak selected from at about 14.5°2θ, about 16.9°2θ, about 10.5°2θ, about 11.5°2θ, about 14.2°2θ, about 16.3°2θ, and about 17.8°2θ (e.g., ±0.2°2θ, ±0.1°2θ, or ±0.0°2θ; Cu Kα radiation). In some embodiments, Form IV can be characterized by two XRPD peaks selected from at about 14.5°2θ, about 16.9°2θ, about 10.5°2θ, about 11.5°2θ, about 14.2°2θ, about 16.3°2θ, and about 17.8°2θ (e.g., ±0.2°2θ, ±0.1°2θ, or ±0.0°2θ; Cu Kα radiation). In some embodiments, Form IV can be characterized by three XRPD peaks selected from at about 14.5°2θ, about 16.9°2θ, about 10.5°2θ, about 11.5°2θ, about 14.2°2θ, about 16.3°2θ, and about 17.8°2θ (e.g., ±0.2°2θ, ±0.1°2θ, or ±0.0°2θ; Cu Kα radiation). In some embodiments, Form IV can be characterized by four XRPD peaks selected from at about 14.5°2θ, about 16.9°2θ, about 10.5°2θ, about 11.5°2θ, about 14.2°2θ, about 16.3°2θ, and about 17.8°2θ (e.g., ±0.2°2θ, ±0.1°2θ, or ±0.0°2θ; Cu Kα radiation). In some embodiments, Form IV can be characterized by five XRPD peaks selected from at about 14.5°2θ, about 16.9°2θ, about 10.5°2θ, about 11.5°2θ, about 14.2°2θ, about 16.3°2θ, and about 17.8°2θ (e.g., ±0.2°2θ, ±0.1°2θ, or ±0.0°2θ; Cu Kα radiation). In some embodiments, Form IV can be characterized by six XRPD peaks selected from at about 14.5°2θ, about 16.9°2θ, about 10.5°2θ, about 11.5°2θ, about 14.2°2θ, about 16.3°2θ, and about 17.8°2θ (e.g., ±0.2°2θ, ±0.1°2θ, or ±0.0°2θ; Cu Kα radiation). In some embodiments, Form IV can be characterized by seven XRPD peaks selected from at about 14.5°2θ, about 16.9°2θ, about 10.5°2θ, about 11.5°2θ, about 14.2°2θ, about 16.3°2θ, and about 17.8°2θ (e.g., ±0.2°2θ, ±0.1°2θ, or ±0.0°2θ; Cu Kα radiation).

In some embodiments, Form IV can have one, two, three, four, five, six, seven, or more, peaks as those listed in Table 4.

TABLE 4

Representative XRPD Peaks for Form IV

| Pos. [°2θ] | d-spacing [Å] | Height [cts] | Rel. Int. [%] |
|---|---|---|---|
| 10.5178 | 8.41116 | 304.56 | 93.44 |
| 10.9677 | 8.06049 | 90.46 | 27.75 |
| 11.536 | 7.67099 | 174.66 | 53.58 |
| 12.067 | 7.32848 | 57.24 | 17.56 |
| 12.8578 | 6.88519 | 87.63 | 26.89 |
| 14.2011 | 6.23162 | 153.19 | 47 |
| 14.5487 | 6.08856 | 304.24 | 93.34 |
| 15.1581 | 5.84513 | 169.85 | 52.11 |
| 16.2505 | 5.45459 | 212.18 | 65.1 |
| 16.4646 | 5.37969 | 141.31 | 43.35 |
| 16.9005 | 5.24625 | 325.95 | 100 |
| 17.1436 | 5.16811 | 168.19 | 51.6 |
| 17.5963 | 5.03616 | 190.98 | 58.59 |
| 17.802 | 4.98255 | 275.09 | 84.4 |
| 18.243 | 4.85906 | 183.29 | 56.23 |
| 19.1699 | 4.62997 | 135.3 | 41.51 |
| 21.1341 | 4.20391 | 161.35 | 49.5 |
| 21.4441 | 4.14039 | 74.71 | 22.92 |
| 22.1661 | 4.01046 | 124.88 | 38.31 |
| 23.1962 | 3.83463 | 95.81 | 29.39 |
| 23.9339 | 3.71502 | 35.94 | 11.03 |
| 26.8492 | 3.32063 | 121.82 | 37.37 |
| 27.6242 | 3.22921 | 36.96 | 11.34 |
| 29.0165 | 3.07735 | 26.3 | 8.07 |

Figure 4B:
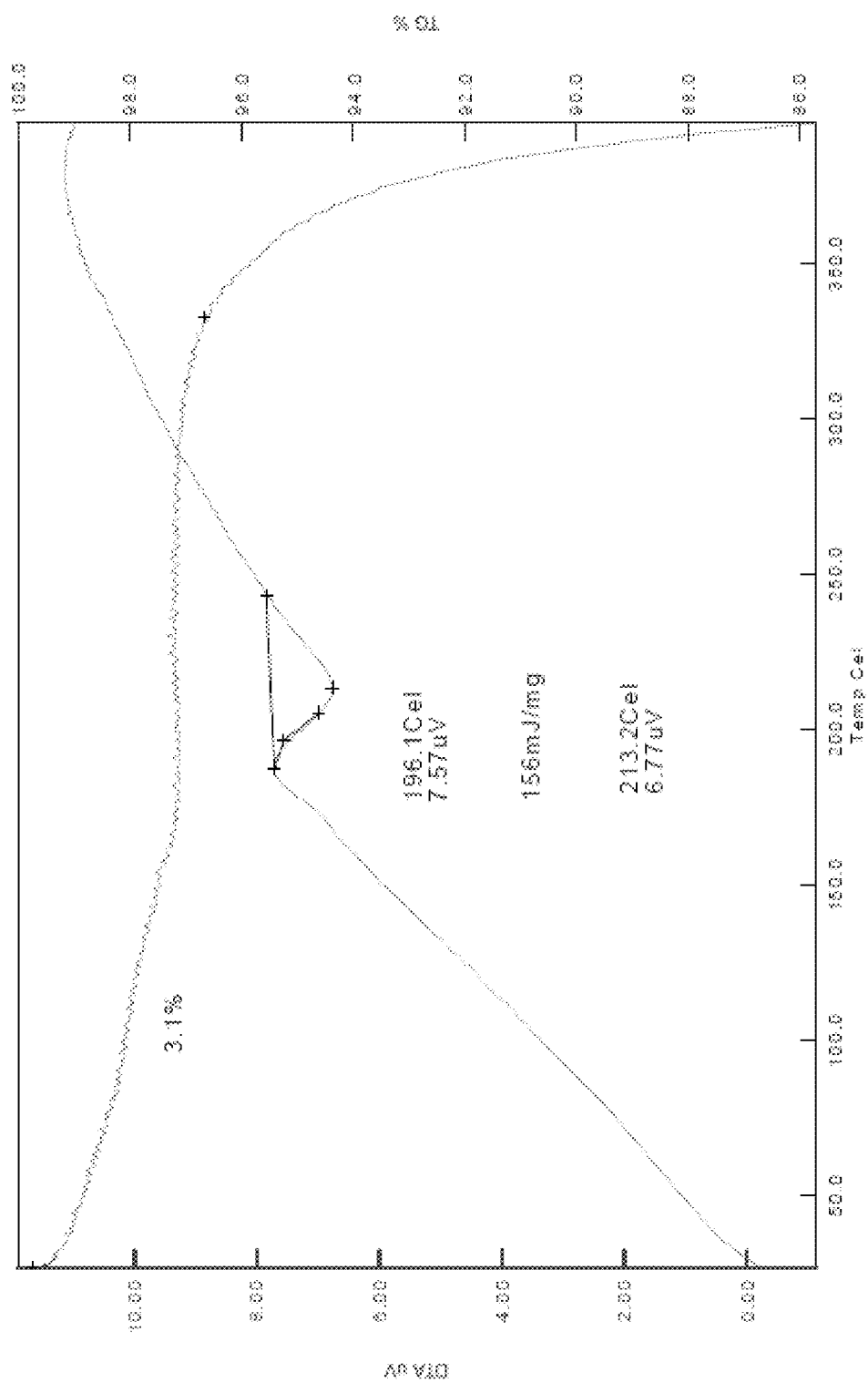
FIG. 4B shows a shows a TG/DT plot of a sample of the Form IV polymorph of Compound A. The TG plot begins at the top left, and the DT plot begins at the bottom left.

FIG. 4B is a TG/DT plot of a sample of Form IV. TG showed a weight loss of about 3.1% up to about 350° C. A small, broad endothermic event was noted in the DT with an onset of about 196° C. with a peak at about 213° C. In some embodiments, Form IV is characterized by a weight loss of about 3.1% between about 25° C. and about 350° C. In some embodiments, Form IV is characterized by an endothermic event, as measured by DT, with an onset of about 196° C. In some embodiments, Form IV is characterized by an endothermic event, as measured by DT, with a peak at about 213° C. In some embodiments, Form IV is characterized by an endothermic event, as measured by DT, with an onset of about 196° C. and a peak at about 213° C. In some embodiments, weight loss is determined by thermogravimetric analysis. In some embodiments, thermogravimetric analysis is conducted substantially as shown in Example 1. In some embodiments, endothermic events are calculated by differential thermal analysis. In some embodiments, differential thermal analysis is conducted substantially as shown in Example 1. In some embodiments, thermogravimetric analysis and differential thermal analysis are conducted simultaneously.

Figure 4C:
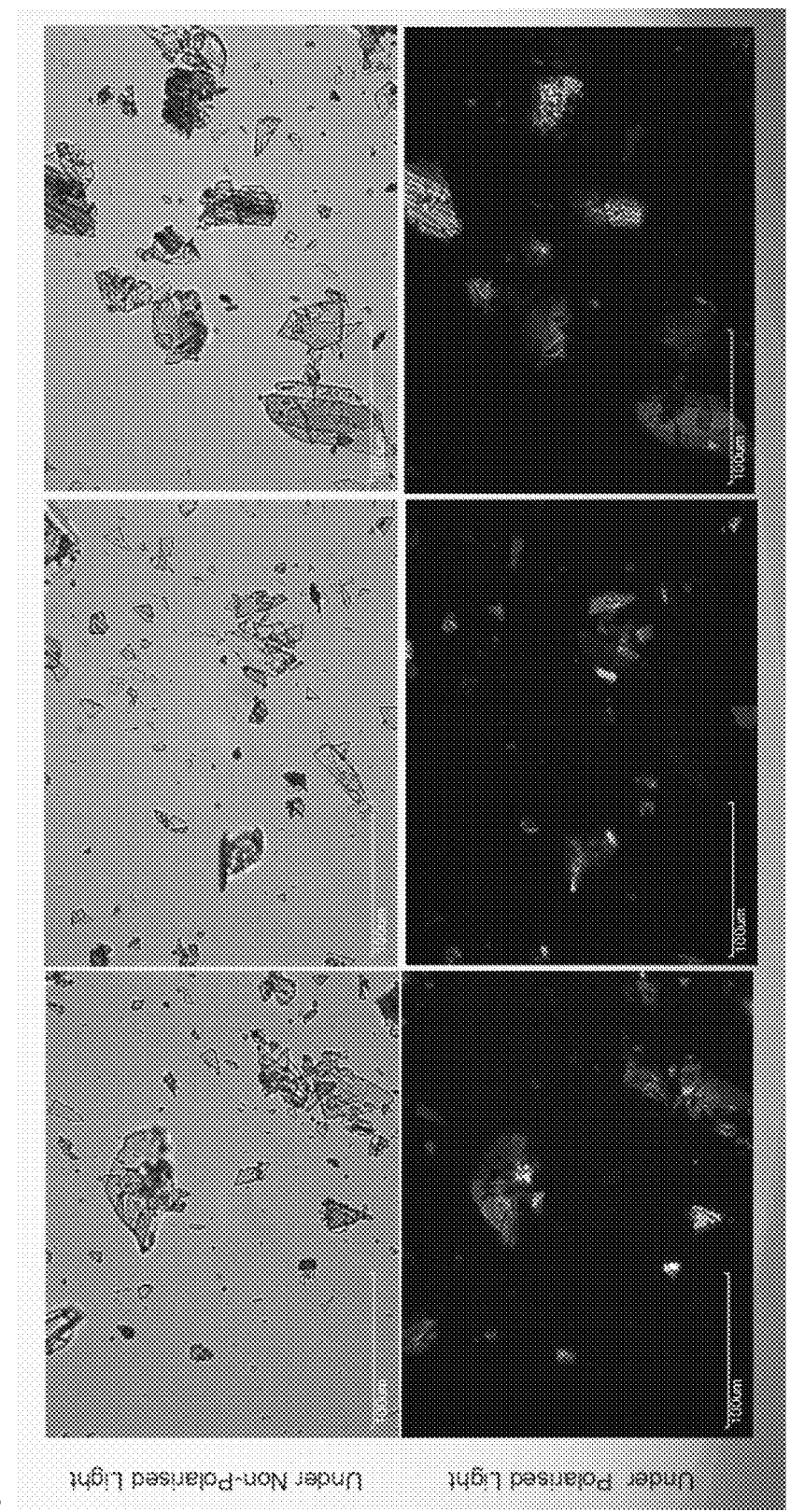
FIG. 4C shows PLM images of the Form IV polymorph of Compound A. Samples in this figure were recovered from dichloromethane:methanol (25:75 v/v).

FIG. 4C shows PLM images of Form IV, recovered from dichloromethane:methanol (25:75 v/v). PLM indicated the material to be birefringent with irregular, lath-like morphology. In some embodiments, Form III is characterized by birefringent material with irregular, lath-like morphology.

A polymorph of the invention may be used in various ways. In some embodiments, a polymorph of Compound A serves as a convenient storage (e.g., bulk storage) form useful for the preparation of an amorphous form of Compound A. In some embodiments, a polymorph of Compound A may be further used in the preparation of pharmaceutical compositions of the disclosure or final dosage form, including, for example, tablets or capsules. In some embodiments, the amorphous form of Compound A may be further used in the preparation of pharmaceutical compositions of the disclosure or final dosage form, including, for example, tablets or capsules.

In some embodiments, the bulk storage form of Compound A is substantially the polymorph of Form I.

In some embodiments, the bulk storage form of Compound A is substantially the polymorph of Form II.

In some embodiments, the bulk storage form of Compound A is substantially the polymorph of Form III.

In some embodiments, the bulk storage form of Compound A is substantially the polymorph of Form IV.

Amorphous Forms

This application further provides an amorphous form of Compound A.

In some embodiments, the bulk storage form of Compound A is substantially the amorphous form of Compound A.

In some embodiments, the amorphous form of Compound A prepared as described herein is used in the preparation of one or more pharmaceutical compositions or dosage forms of the invention, e.g., tablets or capsules, comprising Compound A Therapeutic Compositions This application further provides pharmaceutical compositions comprising a therapeutically effective amount of at least one crystalline and/or amorphous form of Compound A as described herein, in combination with a dispersing agent, carrier, additive or other pharmaceutical excipient, or a combination thereof. The application further provides pharmaceutical compositions comprising a therapeutically effective amount of an amorphous form of Compound A as described herein, in combination with a dispersing agent, carrier, additive or other pharmaceutical excipient, or a combination thereof. In some embodiments, the dispersing agent is hydroxypropyl methylcellulose (HPMC). In some embodiments the additive is D-α-tocopheryl polyethylene glycol succinate (Vitamin E TPGS or TPGS).

Compound A, whether substantially in a crystalline form or amorphous form of the invention as described herein may, in accordance with the disclosure, be administered in a pharmaceutical composition to a patient or subject in single or divided doses. The pharmaceutical composition may be administered orally, parenterally, by inhalation, topically, rectally, nasally, buccally, vaginally, transdermally, sublingually, via suppository administration, or via an implanted reservoir. The term "parenteral" as used herein includes subcutaneous, intravenous, intramuscular, intra-articular, intra-synovial, intra-sternal, intra-thecal, intra-hepatic, intra-lesional and intra-cranial injection or by infusion. Preferably, the pharmaceutical composition is administered orally.

Enteric coated oral tablets may be used to enhance bioavailability of the compounds from an oral route of administration. The most effective dosage form will depend upon the pharmacokinetics of the particular crystalline and/or amorphous form chosen, as well as the severity of the disease and/or condition being treated in the patient. Administration of Compound A according to the present disclosure as a spray, mist, or aerosol for intra-nasal, intra-tracheal, intra-ocular, or pulmonary administration may be used. The present disclosure therefore also is directed to pharmaceutical compositions comprising a therapeutically effective amount of a crystalline form and/or amorphous form of Compound A, or combination thereof as described herein, in combination with a pharmaceutically acceptable carrier, additive or excipient. Compound A may be administered in immediate release, sustained release, or controlled release forms. Sustained or controlled release forms are preferably administered orally, but may alternatively be administered in suppository, transdermal or other topical form. Intramuscular injections, e.g., in liposomal form, may be used to control (e.g., sustain) the release of Compound A at an injection site.

The pharmaceutical compositions described herein may be formulated in a conventional manner using one or more pharmaceutically acceptable carriers, and may be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Sterile injectable forms of the pharmaceutical compositions described herein may be aqueous or oleaginous suspensions. These suspensions may be formulated according to techniques known in the art in view of this disclosure using suitable dispersing or wetting agents and suspending agents. The sterile injectable form may be a sterile injectable solution or suspension in a non-toxic parenterally-acceptable diluent or solvent, for example as a solution in 1, 3-butanediol. Among the acceptable vehicles and solvents that may be employed are water, Ringer's solution and isotonic sodium chloride solution, among others. In addition, sterile, fixed oils are conventionally employed as a solvent or suspending medium. For this purpose, any bland fixed oil may be employed including synthetic mono- or di-glycerides, among others. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may contain a long-chain alcohol diluent or dispersant, such as Ph. Helv or similar alcohol.

The pharmaceutical compositions described herein may be orally administered in any orally acceptable dosage form including, but not limited to, capsules, tablets, aqueous suspensions or solutions. In the case of tablets for oral use, carriers which are commonly used include lactose and corn starch, among others. Lubricating agents, such as magnesium stearate, are also typically added. For oral administration in a capsule form, useful diluents include lactose and dried corn starch, among others. When aqueous suspensions are required for oral use, the active ingredient may be combined with one or more emulsifying and suspending agents. If desired, certain buffering, sweetening, flavoring and/or coloring agents may also be added.

Alternatively, the pharmaceutical compositions described herein may be administered in the form of a suppository or enema for rectal administration, either for local administration to the lower intestinal tract, or for systemic absorption and treatment. Such suppositories can be prepared, in view of this disclosure, by mixing Compound A, either in a substantially crystalline form or substantially amorphous form, with a suitable non-irritating excipient, which is solid or semi-solid at room temperature but liquid at rectal temperature, thereby melting in the rectum to release the drug. Such excipients may include cocoa butter, beeswax, polyethylene glycols, and combinations thereof.

The pharmaceutical compositions described herein may alternatively be administered topically. For example, in one embodiment, the present invention provides a pharmaceutical formulation comprising Compound A in a crystalline form such as Form I, Form II, Form III or Form IV, or in amorphous form, and adapted for topical application such as, e.g., as a salve, ointment, lotion, emulsion or topical liquid.

For topical applications, the pharmaceutical compositions may be formulated in a suitable ointment containing the active component (i.e., Compound A) suspended or dissolved in one or more carriers. Carriers for topical administration include, but are not limited to, mineral oil, liquid petrolatum, white petrolatum, propylene glycol, polyoxyethylene, polyoxypropylene compound, emulsifying wax and water.

Alternatively, the pharmaceutical compositions can be formulated in a suitable lotion or cream containing the active component suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Alternatively, the pharmaceutical formulation of the invention may be delivered via a transdermal patch to be worn for at least 1, 2, 3, 4, 5, 6, 7, 8, 9, 10, 11, 12, 13 or 14 days. In one embodiment, the transdermal patch would be a reservoir patch. In another embodiment, the transdermal patch would be a drug-in-adhesive patch. A transdermal patch according to the invention may also comprise one or more absorption enhancers.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions as described herein may also be administered by nasal aerosol or inhalation. Such compositions are prepared according to techniques known in the art of pharmaceutical formulation in view of this disclosure and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition of the invention may be combined with the carrier or excipient materials to produce single dosage forms, which will vary depending upon the host and disease treated, as well as the particular mode of administration. Preferably, the single dosage form will be formulated to contain between about 0.05 milligram and about 750 milligrams, more preferably about 1 milligram to about 600 milligrams, and even more preferably about 10 milligrams to about 500 milligrams of active ingredient, alone or in combination with at least one other therapeutically active compound. In some embodiments, the other therapeutically active compound is an anti-cancer agent. The polymorph (crystalline form) and/or amorphous form of Compound A, or a pharmaceutical composition thereof, is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg may be a convenient dosage.

It should be understood that a specific dosage and treatment regimen for any particular patient will depend upon a variety of factors, including the severity of the particular disease or condition being treated, the activity and bioavailability of Compound A in the particular dosage form, the age, weight, health and sex of the patient, the rates of metabolism and excretion of the active compound or its metabolites, and the judgment of the treating physician, among other factors.

A patient or subject in need of therapy using a pharmaceutical composition according to the methods described herein can be treated by administering to the patient (subject) a therapeutically effective amount of the composition thereof.

The active compound is included in the pharmaceutical composition in an amount sufficient to deliver to a patient a therapeutically effective amount for the desired indication, without causing undue adverse effects in the patient treated. In some embodiments, a dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day.

The active ingredient is preferably administered to achieve peak plasma concentrations of the active compound of about 0.00001-30 mM, preferably about 0.1-30 µM. This may be achieved, for example, by oral administration of a tablet or capsule, or by the intravenous injection of a solution or formulation of the active ingredient.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered all at once, or may be divided into a number of smaller doses to be administered at selected intervals of time.

Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a buffer; a lubricant such as magnesium stearate; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active polymorph and/or amorphous form of Compound A or a composition thereof can be administered as a component of an elixir, suspension, syrup, wafer, chewing gum or the like. A syrup may contain, in addition to the active compounds, a sweetening agent such as sucrose and certain preservatives, dyes and colorings and flavors.

The active polymorph and/or amorphous form of Compound A or a composition thereof can also be mixed with other active materials that do not impair the desired action, or with materials that supplement the desired action, such as another anti-cancer agents, among others. In certain aspects of the disclosure, one or more compounds, polymorphs, and/or amorphous forms according to the present disclosure, are co-administered with another bioactive agent, such as another anti-cancer agent or a wound healing agent.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, carriers can include physiological saline or phosphate buffered saline (PBS).

In one embodiment, the active compound, polymorph, and/or amorphous forms are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Therapeutic Methods

In an additional aspect, the description provides therapeutic compositions comprising a therapeutically effective amount of a polymorph and/or amorphous form of Compound A, or a pharmaceutical composition thereof as described herein, and a pharmaceutically acceptable carrier. The therapeutic compositions of the invention modulate protein degradation in a patient or subject, for example, an animal such as a human, and can be used for treating or ameliorating disease states or conditions which are causally related to the protein to be degraded.

The terms "treat", "treating", and "treatment", etc., as used herein, refer to any action providing a benefit to a patient for which the active compound, polymorph, and/or amorphous forms may be administered, including the treatment of any disease state or condition, which is causally related (e.g. modulated) to the ER including one or more symptoms thereof. Disease states or conditions, including breast cancer, uterine cancer, ovarian cancer, and/or endometriosis, which may be treated using compounds, polymorphs, amorphous forms and/or pharmaceutical compositions according to the present disclosure are set forth hereinabove.

The description provides therapeutic pharmaceutical compositions as described herein for effectuating the degradation of the ER for the treatment or amelioration of a disease, e.g., cancer. In certain additional embodiments, the disease is breast cancer, uterine cancer, ovarian cancer, endometrial cancer, or endometriosis. As such, in another aspect, the description provides a method of ubiquitinating/degrading the ER in a cell. In certain embodiments, the method comprises administering the bifunctional compound, Compound A, as described herein or a polymorph and/or amorphous form thereof, such that ubiquitination of the ER will occur when placed in proximity to the ubiquitin ligase, leading to ubiquitination and subsequent degradation of the target protein via the proteasomal pathway, providing the control (i.e., reduction) of ER protein levels. The control of ER levels afforded by the invention of the present disclosure provides treatment of a disease state, condition, or symptom causally related to the ER by lowering the level of ER in cells of the patient. In certain embodiments, the method comprises administering a therapeutically effective amount of Compound A as described herein, optionally including one or more pharmaceutically acceptable excipients (e.g., dispersing agent, carrier, lubricant), optionally including another bioactive agent, and combinations thereof.

In additional embodiments, the description provides methods for treating or ameliorating a disease, disorder or symptom thereof in a subject or a patient, e.g., an animal such as a human, comprising administering to a subject in need thereof a composition comprising a therapeutically effective amount, e.g., a therapeutically effective amount, of Compound A as described herein and a pharmaceutically acceptable excipient (e.g., dispersing agent, carrier, lubricant), other bioactive agent, or combination thereof, wherein the composition is effective for treating or ameliorating the disease or disorder or a symptom thereof, in the subject.

In another embodiment, the present disclosure is directed to a method of treating a human patient in need thereof for a disease state, condition or symptom causally related to the ER protein where the degradation of the ER protein produces a therapeutic effect in the patient, the method comprising administering to a patient in need thereof a therapeutically effective amount of Compound A according to the present disclosure, optionally in combination with another bioactive agent. The disease state, condition or symptom may be caused by expression or overexpression of the ER protein.

The term "disease state, condition or symptom" is used to describe any disease state, condition or symptom causally related to protein activity, overactivity, expression or overexpression (e.g., the amount of ER expressed in a patient is elevated) where targeted degradation of the protein in a patient provides a beneficial therapy or relief of the disease state, condition or symptom to the patient. In certain instances, the disease state or condition may be reduced, mitigated or ameliorated. In other instances, the disease state, condition or symptom may be reversed or cured.

The terms "neoplasia" and "cancer", as used in the specification, refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe any and all cancerous disease states and embraces or encompasses the pathological process associated with malignant hematogenous, ascitic and solid tumors. Exemplary cancers which may be treated by the present compound polymorphs, and/or amorphous forms either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, endometrial, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using compounds according to the present disclosure include, for example, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML. In some embodiments, the cancers which may be treated by the present compound, polymorphs, and/or amorphous forms either alone or in combination with at least one additional anti-cancer agent include breast cancer, ovarian cancer, endometrial cancer or uterine cancer.

Protein Level Control

The present disclosure also provides methods for the control (e.g. reduction) of protein levels within a cell. This is based on the use of Compound A, or a polymorph or amorphous form thereof, as described herein, which results in the targeted ubiquitination of the ER protein and its proteasomal degradation resulting in the control (i.e. reduction) of the amount of the ER protein in cells of a biological system or subject or patient, e.g. to gain a particular therapeutic benefit.

EMBODIMENTS

The Aspects of the present disclosure are further described with reference to the following numbered embodiments:

Embodiment 1. A polymorph of (S)-3-(5-(4-((1-(4-((1R,2S)-6-hydroxy-2-phenyl-1,2,3,4-tetrahydronaphthalen-1-yl)

phenyl)piperidin-4-yl)methyl)piperazin-1-yl)-1-oxoisoindo-lin-2-yl)piperidine-2,6-dione (Compound A)

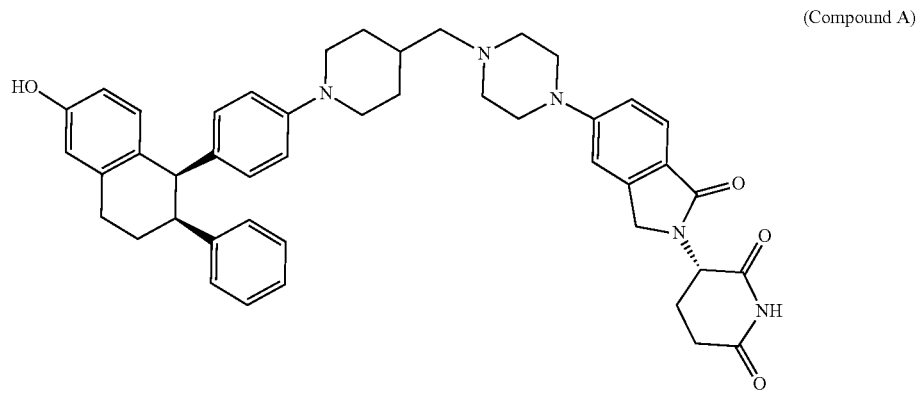 [SMILES: O=C1CC[C@H](N2Cc3cc(N4CCN(CC5CCN(c6ccc([C@@H]7c8ccc(O)cc8CC[C@@H]7c7ccccc7)cc6)CC5)CC4)ccc3C2=O)C(=O)N1]

(Compound A)

characterized by an X-ray powder diffraction pattern including peaks at about 13.9°2θ and about 17.9°2θ using Cu Kα radiation.

Embodiment 2. A polymorph of (S)-3-(5-(4-((1-(4-(((1R, 2S)-6-hydroxy-2-phenyl-1,2,3,4-tetrahydronaphthalen-1-yl)phenyl)piperidin-4-yl)methyl)piperazin-1-yl)-1-oxoisoindo-lin-2-yl)piperidine-2,6-dione (Compound A)

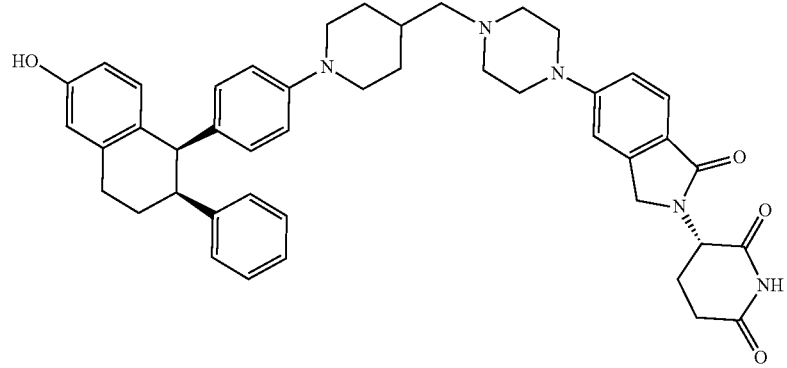

(Compound A)

characterized by an X-ray powder diffraction pattern including peaks at about 13.9°2θ, about 16.4°2θ, and about 17.9°2θ using Cu Kα radiation.

Embodiment 3. A polymorph of (S)-3-(5-(4-((1-(4-(((1R,2S)-6-hydroxy-2-phenyl-1,2,3,4-tetrahydronaphthalen-1-yl)phenyl)piperidin-4-yl)methyl)piperazin-1-yl)-1-oxoisoindolin-2-yl)piperidine-2,6-dione (Compound A)

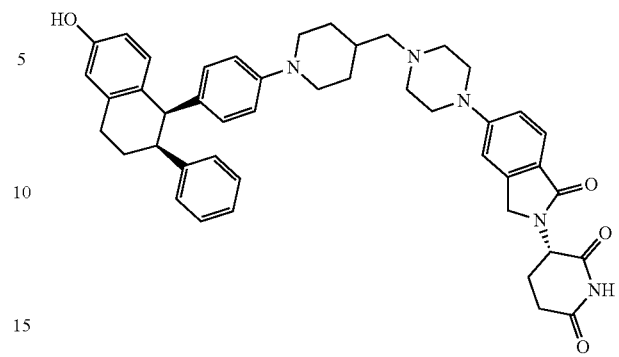
(Compound A)

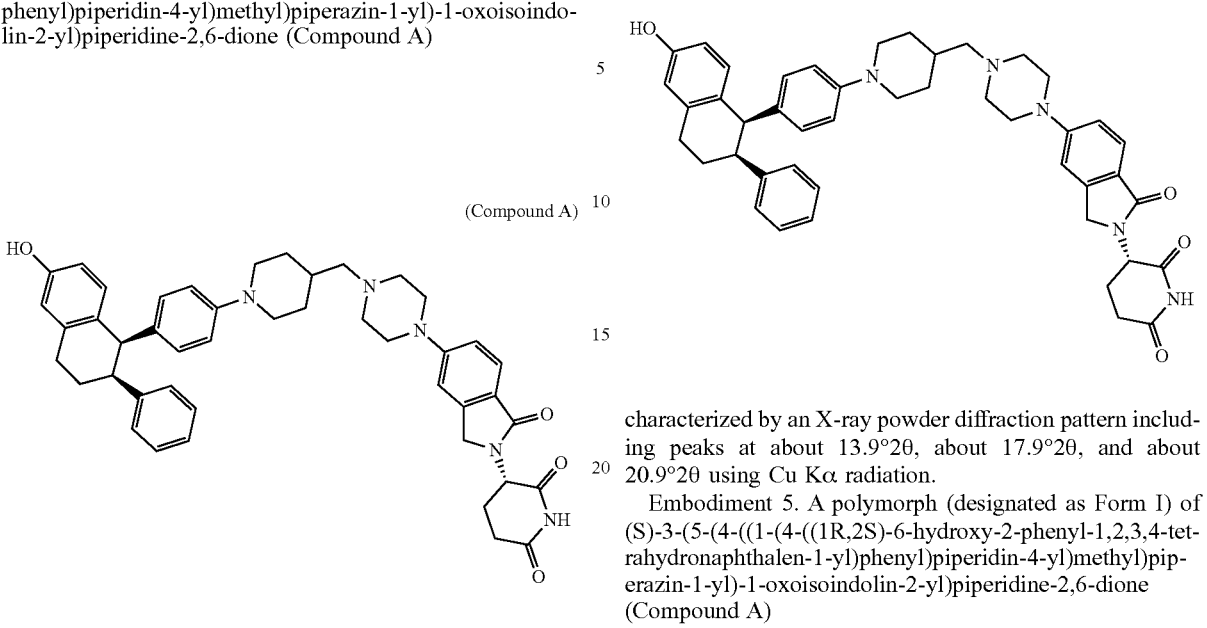
(Compound A)

characterized by an X-ray powder diffraction pattern including peaks at about 13.9°2θ, about 17.9°2θ, and about 20.9°2θ using Cu Kα radiation.

Embodiment 5. A polymorph (designated as Form I) of (S)-3-(5-(4-((1-(4-(((1R,2S)-6-hydroxy-2-phenyl-1,2,3,4-tetrahydronaphthalen-1-yl)phenyl)piperidin-4-yl)methyl)piperazin-1-yl)-1-oxoisoindolin-2-yl)piperidine-2,6-dione (Compound A)

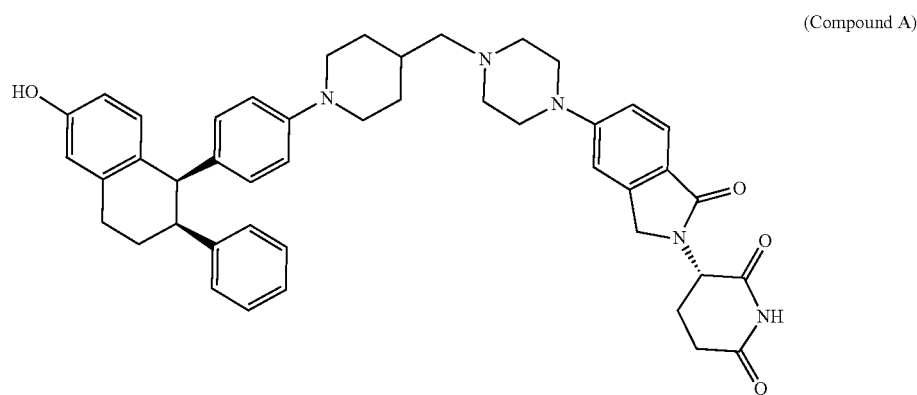 [SMILES: O=C1CC[C@H](N2Cc3cc(N4CCN(CC5CCN(c6ccc([C@@H]7c8ccc(O)cc8CC[C@@H]7c7ccccc7)cc6)CC5)CC4)ccc3C2=O)C(=O)N1]
(Compound A)

characterized by an X-ray powder diffraction pattern including peaks at about 13.9°2θ, about 16.2°2θ, and about 17.9°2θ using Cu Kα radiation.

Embodiment 4. A polymorph of (S)-3-(5-(4-((1-(4-(((1R,2S)-6-hydroxy-2-phenyl-1,2,3,4-tetrahydronaphthalen-1-yl)phenyl)piperidin-4-yl)methyl)piperazin-1-yl)-1-oxoisoindolin-2-yl)piperidine-2,6-dione (Compound A)

characterized by an X-ray powder diffraction pattern including peaks at about 13.9°2θ and about 17.9°2θ using Cu Kα radiation.

Embodiment 6. The polymorph of embodiment 1, further characterized by an X-ray powder diffraction pattern including a peak at about 16.4°2θ, using Cu Kα radiation.

Embodiment 7. The polymorph of embodiment 1, further characterized by an X-ray powder diffraction pattern including at least one peak selected from about 16.2°2θ, about 16.4°2θ, about 18.5°2θ, and about 20.9°2θ, using Cu Kα radiation.

Embodiment 8. The polymorph of embodiment 1, further characterized by an X-ray powder diffraction pattern including peaks at about 16.2°2θ, about 16.4°2θ, about 18.5°2θ, and about 20.9°2θ, using Cu Kα radiation.

Embodiment 9. The polymorph of any one of embodiments 1-8, further characterized by an X-ray powder diffraction pattern including at least one peak selected from about 13.5°2θ, about 14.3°2θ, about 14.5°2θ, about 16.8°2θ, using Cu Kα radiation.

Embodiment 10. The polymorph of any one of embodiments 1-9, further characterized by an X-ray powder diffraction pattern including peaks at about 13.5°2θ, about 14.3°2θ, about 14.5°2θ, about 16.8°2θ, using Cu Kα radiation.

Embodiment 11. The polymorph of any one of embodiments 1-10, characterized by an X-ray powder diffraction pattern substantially similar to that set forth in FIG. 1A.

Embodiment 12. The polymorph of any one of embodiments 1-11, further characterized by an endothermic event, as measured by DT, having an onset of about 259° C. and a peak at about 266° C.

Embodiment 13. The polymorph of any one of embodiments 1-12, further characterized by a weight loss, as measured by TG, of about 1% between about 25° C. and about 250° C.

Embodiment 14. A polymorph of (S)-3-(5-(4-((1-(4-((1R,2S)-6-hydroxy-2-phenyl-1,2,3,4-tetrahydronaphthalen-1-yl)phenyl)piperidin-4-yl)methyl)piperazin-1-yl)-1-oxoisoindolin-2-yl)piperidine-2,6-dione (Compound A)

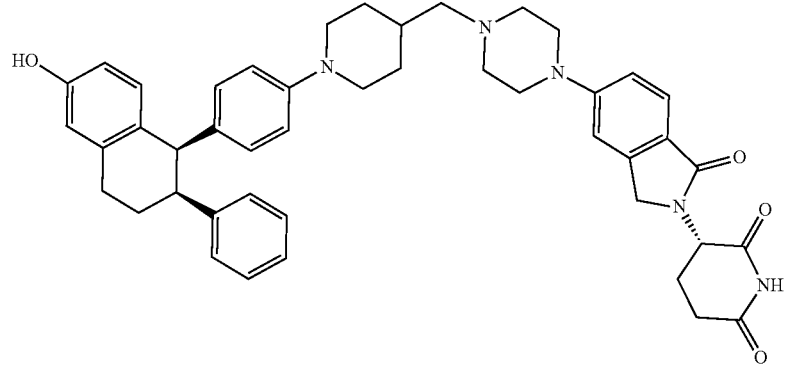

(Compound A)

characterized by an X-ray powder diffraction pattern including peaks at about 10.0°2θ and about 17.5°2θ using Cu Kα radiation.

Embodiment 15. A polymorph of (S)-3-(5-(4-((1-(4-((1R,2S)-6-hydroxy-2-phenyl-1,2,3,4-tetrahydronaphthalen-1-yl)phenyl)piperidin-4-yl)methyl)piperazin-1-yl)-1-oxoisoindolin-2-yl)piperidine-2,6-dione (Compound A)

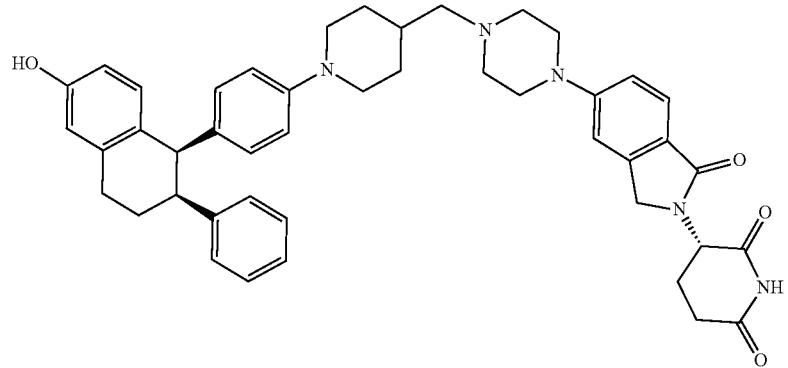

(Compound A)

characterized by an X-ray powder diffraction pattern including peaks at about 10.0°2θ, about 16.3°2θ, and about 17.5°2θ using Cu Kα radiation.

Embodiment 16. A polymorph of (S)-3-(5-(4-((1-(4-(((1R,2S)-6-hydroxy-2-phenyl-1,2,3,4-tetrahydronaphthalen-1-yl)phenyl)piperidin-4-yl)methyl)piperazin-1-yl)-1-oxoisoindolin-2-yl)piperidine-2,6-dione (Compound A)

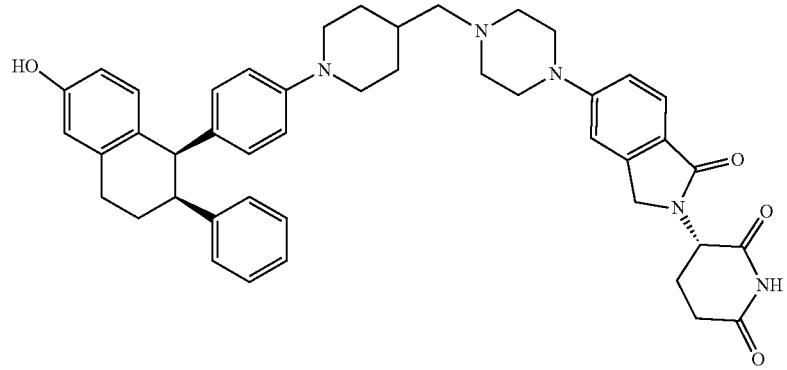
(Compound A)

characterized by an X-ray powder diffraction pattern including peaks at about 9.2°2θ, about 16.3°2θ, and about 17.5°2θ using Cu Kα radiation.

Embodiment 17. A polymorph of (S)-3-(5-(4-((1-(4-(((1R,2S)-6-hydroxy-2-phenyl-1,2,3,4-tetrahydronaphthalen-1-yl)phenyl)piperidin-4-yl)methyl)piperazin-1-yl)-1-oxoisoindolin-2-yl)piperidine-2,6-dione (Compound A)

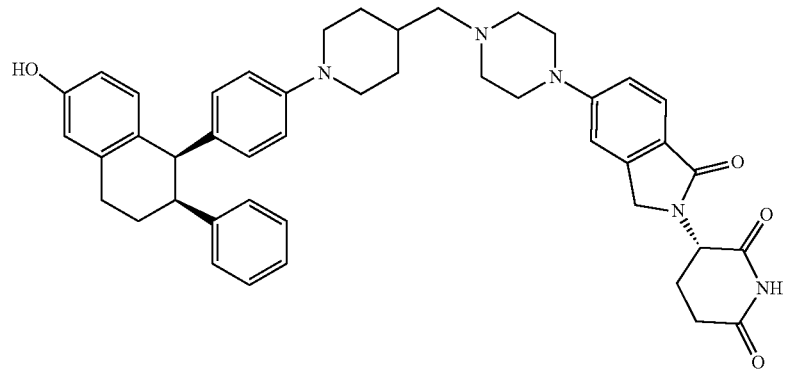
(Compound A)

characterized by an X-ray powder diffraction pattern including peaks at about 16.3°2θ, about 17.5°2θ, and about 18.1°2θ using Cu Kα radiation.

Embodiment 18. A polymorph (designated as Form II) of (S)-3-(5-(4-((1-(4-((1R,2S)-6-hydroxy-2-phenyl-1,2,3,4-tetrahydronaphthalen-1-yl)phenyl)piperidin-4-yl)methyl)piperazin-1-yl)-1-oxoisoindolin-2-yl)piperidine-2,6-dione (Compound A)

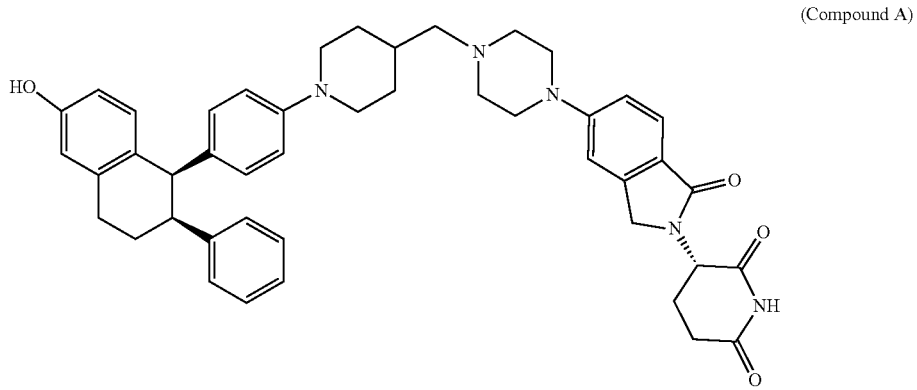 [SMILES: O=C1CC[C@H](N2Cc3cc(N4CCN(CC5CCN(c6ccc([C@@H]7c8ccc(O)cc8CC[C@@H]7c7ccccc7)cc6)CC5)CC4)ccc3C2=O)C(=O)N1]
(Compound A)

characterized by an X-ray powder diffraction pattern including peaks at about 10.0°2θ and about 17.5°2θ using Cu Kα radiation.

Embodiment 19. The polymorph of embodiment 14 or 18, further characterized by an X-ray powder diffraction pattern including a peak at about 16.3°2θ, using Cu Kα radiation.

Embodiment 20. The polymorph of any one of embodiments 14-19, further characterized by an X-ray powder diffraction pattern including at least one peak selected from at about 9.2°2θ, about 16.3°2θ, and about 18.1°2θ, using Cu Kα radiation.

Embodiment 21. The polymorph of any one of embodiments 14-20, further characterized by an X-ray powder diffraction pattern including peaks at about 9.2°2θ, about 16.3°2θ, and about 18.1°2θ, using Cu Kα radiation.

Embodiment 22. The polymorph of any one of embodiments 14-21, characterized by an X-ray powder diffraction pattern substantially similar to that set forth in FIG. 2A.

Embodiment 23. The polymorph of any one of embodiments 14-22, further characterized by an endothermic event, as measured by DT, with a peak at about 212° C.

Embodiment 24. The polymorph of any one of embodiments 14-23, further characterized by a weight loss, as measured by TG, of about 11% between about 25° C. and about 85° C.

Embodiment 25. A polymorph of (S)-3-(5-(4-((1-(4-((1R,2S)-6-hydroxy-2-phenyl-1,2,3,4-tetrahydronaphthalen-1-yl)phenyl)piperidin-4-yl)methyl)piperazin-1-yl)-1-oxoisoindolin-2-yl)piperidine-2,6-dione (Compound A)

(Compound A)

characterized by an X-ray powder diffraction pattern including peaks at about 10.7°2θ and 18.2°2θ using Cu Kα radiation.

Embodiment 26. A polymorph of (S)-3-(5-(4-((1-(4-((1R,2S)-6-hydroxy-2-phenyl-1,2,3,4-tetrahydronaphthalen-1-yl)phenyl)piperidin-4-yl)methyl)piperazin-1-yl)-1-oxoisoindolin-2-yl)piperidine-2,6-dione (Compound A)

(Compound A)

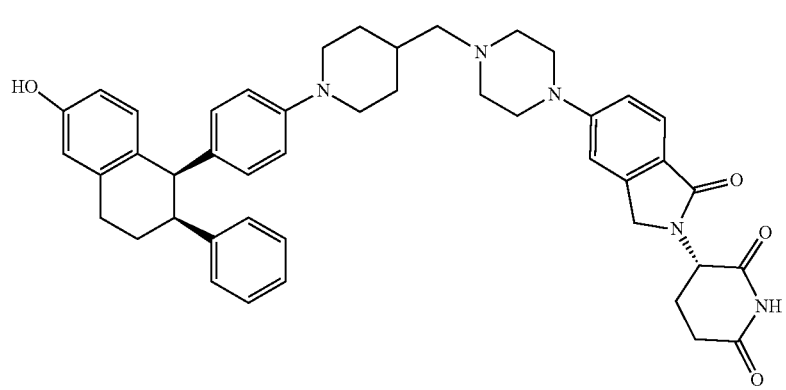

characterized by an X-ray powder diffraction pattern including peaks at about 8.8°2θ, about 10.7°2θ, and about 18.2°2θ using Cu Kα radiation.

Embodiment 27. A polymorph of (S)-3-(5-(4-((1-(4-(((1R,2S)-6-hydroxy-2-phenyl-1,2,3,4-tetrahydronaphthalen-1-yl)phenyl)piperidin-4-yl)methyl)piperazin-1-yl)-1-oxoisoindolin-2-yl)piperidine-2,6-dione (Compound A)

(Compound A)

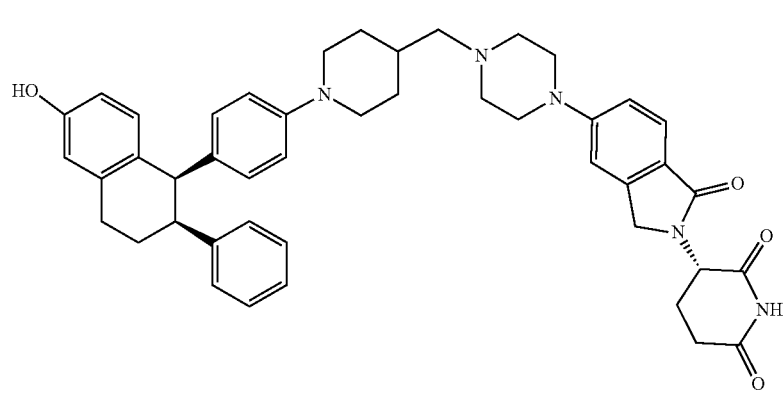

characterized by an X-ray powder diffraction pattern including peaks at about 10.7°2θ, about 11.2°2θ, and 18.2°2θ using Cu Kα radiation.

Embodiment 28. A polymorph of (S)-3-(5-(4-((1-(4-(((1R,2S)-6-hydroxy-2-phenyl-1,2,3,4-tetrahydronaphthalen-1-yl)phenyl)piperidin-4-yl)methyl)piperazin-1-yl)-1-oxoisoindolin-2-yl)piperidine-2,6-dione (Compound A)

(Compound A)

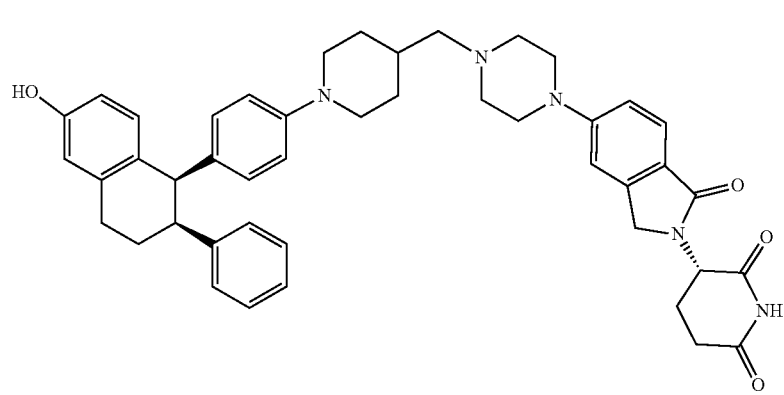

characterized by an X-ray powder diffraction pattern including peaks at about 10.7°2θ, about 16.5°2θ, and about 18.2°2θ using Cu Kα radiation.

Embodiment 29. A polymorph (designated as Form III) of (S)-3-(5-(4-((1-(4-(((1R,2S)-6-hydroxy-2-phenyl-1,2,3,4-tetrahydronaphthalen-1-yl)phenyl)piperidin-4-yl)methyl)piperazin-1-yl)-1-oxoisoindolin-2-yl)piperidine-2,6-dione (Compound A)

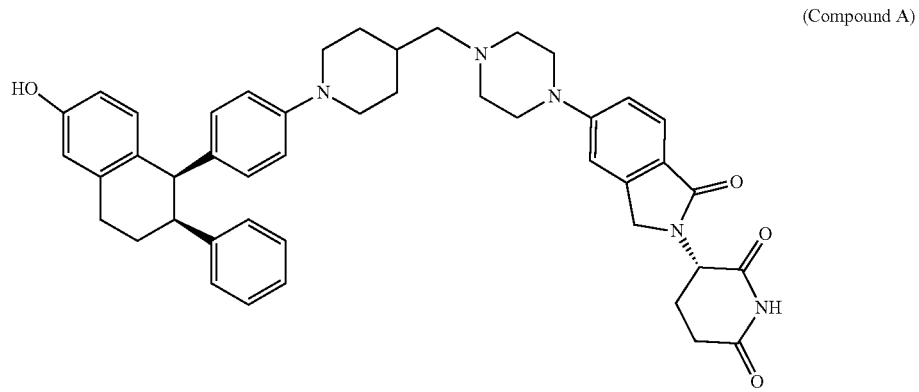 [SMILES: O=C1CC[C@H](N2Cc3cc(N4CCN(CC5CCN(c6ccc([C@@H]7c8ccc(O)cc8CC[C@@H]7c7ccccc7)cc6)CC5)CC4)ccc3C2=O)C(=O)N1]

(Compound A)

characterized by an X-ray powder diffraction pattern including peaks at about 10.7°2θ and 18.2°2θ using Cu Kα radiation.

Embodiment 30. The polymorph of any one of embodiments 25 or 27-29, further characterized by an X-ray powder diffraction pattern including a peak at about 8.8°2θ, using Cu Kα radiation.

Embodiment 31. The polymorph of any one of embodiments 25-30, further characterized by an X-ray powder diffraction pattern including at least one peak selected from about 8.8°2θ, about 11.2°2θ, about 15.0°2θ, about 16.5°2θ, and about 17.8°2θ, using Cu Kα radiation.

Embodiment 32. The polymorph of any one of embodiments 25-31, further characterized by an X-ray powder diffraction pattern including peaks at about 8.8°2θ, about 11.2°2θ, about 15.0°2θ, about 16.5°2θ, and about 17.8°2θ, using Cu Kα radiation.

Embodiment 33. The polymorph of any one of embodiments 25-32, further characterized by an X-ray powder diffraction pattern substantially similar to that set forth in FIG. 3A.

Embodiment 34. The polymorph of any one of embodiments 25-33, further characterized by an endothermic event, as measured by DT, with an onset of about 196° C. and a peak at about 204° C.

Embodiment 35. The polymorph of any one of embodiments 25-34, further characterized by a weight loss, as measured by TG, of about 3.7% between about 25° C. and about 75° C.

Embodiment 36. The polymorph of embodiment 35, further characterized by a weight loss, as measured by TG, of about 4.7% between about 75° C. and about 160° C.

Embodiment 37. The polymorph of embodiment 36, further characterized by a weight loss, as measured by TG, of about 0.6% between about 160° C. and about 350° C.

Embodiment 38. A polymorph of (S)-3-(5-(4-((1-(4-(((1R,2S)-6-hydroxy-2-phenyl-1,2,3,4-tetrahydronaphthalen-1-yl)phenyl)piperidin-4-yl)methyl)piperazin-1-yl)-1-oxoisoindolin-2-yl)piperidine-2,6-dione (Compound A)

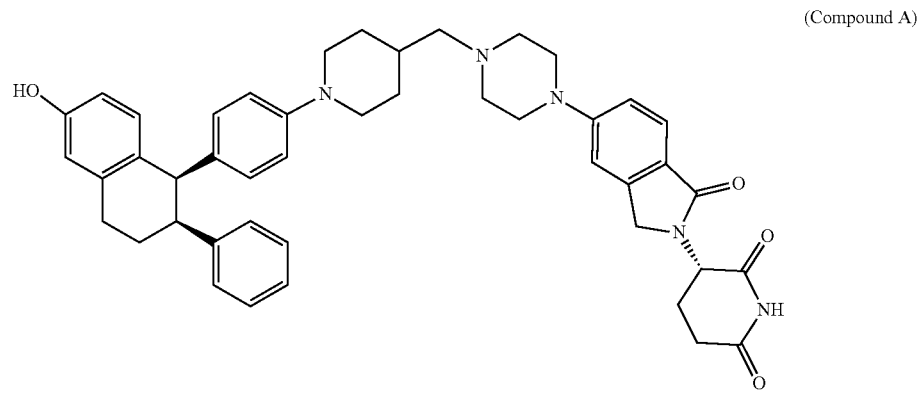 [SMILES: O=C1CC[C@H](N2Cc3cc(N4CCN(CC5CCN(c6ccc([C@@H]7c8ccc(O)cc8CC[C@@H]7c7ccccc7)cc6)CC5)CC4)ccc3C2=O)C(=O)N1]

(Compound A)

characterized by an X-ray powder diffraction pattern including peaks at about 10.5°2θ, about 14.5°2θ, and about 16.9°2θ.

Embodiment 39. A polymorph (designated as Form IV) of (S)-3-(5-(4-((1-(4-(((1R,2S)-6-hydroxy-2-phenyl-1,2,3,4-tetrahydronaphthalen-1-yl)phenyl)piperidin-4-yl)methyl)piperazin-1-yl)-1-oxoisoindolin-2-yl)piperidine-2,6-dione (Compound A)

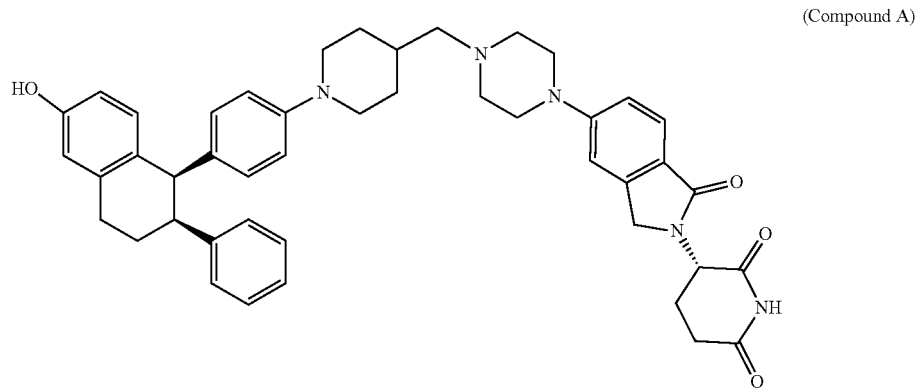 [SMILES: O=C1CC[C@H](N2Cc3cc(N4CCN(CC5CCN(c6ccc([C@@H]7c8ccc(O)cc8CC[C@@H]7c7ccccc7)cc6)CC5)CC4)ccc3C2=O)C(=O)N1]

(Compound A)

characterized by an X-ray powder diffraction pattern including peaks at about 10.5°2θ, about 14.5°2θ, and about 16.9°2θ.

Embodiment 40. The polymorph of embodiment 38 or 39, further characterized by an X-ray powder diffraction pattern including at least one peak selected from about 11.5°2θ, about 14.2°2θ, about 16.3°2θ, and about 17.8°2θ, using Cu Kα radiation.

Embodiment 41. The polymorph of any one of embodiments 38-40, further characterized by an X-ray powder diffraction pattern including peaks at about 11.5°2θ, about 14.2°2θ, about 16.3°2θ, and about 17.8°2θ, using Cu Kα radiation.

Embodiment 42. The polymorph of any one of embodiments 38-41, characterized by an X-ray powder diffraction pattern substantially similar to that set forth in FIG. 4A.

Embodiment 43. The polymorph of any one of embodiments 38-42, further characterized by an endothermic event, as measured by DT, with an onset of about 196° C. and a peak at about 213° C.

Embodiment 44. The polymorph of any one of embodiments 38-43, further characterized by a weight loss, as measured by TG, of about 3.1% between about 25° C. and about 350° C.

Embodiment 45. A method of treating a disease or disorder in a subject in need thereof, comprising administering to the subject a therapeutically effective amount of the polymorph of any one of embodiments 1-44.

Embodiment 46. The method of embodiment 45, wherein the disease or disorder is associated with estrogen receptor (ER) activity, overactivity, constitutive activity, expression, overexpression, or accumulation and aggregation.

Embodiment 47. The method of embodiment 45 or 46, wherein the disease or disorder is cancer or a neoplasia associated with ER activity, overactivity, constitutive activity, expression, overexpression, or accumulation and aggregation.

Embodiment 48. The method of any one of embodiments 45-47, wherein the disease or disorder is breast cancer or uterine cancer or endometriosis.

Embodiment 49. A pharmaceutical composition comprising a therapeutically effective amount of the polymorph of any one of embodiments 1-44 and a pharmaceutically acceptable carrier wherein the composition is effective in treating or ameliorating at least one symptom of the disease or disorder.

Embodiment 50. The composition according to embodiment 49, wherein the disease or disorder is associated with overactivity, constitutive activity, or ER accumulation and aggregation.

Embodiment 51. The composition according to embodiment 49 or 50, wherein the disease or disorder is cancer or a neoplasia associated with ER accumulation and aggregation, or ER activity or over-activity.

Embodiment 52. The composition according to any one of embodiments 49-51, wherein the disease or disorder is breast cancer or uterine cancer or endometriosis.

Embodiment 53. A pharmaceutical composition comprising a therapeutically effective amount of an amorphous form of Compound A

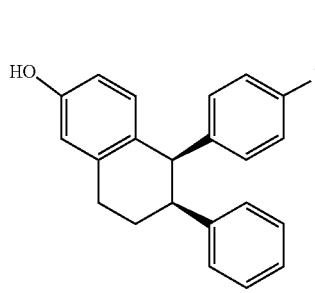
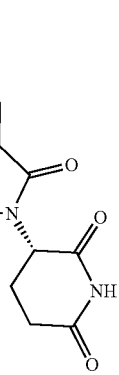

(Compound A)

and a pharmaceutically acceptable dispersing agent.

Embodiment 54. The composition of embodiment 53 further comprising a pharmaceutically acceptable additive.

Embodiment 55. The composition of embodiment 53 or 54 wherein the pharmaceutically acceptable additive is HPMC.

Embodiment 56. The composition of embodiments 53 or 54 wherein the pharmaceutically acceptable additive is TPGS.

Embodiment 57. The composition of any one of embodiments 53-56 wherein the composition is effective in treating or ameliorating at least one symptom of the disease or disorder.

Embodiment 58. The composition according to embodiment 57, wherein the disease or disorder is associated with overactivity, constitutive activity, or ER accumulation and aggregation.

Embodiment 59. The composition according to embodiment 57 or 58, wherein the disease or disorder is cancer or a neoplasia associated with ER accumulation and aggregation, or ER activity or over-activity.

Embodiment 60. The composition according to any one of embodiments 57-59, wherein the disease or disorder is breast cancer or uterine cancer or endometriosis.

Embodiment 61. Use of the polymorph of any one of embodiments 1-44 in the manufacture of a medicament for the treatment of a disease or disorder.

Embodiment 62. The use according to embodiment 61, wherein the disease or disorder is associated with ER accumulation and aggregation, or ER activity or over-activity.

Embodiment 63. The use according to embodiment 61 or 62, wherein the disease or disorder is cancer or a neoplasia associated with ER accumulation and aggregation, or ER activity or over-activity.

Embodiment 64. The use according to any one of embodiments 61-63, wherein the disease or disorder is breast cancer or uterine cancer, or endometriosis.

Embodiment 65. The polymorph of any one of embodiments 1-44 for use in medicine.

Embodiment 66. The polymorph of any one of embodiments 1-44 for use in the treatment of a disease or disorder, wherein the disease or disorder is associated with ER accumulation and aggregation, or ER activity or over-activity.

Embodiment 67. The polymorph for use according to embodiment 66, wherein the disease or disorder is cancer or a neoplasia associated with ER accumulation and aggregation, or ER activity or over-activity.

Embodiment 68. The polymorph for use according to embodiment 66 or 67, wherein the disease or disorder is breast cancer or uterine cancer, or endometriosis.

Embodiment 69. A method of making the polymorph of Compound A of any one of embodiments 1-13, comprising recrystallizing Compound A from a solvent.

Embodiment 70. The method of embodiment 69, wherein the solvent is selected from the group consisting of acetone, 1-butanol, 2-ethoxyethanol, ethanol, ethyl acetate, isopropyl acetate, methanol, methyl ethyl ketone, 1-propanol, 2-propanol, polyethylene glycol, and a mixture of ethanol/water.

Embodiment 71. The method of embodiment 69, wherein the solvent is 1-butanol.

Embodiment 72. The method of embodiment 69, wherein the solvent is methyl ethyl ketone Embodiment 73. A method of making the polymorph of Compound A of any one of embodiments 14-24, comprising recrystallizing Compound A from a solvent.

Embodiment 74. The method of embodiment 73, wherein the solvent is selected from dichloromethane and a mixture of acetone/water.

Embodiment 75. A method of making the polymorph of Compound A of any one of embodiments 25-37, comprising recrystallizing Compound A from a solvent.

Embodiment 76. The method of embodiment 75, wherein the solvent is acetonitrile.

Embodiment 77. A method of making the polymorph of Compound A of any one of embodiments 38-44, comprising crash-cooling a solution of Compound A in a solvent.

Embodiment 78. A method of making the polymorph of Compound A of any one of embodiments 38-44, comprising addition of an anti-solvent to a solution of Compound A in a solvent.

Embodiment 79. The method of embodiment 77 or 78, wherein the solvent is a mixture of dichloromethane and methanol.

Embodiment 80. The method of embodiment 79, wherein the ratio of dichloromethane and methanol is about 25:75 (v/v).

Embodiment 81. The method of any one of embodiments 78-80, wherein the anti-solvent is tert-butyl methyl ether.

EXAMPLES

Compound A can be prepared according to the methods disclosed in U.S. Pat. No. 10,647,698, which is incorporated herein for all purposes. The following examples are used to assist in describing the present disclosure, but should not be seen as limiting the present disclosure in any way.

Example 1: Methods of Analysis

Unless otherwise specified, all characterization data were obtained using the following procedures:

X-Ray Powder Diffraction (XRPD)

XRPD analysis was carried out on a PANalytical X'pert pro, scanning the samples between 3 and 35°2θ. The material was gently ground to release any agglomerates and loaded onto a multi-well plate with Mylar polymer film to support the sample. The multi-well plate was then placed into the diffractometer and analyzed using Cu K radiation (α1λ, =1.54060 Å; α2=1.54443 Å; β=1.39225 Å; α1:α2 ratio=0.5) running in transmission mode (step size 0.0130°2θ) using 40 kV/40 mA generator settings.

Polarized Light Microscopy (PLM)

The presence of crystallinity (birefringence) was determined using an Olympus BX50 polarizing microscope, equipped with a Motic camera and image capture software (Motic Images Plus 2.0). All images were recorded using the 20× objective, unless otherwise stated.

Thermogravimetric Analysis (TGA) and Differential Thermal Analysis (DTA)

Approximately 5 mg of material was weighed into an open aluminum pan and loaded into a simultaneous thermogravimetric/differential thermal analyzer (TG/DTA) and held at room temperature. The sample was then heated at a rate of 10° C./min from 20° C. to 400° C. during which time the change in sample weight was recorded along with any differential thermal events (DTA). Nitrogen was used as the purge gas, at a flow rate of 300 cm$^3$/min.

Differential Scanning Calorimetry (DSC)

Approximately 5 mg of material was weighed into an aluminum DSC pan and sealed non-hermetically with a pierced aluminum lid. The sample pan was then loaded into a Seiko DSC6200 (equipped with a cooler) cooled and held at 20° C. Once a stable heat-flow response was obtained, the sample and reference were heated to the desired temperature at a scan rate of 10° C./min and the resulting heat flow response monitored. Nitrogen was used as the purge gas, at a flow rate of 50 cm$^3$/min.

Example 2: Polymorph Screen

To vials containing about 30 mg of Compound A, the appropriate solvent was added to suspend the material. The experiments were then temperature cycled between ambient temperature (about 22° C.) and 40° C. in 4 hour cycles for 72 hours.

All solids were isolated by centrifugation and analyzed by XRPD. Any new forms were further analyzed by TG/DT and PLM. The results of this step are shown below in Table 5.

TABLE 5

Temperature Cycling Results

| Solvent | XRPD Pattern* |
|---|---|
| Acetone | I |
| Acetonitrile | III |
| 1-Butanol | I |
| Cyclohexane | A |
| Dichloromethane | II |
| N,N'-Dimethylacetamide | — |
| N,N'-Dimethylformamide | — |

TABLE 5-continued

Temperature Cycling Results

| Solvent | XRPD Pattern* |
|---|---|
| 1,4-Dioxane | — |
| 2-Ethoxyethanol | I |
| Ethanol | I |
| Ethyl acetate | I |
| Isopropyl acetate | I |
| Methanol | I |
| Methyl ethyl ketone | I |
| 2-Methyltetrahydrofuran | A |
| 1-Propanol | I |
| 2-Propanol | I |
| Tetrahydrofuran | — |
| Toluene | A |
| Water | A |
| Acetone:Water (90:10 v/v) | II |
| Ethanol:Water (90:10 v/v) | I |
| Dichloromethane:Methanol (90:10 v/v) | — |
| Dichloromethane:Methanol (25:75 v/v) | — |
| Polyethylene glycol | — |

*"A": Amorphous Form;
"—": Insufficient Solid

The filtered Compound A saturated solutions were then divided into three aliquots and used for subsequent polymorph screening experiments as detailed below:

Evaporation: Saturated solutions of Compound A were transferred to 2 mL vials; these vials were then uncapped and allowed to evaporate at ambient temperature to recover material. All solids recovered were analyzed by XRPD. The results are shown below in Table 6.

TABLE 6

Evaporation Results

| Solvent | XRPD Pattern* |
|---|---|
| Acetone | — |
| Acetonitrile | — |
| 1-Butanol | — |
| Cyclohexane | — |
| Dichloromethane | A |
| N,N'-Dimethylacetamide | — |
| N,N'-Dimethylformamide | A |
| 1,4-Dioxane | — |
| 2-Ethoxyethanol | — |
| Ethanol | A |
| Ethyl acetate | A |
| Isopropyl acetate | A |
| Methanol | — |
| Methyl ethyl ketone | — |
| 2-Methyltetrahydrofuran | — |
| 1-Propanol | — |
| 2-Propanol | — |
| Tetrahydrofuran | A |
| Toluene | — |
| Water | — |
| Acetone:Water (90:10 v/v) | — |
| Ethanol:Water (90:10 v/v) | — |
| Dichloromethane Methanol (90:10 v/v) | A |
| Dichloromethane Methanol (25:75 v/v) | A |
| Polyethylene glycol | — |

*"A": Amorphous Form;
"—": Insufficient Solid

Crash Cool: Saturated solutions of Compound A were stored at 2-8° C. for 24-72 h. At this time, any material recovered was analyzed by XRPD and the experiments were then stored at −20° C. for 24-72 h. After this time, any material recovered was analyzed by XRPD. The results are shown below in Tables 7 and 8.

TABLE 7

Crash Cooling Results (2-8° C.) Results

| Solvent | XRPD Pattern* |
|---|---|
| Acetone | — |
| Acetonitrile | — |
| 1-Butanol | — |
| Cyclohexane | — |
| Dichloromethane | — |
| N,N'-Dimethylacetamide | — |
| N,N'-Dimethylformamide | — |
| 1,4-Dioxane | — |
| 2-Ethoxyethanol | — |
| Ethanol | — |
| Ethyl acetate | — |
| Isopropyl acetate | — |
| Methanol | — |
| Methyl ethyl ketone | — |
| 2-Methyltetrahydrofuran | — |
| 1-Propanol | — |
| 2-Propanol | — |
| Tetrahydrofuran | — |
| Toluene | — |
| Water | — |
| Acetone:Water (90:10 v/v) | — |
| Ethanol:Water (90:10 v/v) | — |
| Dichloromethane:Methanol (90:10 v/v) | — |
| Dichloromethane:Methanol (25:75 v/v) | IV |
| Polyethylene glycol | — |

*"A": Amorphous Form;
"—": Insufficient Solid

TABLE 8

Crash Cooling Results (−20° C.) Results

| Solvent | XRPD Pattern* |
|---|---|
| Acetone | — |
| Acetonitrile | — |
| 1-Butanol | — |
| Cyclohexane | — |
| Dichloromethane | — |
| N,N'-Dimethylacetamide | — |
| N,N'-Dimethylformamide | — |
| 1,4-Dioxane | — |
| 2-Ethoxyethanol | — |
| Ethanol | — |
| Ethyl acetate | — |
| Isopropyl acetate | — |
| Methanol | — |
| Methyl ethyl ketone | — |
| 2-Methyltetrahydrofuran | — |
| 1-Propanol | — |
| 2-Propanol | — |
| Tetrahydrofuran | — |
| Toluene | — |
| Water | — |
| Acetone:Water (90:10 v/v) | — |
| Ethanol:Water (90:10 v/v) | — |
| Dichloromethane:Methanol (90:10 v/v) | — |
| Dichloromethane Methanol (25:75 v/v) | N/A |
| Polyethylene glycol | — |

*"A": Amorphous Form;
"—": Insufficient Solid

Anti-Solvent Addition at Ambient Temperature: Up to 1 mL of anti-solvent was added dropwise to stirred, saturated solutions of Compound A. The experiments were then uncapped and allowed to evaporate at ambient temperature. All solids recovered were analyzed by XRPD. The results are shown below in Table 9.

TABLE 9

Anti-Solvent Addition Results

| Solvent | Anti-Solvent | Volume Added (µL) | Observations | XRPD Pattern |
|---|---|---|---|---|
| Acetone | Heptane | 200 | Cloudy with solids | A |
| Acetonitrile | tert-Butyl methyl ether | 1000 | Clear solution | — |
| 1-Butanol | Heptane | 1000 | Clear solution | — |
| Cyclohexane | Heptane | 1000 | Clear solution | — |
| Dichloromethane | Heptane | 100 | Cloudy with solids | A |
| N,N'-Dimethylacetamide | tert-Butyl methyl ether | 500 | Cloudy | A |
| N,N'-Dimethylformamide | tert-Butyl methyl ether | 700 | Cloudy | A |
| 1,4-Dioxane | Heptane | 500 | Cloudy with solids | A |
| 2-Ethoxyethanol | Heptane | 250 | Cloudy with solids | A |
| Ethanol | Heptane | 1000 | Clear solution | A (through evaporation) |
| Ethyl acetate | Heptane | 1000 | Thin haze | A (through evaporation) |
| Isopropyl acetate | Heptane | 100 | Cloudy with solids | — |
| Methanol | tert-Butyl methyl ether | 500 | Clear solution | — |
| Methyl ethyl ketone | Heptane | 250 | Cloudy | — |
| 2-Methyltetrahydrofuran | Heptane | 1000 | Cloudy | — |
| 1-Propanol | Heptane | 1000 | Clear solution | A (through evaporation) |

TABLE 9-continued

Anti-Solvent Addition Results

| Solvent | Anti-Solvent | Volume Added (μL) | Observations | XRPD Pattern |
|---|---|---|---|---|
| 2-Propanol | Heptane | 1000 | Clear solution | — |
| Tetrahydrofuran | Heptane | 100 | Solids | A |
| Toluene | Heptane | 1000 | Clear solution | — |
| Water | 1,4-Dioxane | 1000 | Clear solution | — |
| Acetone:Water (90:10 v/v) | 1,4-Dioxane | 1000 | Clear solution | — |
| Ethanol:Water (90:10 v/v) | 1,4-Dioxane | 1000 | Clear solution | — |
| Dichloromethane:Methanol (90:10 v/v) | tert-Butyl methyl ether | 150 | Cloudy with solids | A |
| Dichloromethane:Methanol (25:75 v/v) | tert-Butyl methyl ether | 100 | Solids | IV (poorly crystalline) |
| Polyethylene glycol | 1,4-Dioxane | 1000 | Clear solution | — |

Example 3: Form I

Approximately 30 mg of amorphous Compound A free base was suspended in 1.0 mL methyl ethyl ketone. The experiment was temperature cycled between ambient temperature (ca. 22° C.) and 40° C. in 4-hour cycles for 72 hours. After 72 hours, the solids were isolated by centrifuge filtration and dried at 40° C. for 18 hours, then analyzed.

Form I was found to be a thermodynamically stable, non-solvated form with a high melting point (259° C.). This form possesses excellent stability, good solubility in process relevant solvents and improved solubility at lower biorelevant pH, as well as low hygroscopicity (1.7 wt. % at 90% RH). Of the four forms identified, Form I was determined to be the most stable. A summary of the relevant characteristics of Form I is found below in Table 10:

TABLE 10

| Form I Characteristics | | | |
|---|---|---|---|
| Isolated yield | | 60% | |
| XRPD | | Crystalline | |
| Morphology | | Irregular | |
| Weight loss to 330° C. (TGA) | | 0.4% | |
| Thermal events (DTA) | | onset 253° C., peak 257° C. | |
| Thermal events (DSC) | | onset 255° C., peak 259° C. | |
| Solvent content/wt. % ($^1$H NMR) | | 0.2 | |
| Acid stoichiometry ($^1$H NMR) | | n/a | |
| Purity/% | | 99.2 | |
| Hygroscopicity (water uptake at 90% RH) | | 1.7% | |
| Post-DVS XRPD | | Form I | |
| 1 Week Stability | 40° C./75% RH | Form I | 99.2% |
| | 80° C. | Form I | 98.8% |
| | Ambient | Form I | 99.1% |
| Thermodynamic solubility/mg/mL | 1-Butanol | Form I | 0.5 |
| | Methanol | Form I | 1.1 |
| | Ethanol | Form I | 0.8 |
| | THF | n/a | >67 |
| | Acetone | Form I (PO) | 4.0 |
| | DCM:Methanol (90:10 v/v) | n/a | >67 |
| | Dichloromethane | Form I (PO) | 14.8 |
| | N,N'-Dimethylacetamide | n/a | >100 |
| | pH 1 | Form I | 0.1 |
| | pH 4 | Amorphous | <0.05 |
| | pH 5 | Form I | <0.05 |
| | pH 6 | Form I | <0.05 |

Alternative Isolation of Form I from Polyethylene Glycol

Amorphous or partially amorphous solid was slurried in PEG-400 and temperature cycled between RT and 40° C. overnight. The solids were isolated from the supernatant, washed first with ethanol and then methyl ethyl ketone, and dried in a vacuum oven to yield flat, plate-like crystals.

Example 4: Form II

Approximately 30 mg of amorphous Compound A free base was suspended in 0.5 mL dichloromethane. The experiment was temperature cycled between ambient temperature (ca. 22° C.) and 40° C. in 4-hour cycles for 72 hours. After 72 hours, the solids were isolated by centrifuge filtration and dried at 40° C. for 18 hours, then analyzed.

Form II appears to be a crystalline, kinetic form. It appears to be non-solvated and likely hydrated. It has very small particle size and acicular rod morphology.

Example 5: Form III

Approximately 30 mg of amorphous Compound A free base was suspended in 1.0 mL acetonitrile. The experiment was temperature cycled between ambient temperature (ca. 22° C.) and 40° C. in 4-hour cycles for 72 hours. After 72 hours, the solids were isolated by centrifuge filtration and dried at 40° C. for 18 hours, then analyzed.

Form III appears to be a crystalline, kinetic form. It possesses a high melting temperature after de-hydration (onset 196° C.). It appears to be non-solvated and likely hydrated. It shows some loss of crystallinity on de-hydration.

Example 6: Form IV

Approximately 30 mg of amorphous Compound A free base was suspended in 1.0 mL dichloromethane:methanol (25:75 v/v). The experiment was temperature cycled between ambient temperature (ca. 22° C.) and 40° C. in 4-hour cycles for 72 hours. After 72 hours, the sample was filtered through a 0.22 μm nylon filter and the supernatant retained. The supernatant was cooled to between 2 and 8° C. in a refrigerator and held for 72 hours. After 72 hours, the resulting solids were isolated by centrifuge filtration and analyzed as a damp powder.

Form IV was found to be partly crystalline.

The invention claimed is:
1. Crystalline (S)-3-(5-(4-((1-(4-((1R,2S)-6-hydroxy-2-phenyl-1,2,3,4-tetrahydronaphthalen-1-yl)phenyl)piperidin-4-yl)methyl)piperazin-1-yl)-1-oxoisoindolin-2-yl)piperidine-2,6-dione (Compound A)

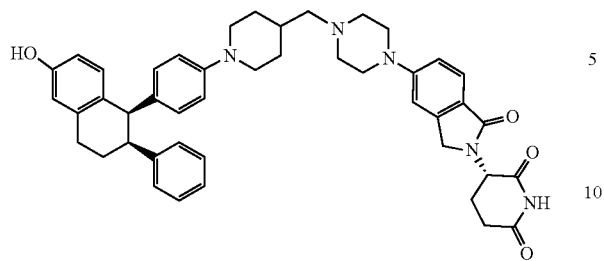

(Compound A)

characterized by an X-ray powder diffraction pattern having peaks at 4.1 °2θ±0.2°2θ, 13.9°2θ±0.2°2θ, 16.4°2θ±0.2°2θ, and 17.9°2θ±0.2°2θ using Cu Kα radiation at an x-ray wavelength of 1.5406 Å.

2. A pharmaceutical composition comprising the crystalline Compound A of claim 1, and a pharmaceutically acceptable carrier.

3. The crystalline Compound A of claim 1, wherein Compound A is substantially anhydrous.

4. The crystalline Compound A of claim 1, wherein Compound A is substantially unsolvated.

5. The crystalline Compound A of claim 1, wherein Compound A is substantially anhydrous and unsolvated.

6. The crystalline Compound A of claim 1, wherein Compound A is about 99% pure.

* * * * *